(12) United States Patent
Briers et al.

(10) Patent No.: US 9,809,808 B2
(45) Date of Patent: Nov. 7, 2017

(54) ANTIMICROBIAL AGENTS

(75) Inventors: Yves Briers, Rohr AG (CH); Rob Lavigne, Ekeren (BE); Guido Volckaert, Holsbeek (BE)

(73) Assignee: KATHOLIEKE UNIVERSITEIT LEUVEN K.U. LEUVEN R&D, Leuven (BE)

( * ) Notice: Subject to any disclaimer, the term of this patent is extended or adjusted under 35 U.S.C. 154(b) by 807 days.

(21) Appl. No.: 13/061,053

(22) PCT Filed: Aug. 25, 2009

(86) PCT No.: PCT/EP2009/060947
§ 371 (c)(1),
(2), (4) Date: May 31, 2011

(87) PCT Pub. No.: WO2010/023207
PCT Pub. Date: Mar. 4, 2010

(65) Prior Publication Data
US 2011/0243915 A1 Oct. 6, 2011

(30) Foreign Application Priority Data
Aug. 26, 2008 (GB) .................................. 0815484.1

(51) Int. Cl.
C12N 9/52 (2006.01)
C12N 9/36 (2006.01)
A61K 38/00 (2006.01)

(52) U.S. Cl.
CPC ............. *C12N 9/2462* (2013.01); *C12N 9/52* (2013.01); *A61K 38/00* (2013.01)

(58) Field of Classification Search
CPC ......... H04M 1/03; H04R 17/00; A61K 38/00; A61K 38/47; C12N 9/2462; C12N 15/52; C12N 15/62; C12N 9/503; C12N 9/52; A61L 2/00; C07K 14/005; C07K 14/4723; C07K 2319/00; C07K 2319/20; C12Y 302/01; A47L 13/16; D04H 11/08
See application file for complete search history.

(56) References Cited

U.S. PATENT DOCUMENTS

| | | | |
|---|---|---|---|
| 5,985,271 A | 11/1999 | Fischetti et al. | ............. 424/94.1 |
| 5,993,809 A | 11/1999 | Weaver et al. | |
| 6,440,935 B1 | 8/2002 | Jaynes | |
| 6,503,881 B2 | 1/2003 | Krieger et al. | |
| 6,936,244 B2 | 8/2005 | Fiochetti et al. | ............. 424/94.1 |
| 7,572,602 B1 | 8/2009 | Donovan | |
| 2002/0127220 A1 | 9/2002 | Fiochetti et al. | |
| 2006/0147442 A1 | 7/2006 | Homan et al. | |
| 2009/0130185 A1 | 5/2009 | Coote et al. | |
| 2010/0092968 A1 | 4/2010 | Beissinger et al. | ................ 435/6 |

FOREIGN PATENT DOCUMENTS

| | | |
|---|---|---|
| DE | 10 2006 061002 | 6/2008 |
| EP | 0 510 907 | 10/1992 |
| WO | WO 94/04688 | 3/1994 |
| WO | WO 96/06532 | 3/1996 |
| WO | WO 00/12528 | 3/2000 |
| WO | WO 01/00855 | 1/2001 |
| WO | WO 03/089455 | 10/2003 |
| WO | WO 2005/024002 | 3/2005 |
| WO | WO 2005/108563 | 11/2005 |
| WO | WO 2007/022768 | 3/2007 |
| WO | WO 2009/041830 | 4/2009 |
| WO | WO 2009/068858 | 6/2009 |
| WO | WO 2010/011960 | 1/2010 |
| WO | WO 2010/020657 | 2/2010 |
| WO | WO 2010/023207 | 3/2010 |
| WO | WO 2010/091294 | 8/2010 |

(Continued)

OTHER PUBLICATIONS

Fischetti, V. A. (2010) International Journal of Medical Microbiology 300 (6): 357-362.*
Fischetti, V. A. (2008) Current Opinion in Microbiology 11(5): 393-400.*
Arima et al., "Bactericidal action of lysozymes attached with various sizes of hydrophobic peptides to the C-terminal using genetic modification," *FEBS Letters*, 415(1):114-118, 1997.
Cheng, et al., "Removing group B streptococci colonizing the vagina and pharynx of mice with a bacteriophage lytic enzyme," *Antimicrob. Agents Chemother.*, 49: 111-117, 2005.
Ibrahim et al., "Enhanced bactericidal action of lysozyme to *Escherichia coli* by inserting a hydrophobic pentapeptide into its C terminus," *The Journal of Biological Chemistry*, 269(7):5059-5063, 1994.

(Continued)

*Primary Examiner* — Lisa J Hobbs
(74) *Attorney, Agent, or Firm* — Parker Highlander PLLC

(57) ABSTRACT

The present invention relates to endolysin variants comprising an endolysin to which a peptide stretch with membrane or LPS disrupting activity is fused. Moreover, the present invention relates to nucleic acid molecules encoding said modified endolysin variant, vectors comprising said nucleic acid molecules and host cells comprising either said nucleic acid molecules or said vectors. In addition, the present invention relates to a method for producing said endolysin variant. Further, the present invention relates to said modified endolysin variant for use as a medicament, in particular for the treatment or prevention of Gram-negative bacterial infections, as diagnostic means, disinfectant or as cosmetic substance. The present invention also relates to the removal or reduction or prevention of Gram-negative bacterial contamination of foodstuff, of food processing equipment, of food processing plants, of surfaces coming into contact with foodstuff, of medical devices, of surfaces in hospitals and surgeries. Furthermore, the present invention relates to the use of said endolysin variant as a diagnostic means in medicinal, food or feed or environmental diagnostic. Finally, the present invention relates to a pharmaceutical composition comprising said modified endolysin variant.

15 Claims, 12 Drawing Sheets

(56) References Cited

FOREIGN PATENT DOCUMENTS

Figure 1:
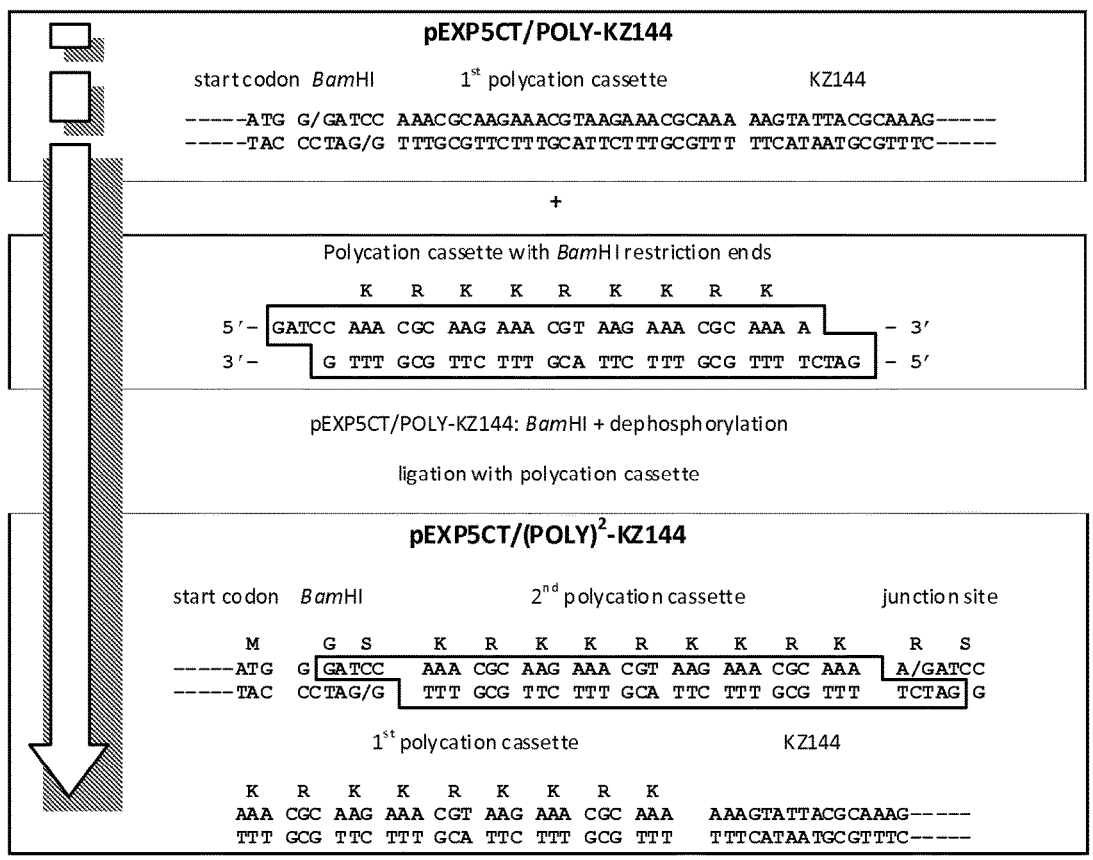

| WO | WO 2010/149792 | 12/2010 |
|---|---|---|
| WO | WO 2011/023702 | 3/2011 |
| WO | WO 2011/134998 | 11/2011 |

OTHER PUBLICATIONS

Loeffler et al., "Rapid killing of *Streptococus pneumoniae* with a bacteriophage cell wall hydrolase: A new approach to eliminate mucosal carriage," *Science*, 294: 2170-2172, 2001.
Loessner, "Bacteriophage endolysins—current state of research and applications," *Current Opinion in Microbiology*, 8(4):480-487, 2005.
Morita et al, "Functional analysis of antibacterial activity of Bacillus amyloliquefaciens phage endolysin against Gram-negative bacteria," *FEBS Letters*, 500(1-2):56-59, 2001.
Orito et al., "Bacillus amyloliquefaciens phage endolysin can enhance permeability of Pseudomonas aeruginosa outer membrane and induce cell lysis," *Applied Microbiology and Biotechnology*, 65(1):105-109, 2004.
PCT International Preliminary Report on Patentability, issued in International application No. PCT/EP2009/060947, dated Jan. 11, 2011.
Rashel et al., "Efficient elimination of multidrug-resistant *Staphylococcus aureus* by cloned lysin derived from bacteriophage phi MR11," *J Infect Dis*. 196(8):1237-47, 2007.
Schuch et al., "Identification of a bacteriolytic agent that can rapidly and specifically detect and kill bacillus anthracis," *Nature*, 418: 884-889, 2002.
Vollmer et al., "Bacterial peptidoglycan (murein) hydrolases," *FEMS Microbiol. Rev.*, 32(2):259-86, 2008.
Wilcox, "The new antimicrobials: Cationic peptides," *Bioteach Journal*, 2:88-91, 2004.
Zasloff, "Antimicrobial peptides of multicellular organisms," *Nature*, 415:389-395, 2002.
Díaz et al., "Chimeric phage-bacterial enzymes: a clue to the modular evolution of genes," *Proc. Natl. Acad. Sci. USA*, 87:8125-8129, 1990.
Diaz et al., "Chimeric pneumococcal cell wall lytic enzymes reveal important physiological and evolutionary traits," *The Journal of Biological Chemistry*, 266(9):5464-5471, 1991.
Terpe, "Overview of tag protein fusions: from molecular and biochemical fundamentals to commercial sysetms," *Appl Microbiol Biotechnol*, 60:523-533, 2003.
"LYS_BPCP1", EBI accession No. UNITPROT:P15057, dated Apr. 1, 1990.
"pET-21-d(+) Vectors", Product Information Sheet, Novagen 1998.
"PHIKZ144 [Pseudomonas phage phiKZ]", Genbank Accession No. AAL83045.1, downloaded from www.ncbi.nlm.nih.gov, 2002.
Borysowski et al., "Bacteriophage endolysins as a novel class of antibacterial agents", *Exp Biol Med.*, 231:366-377, 2006.
Briers et al., "A standardized approach for accurate quantification of murein hydrolase activity in high-throughput assays," *J. Biochem. Biophys. Methods*, 70:531-533, 2007.
Briers et al., "Muralytic activity and modular structure of the endolysins of *Pseudomonas aeruginosa* bacteriophages ΦKZ and EL", *Molecular Microbiology*, 65(5):1334-1344, 2007.
Conlon et al., "Peptidomic analysis of skin secretions supports separate species status for the tailed frogs, *Ascaphus truei* and *Ascaphus montanus*," *Comparative Biochemistry and Physiology*, 2(2):121-125, 2007.
Ding et al., "The Sushi peptides: structural characterization and mode of action against Gram-negative bacteria", *Cell Mol Life Sci.*, 65(7-8):1202-19, 2008.
Dmitriev et al., "Tertiary structure of *Staphylococcus aureus* cell wall murein", *J Bacteriol.*, 186(21):7141-7148, 2004.
Donovan, et al., "Petidoglycan hydrolase fusions maintain their parental specificities," *Applied and Environmental Microbiology*, 72(4);2988-2996, 2006.
Düring et al., "The non-enzymatic microbicidal activity of lysoymes," *FEBS Letters*, 449:93-100, 1999.
Falla et al., "Mode of action of the antimicrobial peptide indolicidin", *J Biol Chem.*, 271:19298-19303, 1996.
García et al., "Molecular evolution of lytic enzymes of *Streptococcus pneumoniae* and its bacteriophages", *Proc Natl Acad Sci USA*, 85:914-918, 1988.
Ito et al., "Bactericidal activity of human lysozymes carrying various lengths of polyproline chain at the C-terminus," *FEBS Letters*, 415:285-288, 1997.
Jado et al., "Phage lytic enzymes as therapy for antibiotic-resistant *Streptococcus pneumoniae* infection in a murine sepsis model," *Journal of Antimicrobial Chemotherapy*, 52(6):967-973, 2003.
Li et al., "Potential therapeutic efficacy of a bactericidal-immunomodulatory fusion peptide against methicillin-resistant *Staphylococcus aureus* skin infection", *Appl Microbiol Biotechnol.*, 86:305-309, 2010.
Lopez et al., "Enzymes for anti-infective therapy: phage lysins," *Drug Discovery Today*, 1(4):469-474, 2004.
Lu et al., "Expression of the antimicrobial peptide cecropin fused with human lysozyme in *Escherichia coli*", *Appl Microbiol Biotechnol.*, 87:2169-2176, 2010.
Manoharadas et al., "Antimicrobial activity of a chimeric enzybiotic towards *Staphylococcus aureus*," *Journal of Biotechnology*, 139(1):118-123, 2009.
Matthews and Remington, "The three dimensional structure of the lysozyme from bacteriophage T4", *Proc Natl Acad Sci USA*, 71:4178-4182, 1974.
Melo et al., "Antimicrobial peptides: linking partition, activity and high membrane-bound concentrations", *Nat Rev Microbiol.*, 7(3):245-50, 2009.
Muyombwe et al., "Cloning and expression of a gene encoding the lytic functions of *Bacillus amyloliquefaciens* phage: evidence of an auxiliary lysis system", *Journal of Bioscience and BioEngineering*, 88(2):221-225, 1999.
Nelson et al., "Prevention and elimination of upper respiratory colonization of mice by group A streptococci using a bacteriophage lytic enzyme," *Proc. Natl. Acad. Sci. U.S.A.*, 98: 4107-4112, 2001.
Niu et al., "The molecular design of a recombinant antimicrobial peptide CP and its in vitro activity", *Protein Expression and Purification*, 57:95-100, 2008.
Park et al., "Parasin I, an antimicrobial peptide derived from histone H2A in the catfish, *Parasilurus asotus*", *FEBS Lett.*, 437(3):258-62, 1998.
Powers et al., "The relationship between peptide structure and antibacterial activity", *Peptides*,24:1681-1691, 2003.
Tack et al., "SMAP-29 has two LPS-binding sites and a central hinge", *Eur J Biochem.*, 269:1181-1189, 2002.
Tan et al., "Definition of endotoxin binding sites in horseshoe crab factor C recombinant sushi proteins and neutralization of endotoxin by sushi peptides," *FASEB J.*, 14(12):1801-13, 2000.
Van Der Linden et al., "Synergistic effects of ovine-derived cathelicidins and other antimicrobials against *Escherichia coli* O157:H7 and *Staphylococcus aureus* 1056 MRSA", *Biotechnology Letters*, 31(8):1265-1267, 2009.
Yan and Adams, "Lycotoxins, antimicrobial peptides from venom of the wolf spider, *Lycosa carolinensis*", *J Biol Chem.*, 273:2059-2066, 1998.
Zhou et al., "TrxA mediating fusion expression of antimicrobial peptide CM4 from multiple joined genes in *Escherichia coli*," *Protein Expr. Purif.*, 64(2):225-230, 2009.
"Infection", Great Soviet Encyclopedia, dated 1969-1978. English Translation.
Becker et al., "The phage K lytic enzyme LysK and lysostaphin act synergistically to kill MRSA", *FEMS Microbiol Lett.*, 287(2):185-91, 2008.
Bülow and Mosbach, "Multienzyme systems obtained by gene fusion", *Trends Biotechnol.*, 9(7):226-31, 1991.
Fokine et al., "Structure of the bacteriophage ϕKZ lytic transglycosylase pg144", *J Biol Chem.*, 283(11):7242-50, 2007.
*JSCE Now*, 109:26-28, 2003. [Japanese language only].
Park et al., "Topological dynamics of holins in programmed bacterial lysis", *PNAS*, 103(52):19713-19718.

(56) References Cited

OTHER PUBLICATIONS

Sanz and Garcia, "Structural studies of the lysozyme coded by the pneumococcal phage Cp-1: conformational changes induced by choline", *Eur J Biochem*, 187:409-416, 1990.
"Lysozyme," Wikipedia website located at http://en.wikipedia.org/wiki/Lysozyme; downloaded Jul. 31, 2014.
Amersham Pharmacia Biotech BioDirectory, p. 94, print 2000.
Amersham Pharmacia Biotech Catalogue, p. 332, print 1998.
Boehringer Mannheim Biochemicals Catalog, p. 13, print 1996.
Brandenburg et al., "Biophysical characterization of lysozyme binging to LPS Re and lipid A", *Eur J Biochem.*, 258: 686-695, 1998.
Deacon et al., "Protein crystallography using a multilayer monochromator", *J Synchrotron Rad.*, 5: 494-496, 1998.
England et al., "Functional characterization of the somatic hypermutation process leading to antibody D1.3, a high affinity antibody directed against lysozyme", *J Immunol.*, 162: 2129-2136, 1999.
Garlitz et al., "Ethylammonium nitrate: a protein crystallization reagent", *Acta Cryst.*, D55: 2037-2038, 1999.
ICN 2000-2001 catalogue for Cell Culture, p. 41, print 2000.
Leitch and Willcox, "Synergic antistaphylococcal properties of lactoferrin and lysozyme", *J Med Microbiol.*, 47: 837-842, 1998.
Merck KGaA Catalogue, p. 819, print 1996.
Merk et al., "Cell-free expression of two single-chain monoclonal antibodies agains lysozyme: effect of domain arrangement on the expression", *J Biochem.*, 125: 328-333, 1999.
Oncor Appligene 1996-1997 Catalogue, p. 201, print 1996.
Reimann et al., "Proteins in vacuo: A molecular dynamics study of the unfolding behavior of highly charged disulfide-bond-intact lysozyme subjected to a temperature pulse", *Phys Rev E Stat Phys Plasmas Fluids Relat Interdiscip Topics*, 60: 7277-84, 1999.
Ruckenstein and Zeng, "Macroporous chitin affinity membranes for lysozyme separation", *Biotechnology and Engineering*, 56(6): 610-617, 1997.
Branden et al., Introduction to Protein Structure, Garland Publishing Inc., New York, p. 247, 1991.
Briers et al., The high-affinity peptidoglycan binding domain of Pseudomonas phage endolysin KZ144, Biochem. Biophys. Res. Comm., 2009, 383, 187-91.
Feng et al., Construction of the recombinant plasmid expressing a novel fusion protein cecropin B human lysozyme, Biotechnology, 2004, 14, 3-5. (English Translation).
GenBank, Accession No. AAL83045.1, 2002, www.ncbi.nlm.nih.gov.
GenBank, Accession No. AY030242.1, 2001, www.ncbi.nlm.nih.gov.
Graham and Coote. "Potent, synergistic inhibition. Of Staphylococcus aureus upon. exposure to a combination of the endopeptidase lysostaphin and the cationic peptide ranalexin." *Journal of antimicrobial chemotherapy* 59.4 (2007): 759-762.
Ibrahim et al., Strategies for New Antimicrobial Proteins and Peptides: Lysozyme and Aprotinin as Model Molecules, Cliff. Pharma. Design, 2002, 8, 671-93.
Lowenberger et al., Antimicrobial activity spectrum, cDNA cloning, and mRNA expression of a newly isolated member of the cecropin family from the mosquito vector Aedes aegypti, J. Biol. Chem., 1999, 274, 20092-97.
Maloy et at. "Structure—activity studies on magainins and other host defense peptides." *Biopolymers* 37,2 (1995): 105-122.
pET-32a-c( +) Vectors, Product Insert, Novagen, 1998.
Sadowski and Jones. "The sequence—structure relationship and protein function prediction." *Current opinion in structural biology* 19.3 (2009): 357-362.
Seffernick et al. "Melamine deaminase and atrazine chlorolaydrolase: 98 percent identical but functionally different," *Journal of Bacteriology* 183,8 (2001): 2405-2410.
Steiner et al., Sequence and specificity of two antibacterial proteins involved in insect immunity, Nature, 1981, 292, 246-48.
Stojkovic et al., Coliphage N4 N-Acetylmuramidase Defines a New Family of Murein Hydrolases, J. Mol. Biol., 2007, 366, 406-19.
Tossi et al. "Arnphipathic, a-helical antimicrobial peptides." *Peptide Science* 55.1 (2000): 4-30.
Witkowski etal. "Conversion of a p-ketoacyl synthase to a rtrilonyl decarboxylase by replacement of the active-site cysteine with glutamine." *Biochemistry* 38,36 (1999): 11643-11650.
Wroblewski, "Effect of natural amphipathic peptides on viability, membrane potential, cell shape and motility of mollicutes", *Res Microbiol.*, 148(2):163-75, 1997. (Abstract only).
Zhen et al.," Anticancer Drug Research and Development", 2004, figures p. 633.

\* cited by examiner

SEQUENCE LISTING

<160> NUMBER OF SEQ ID NOS: 83

<210> SEQ ID NO 1
<211> LENGTH: 260
<212> TYPE: PRT
<213> ORGANISM: unknown
<220> FEATURE:
<223> OTHER INFORMATION: phiKZgp144

<400> SEQUENCE: 1

Met Lys Val Leu Arg Lys Gly Asp Arg Gly Asp Glu Val Cys Gln Leu
1               5                   10                  15

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Cys Leu Asp Ser Asp Gly Ile Val Gly Lys Asn Thr Trp Ala Glu
    50                  55                  60

Leu Phe Ser Lys Tyr Ser Pro Pro Ile Pro Tyr Lys Thr Ile Pro Met
65                  70                  75                  80

Pro Thr Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Ile Lys Ala Lys Thr Ser Ser
        115                 120                 125

Ala Thr Gly Trp Phe Gln Phe Leu Thr Gly Thr Trp Lys Thr Met Ile
    130                 135                 140

Glu Asn Tyr Gly Met Lys Tyr Gly Val Leu Thr Asp Pro Thr Gly Ala
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Phe Gly Pro Gly Ala Ala Arg
        195                 200                 205

Arg Phe Leu Thr Thr Gly Gln Asn Glu Leu Ala Ala Thr His Phe Pro
    210                 215                 220

Lys Glu Ala Gln Ala Asn Pro Ser Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 2
<211> LENGTH: 292
<212> TYPE: PRT
<213> ORGANISM: unknown
<220> FEATURE:
<223> OTHER INFORMATION: ELgp188

<400> SEQUENCE: 2

Met Asn Phe Arg Thr Lys Asn Gly Tyr Arg Asp Leu Gln Ala Leu Val
1               5                   10                  15

Lys Glu Leu Gly Leu Tyr Thr Gly Gln Ile Asp Gly Val Trp Gly Lys
            20                  25                  30

```
Gly Thr Ser Ser Ser Thr Glu Thr Leu Leu Arg Gly Tyr Ala Glu Val
             35                  40                  45

Val Gly Lys Asn Thr Gly Gly Ile Gly Leu Pro Thr Thr Ser Asp Ala
 50                  55                  60

Ser Gly Tyr Asn Val Ile Thr Ala Leu Gln Arg Asn Leu Ala Phe Leu
 65                  70                  75                  80

Gly Leu Tyr Ser Leu Thr Val Asp Gly Ile Trp Gly Asn Gly Thr Leu
                 85                  90                  95

Ser Gly Leu Asp Lys Ala Phe Glu Val Tyr Lys Glu Arg Tyr Arg Thr
            100                 105                 110

Pro Thr Tyr Asp Ile Ala Trp Ser Gly Lys Val Ser Pro Ala Phe Thr
            115                 120                 125

Ala Lys Val Lys Asp Trp Cys Gly Val His Val Pro Asn His Arg Ala
        130                 135                 140

Pro His Trp Leu Met Ala Cys Met Ala Phe Glu Thr Gly Gln Thr Phe
145                 150                 155                 160

Ser Pro Ser Ile Lys Asn Ala Ala Gly Ser Glu Ala Tyr Gly Leu Ile
                165                 170                 175

Gln Phe Met Ser Pro Ala Ala Asn Asp Leu Asn Val Pro Leu Ser Val
            180                 185                 190

Ile Arg Ser Met Asp Gln Leu Thr Gln Leu Asp Leu Val Phe Lys Tyr
        195                 200                 205

Phe Glu Met Trp Met Lys Arg Gly Lys Arg Tyr Thr Gln Leu Glu Asp
    210                 215                 220

Phe Tyr Leu Thr Ile Phe His Pro Ala Ser Val Gly Lys Lys Ala Asp
225                 230                 235                 240

Glu Val Leu Phe Leu Gln Gly Ser Lys Ala Tyr Leu Gln Asn Lys Gly
                245                 250                 255

Phe Asp Val Asp Lys Asp Gly Lys Ile Thr Leu Gly Glu Ile Ser Ser
            260                 265                 270

Thr Leu Tyr Thr Thr Tyr Tyr Lys Gly Leu Leu Pro Glu Asn Arg His
        275                 280                 285

Val Ile Ser Tyr
    290

<210> SEQ ID NO 3
<211> LENGTH: 181
<212> TYPE: PRT
<213> ORGANISM: unknown
<220> FEATURE:
<223> OTHER INFORMATION: Salmonella endolysin

<400> SEQUENCE: 3

Met Lys Pro Lys Asp Glu Ile Phe Asp Glu Ile Leu Gly Lys Glu Gly
 1               5                  10                  15

Gly Tyr Val Asn His Pro Asp Asp Lys Gly Gly Pro Thr Lys Trp Gly
             20                  25                  30

Ile Thr Glu Lys Val Ala Arg Ala His Gly Tyr Arg Gly Asp Met Arg
             35                  40                  45

Asn Leu Thr Arg Gly Gln Ala Leu Glu Ile Leu Glu Thr Asp Tyr Trp
 50                  55                  60

Tyr Gly Pro Arg Phe Asp Arg Val Ala Lys Ala Ser Pro Asp Val Ala
 65                  70                  75                  80

Ala Glu Leu Cys Asp Thr Gly Val Asn Met Gly Pro Ser Val Ala Ala
                 85                  90                  95
```

Lys Met Leu Gln Arg Trp Leu Asn Val Phe Asn Gln Gly Gly Arg Leu
            100                 105                 110

Tyr Pro Asp Met Asp Thr Asp Gly Arg Ile Gly Pro Arg Thr Leu Asn
            115                 120                 125

Ala Leu Arg Val Tyr Leu Glu Lys Arg Gly Lys Asp Gly Glu Arg Val
        130                 135                 140

Leu Leu Val Ala Leu Asn Cys Thr Gln Gly Glu Arg Tyr Leu Glu Leu
145                 150                 155                 160

Ala Glu Lys Arg Glu Ala Asp Glu Ser Phe Val Tyr Gly Trp Met Lys
                165                 170                 175

Glu Arg Val Leu Ile
            180

<210> SEQ ID NO 4
<211> LENGTH: 163
<212> TYPE: PRT
<213> ORGANISM: unknown
<220> FEATURE:
<223> OTHER INFORMATION: Enterobacteria phage T4 endolysin

<400> SEQUENCE: 4

Met Asn Ile Phe Glu Met Leu Arg Ile Asp Glu Gly Leu Arg Leu Lys
1               5                   10                  15

Ile Tyr Lys Asp Thr Glu Gly Tyr Tyr Thr Ile Gly Ile Gly His Leu
            20                  25                  30

Leu Thr Lys Ser Pro Ser Leu Asn Ala Ala Lys Ser Glu Leu Asp Lys
        35                  40                  45

Ala Ile Gly Arg Asn Cys Asn Gly Val Ile Thr Lys Asp Glu Ala Glu
    50                  55                  60

Lys Leu Phe Asn Gln Asp Val Asp Ala Ala Val Arg Gly Ile Leu Arg
65                  70                  75                  80

Asn Ala Lys Leu Lys Pro Val Tyr Asp Ser Leu Asp Ala Val Arg Arg
                85                  90                  95

Cys Ala Leu Ile Asn Met Val Phe Gln Met Gly Glu Thr Gly Val Ala
            100                 105                 110

Gly Phe Thr Asn Ser Leu Arg Met Leu Gln Gln Lys Arg Trp Asp Glu
        115                 120                 125

Ala Ala Val Asn Leu Ala Lys Ser Arg Trp Tyr Asn Gln Thr Pro Asn
    130                 135                 140

Arg Ala Lys Arg Val Ile Thr Thr Phe Arg Thr Gly Thr Trp Asp Ala
145                 150                 155                 160

Tyr Lys Asn

<210> SEQ ID NO 5
<211> LENGTH: 280
<212> TYPE: PRT
<213> ORGANISM: unknown
<220> FEATURE:
<223> OTHER INFORMATION: Acinetobacter baumanii endolysin

<400> SEQUENCE: 5

Met Glu Tyr Asp Met Ile Leu Lys Phe Gly Ser Lys Gly Asp Ala Val
1               5                   10                  15

Ala Thr Leu Gln Lys Gln Leu Ala Lys Met Gly Tyr Lys Gly Val Lys
            20                  25                  30

Asp Lys Pro Leu Ser Val Asp Gly His Phe Gly Glu Ser Thr Glu Phe
        35                  40                  45

-continued

Ala Val Ile Gln Leu Gln Arg Lys Phe Gly Leu Val Ala Asp Gly Lys
 50                  55                  60

Val Gly Asp Lys Thr Arg Gln Ala Leu Ala Gly Asp Ser Val Ser Lys
 65                  70                  75                  80

Phe Leu Lys Asp Glu Asp Tyr Lys Lys Ala Ala Ile Arg Leu Lys Val
                 85                  90                  95

Pro Glu Leu Val Ile Arg Val Phe Gly Ala Val Glu Gly Leu Gly Val
            100                 105                 110

Gly Phe Leu Pro Asn Gly Lys Ala Lys Ile Leu Phe Glu Arg His Arg
        115                 120                 125

Met Tyr Phe Tyr Leu Cys Gln Ala Leu Gly Lys Thr Phe Ala Asn Ser
130                 135                 140

Gln Val Lys Ile Thr Pro Asn Ile Val Asn Thr Leu Thr Gly Gly Tyr
145                 150                 155                 160

Lys Gly Asp Ala Ala Glu Tyr Thr Arg Leu Ser Met Ala Ile Asn Ile
                165                 170                 175

His Lys Glu Ser Ala Leu Met Ser Thr Ser Trp Gly Gln Phe Gln Ile
            180                 185                 190

Met Gly Glu Asn Trp Lys Asp Leu Gly Tyr Ser Ser Val Gln Glu Phe
        195                 200                 205

Val Asp Gln Gln Gln Leu Asn Glu Gly Asn Gln Leu Glu Ala Phe Ile
210                 215                 220

Arg Phe Ile Glu Trp Lys Pro Gly Leu Leu Glu Ala Leu Arg Lys Gln
225                 230                 235                 240

Asp Trp Asp Thr Val Phe Thr Leu Tyr Asn Gly Lys Asn Tyr Lys Lys
                245                 250                 255

Leu Gly Tyr Gln Ala Lys Phe Gln Lys Glu Trp Asp His Leu Glu Pro
            260                 265                 270

Ile Tyr Arg Glu Lys Thr Ala Ala
        275                 280

<210> SEQ ID NO 6
<211> LENGTH: 152
<212> TYPE: PRT
<213> ORGANISM: unknown
<220> FEATURE:
<223> OTHER INFORMATION: E. coli K1F endolysin

<400> SEQUENCE: 6

Met Val Ser Lys Val Gln Phe Asn Pro Arg Ser Arg Thr Asp Ala Ile
1                5                  10                  15

Phe Val His Cys Ser Ala Thr Lys Pro Glu Met Asp Ile Gly Val Glu
             20                  25                  30

Thr Ile Arg Met Trp His Lys Gln Ala Trp Leu Asp Val Gly Tyr
         35                  40                  45

His Phe Ile Ile Lys Arg Asp Gly Thr Val Glu Glu Gly Arg Pro Val
    50                  55                  60

Asn Val Val Gly Ser His Val Lys Asp Trp Asn Ser Arg Ser Val Gly
65                  70                  75                  80

Val Cys Leu Val Gly Gly Ile Asn Ala Lys Gly Gln Phe Glu Ala Asn
                85                  90                  95

Phe Thr Pro Ala Gln Met Asn Ser Leu Arg Asn Lys Leu Asp Asp Leu
            100                 105                 110

Lys Val Met Tyr Pro Gln Ala Glu Ile Arg Ala His His Asp Val Ala
        115                 120                 125

```
Pro Lys Ala Cys Pro Ser Phe Asp Leu Gln Arg Trp Leu Ser Thr Asn
        130                 135                 140

Glu Leu Val Thr Ser Asp Arg Gly
145                 150
```

<210> SEQ ID NO 7
<211> LENGTH: 328
<212> TYPE: PRT
<213> ORGANISM: unknown
<220> FEATURE:
<223> OTHER INFORMATION: OBPgpLYS

<400> SEQUENCE: 7

```
Met Lys Asn Ser Glu Lys Asn Ala Ser Ile Ile Met Ser Ile Gln Arg
1               5                   10                  15

Thr Leu Ala Ser Leu Ser Leu Tyr Gly Gly Arg Ile Asp Gly Leu Phe
            20                  25                  30

Gly Glu Lys Cys Arg Gly Ala Ile Ile Leu Met Leu Asn Lys Val Tyr
        35                  40                  45

Pro Asn Phe Ser Thr Asn Lys Leu Pro Ser Asn Thr Tyr Glu Ala Glu
    50                  55                  60

Ser Val Phe Thr Phe Leu Gln Thr Ala Leu Ala Gly Val Gly Leu Tyr
65                  70                  75                  80

Thr Ile Thr Ile Asp Gly Lys Trp Gly Gly Thr Ser Gln Gly Ala Ile
                85                  90                  95

Asp Ala Leu Val Lys Ser Tyr Arg Gln Ile Thr Glu Ala Glu Arg Ala
            100                 105                 110

Gly Ser Thr Leu Pro Leu Gly Leu Ala Thr Val Met Ser Lys His Met
        115                 120                 125

Ser Ile Glu Gln Leu Arg Ala Met Leu Pro Thr Asp Arg Gln Gly Tyr
    130                 135                 140

Ala Glu Val Tyr Ile Asp Pro Leu Asn Glu Thr Met Asp Ile Phe Glu
145                 150                 155                 160

Ile Asn Thr Pro Leu Arg Ile Ala His Phe Met Ala Gln Ile Leu His
                165                 170                 175

Glu Thr Ala Cys Phe Lys Tyr Thr Glu Glu Leu Ala Ser Gly Lys Ala
            180                 185                 190

Tyr Glu Gly Arg Ala Asp Leu Gly Asn Thr Arg Pro Gly Asp Gly Pro
        195                 200                 205

Leu Phe Lys Gly Arg Gly Leu Leu Gln Ile Thr Gly Arg Leu Asn Tyr
    210                 215                 220

Val Lys Cys Gln Val Tyr Leu Arg Glu Lys Leu Lys Asp Pro Thr Phe
225                 230                 235                 240

Asp Ile Thr Ser Ser Val Thr Cys Ala Gln Gln Leu Ser Glu Ser Pro
                245                 250                 255

Leu Leu Ala Ala Leu Ala Ser Gly Tyr Phe Trp Arg Phe Ile Lys Pro
            260                 265                 270

Lys Leu Asn Glu Thr Ala Asp Lys Asp Ile Tyr Trp Val Ser Val
        275                 280                 285

Tyr Val Asn Gly Tyr Ala Lys Gln Ala Asn Pro Tyr Tyr Pro Asn Arg
    290                 295                 300

Asp Lys Glu Pro Asn His Met Lys Glu Arg Val Gln Met Leu Ala Val
305                 310                 315                 320

Thr Lys Lys Ala Leu Gly Ile Val
                325
```

```
<210> SEQ ID NO 8
<211> LENGTH: 165
<212> TYPE: PRT
<213> ORGANISM: unknown
<220> FEATURE:
<223> OTHER INFORMATION: PSP3gp10

<400> SEQUENCE: 8

Met Pro Val Ile Asn Thr His Gln Asn Ile Ala Ala Phe Leu Asp Met
1               5                   10                  15

Leu Ala Tyr Ser Glu Gly Thr Ala Asn His Pro Leu Thr Lys Asn Arg
            20                  25                  30

Gly Tyr Asp Val Ile Val Thr Gly Phe Asp Gly Ser Pro Glu Ile Phe
        35                  40                  45

Thr Asp Tyr Ser Asp His Pro Phe Ala His Gly Arg Pro Pro Lys Val
    50                  55                  60

Phe Asn Arg Arg Gly Glu Lys Ser Thr Ala Ser Gly Arg Tyr Gln Gln
65                  70                  75                  80

Leu Tyr Ile Phe Trp Pro His Tyr Lys Lys Gln Leu Ala Leu Pro Asp
                85                  90                  95

Phe Ser Pro Leu Ser Gln Asp Lys Leu Ala Ile Gln Leu Ile Arg Glu
            100                 105                 110

Arg Gly Ala Ile Asp Asp Ile Arg Ala Gly Arg Ile Glu Arg Ala Val
        115                 120                 125

Ser Arg Cys Arg Asn Ile Trp Ala Ser Leu Pro Gly Ala Gly Tyr Gly
    130                 135                 140

Gln Arg Glu His Ser Leu Glu Lys Leu Val Thr Val Trp Arg Thr Ala
145                 150                 155                 160

Gly Gly Val Met Ala
                165

<210> SEQ ID NO 9
<211> LENGTH: 165
<212> TYPE: PRT
<213> ORGANISM: unknown
<220> FEATURE:
<223> OTHER INFORMATION: P2gp09

<400> SEQUENCE: 9

Met Pro Val Ile Asn Thr His Gln Asn Ile Ala Ala Phe Leu Asp Met
1               5                   10                  15

Leu Ala Val Ser Glu Gly Thr Ala Asn His Pro Leu Thr Lys Asn Arg
            20                  25                  30

Gly Tyr Asp Val Ile Val Thr Gly Leu Asp Gly Lys Pro Glu Ile Phe
        35                  40                  45

Thr Asp Tyr Ser Asp His Pro Phe Ala His Gly Arg Pro Ala Lys Val
    50                  55                  60

Phe Asn Arg Arg Gly Glu Lys Ser Thr Ala Ser Gly Arg Tyr Gln Gln
65                  70                  75                  80

Leu Tyr Leu Phe Trp Pro His Tyr Arg Lys Gln Leu Ala Leu Pro Asp
                85                  90                  95

Phe Ser Pro Leu Ser Gln Asp Arg Leu Ala Ile Gln Leu Ile Arg Glu
            100                 105                 110

Arg Gly Ala Leu Asp Asp Ile Arg Ala Gly Arg Ile Glu Arg Ala Ile
        115                 120                 125

Ser Arg Cys Arg Asn Ile Trp Ala Ser Leu Pro Gly Ala Gly Tyr Gly
    130                 135                 140
```

```
Gln Arg Glu His Ser Leu Glu Lys Leu Val Thr Val Trp Arg Thr Ala
145                 150                 155                 160

Gly Gly Val Pro Ala
                165

<210> SEQ ID NO 10
<211> LENGTH: 6
<212> TYPE: PRT
<213> ORGANISM: unknown
<220> FEATURE:
<223> OTHER INFORMATION: synthetic peptide

<400> SEQUENCE: 10

Lys Arg Lys Lys Arg Lys
1               5

<210> SEQ ID NO 11
<211> LENGTH: 9
<212> TYPE: PRT
<213> ORGANISM: unknown
<220> FEATURE:
<223> OTHER INFORMATION: synthetic peptide

<400> SEQUENCE: 11

Lys Arg Lys Lys Arg Lys Lys Arg Lys
1               5

<210> SEQ ID NO 12
<211> LENGTH: 9
<212> TYPE: PRT
<213> ORGANISM: unknown
<220> FEATURE:
<223> OTHER INFORMATION: synthetic peptide

<400> SEQUENCE: 12

Arg Arg Arg Arg Arg Arg Arg Arg Arg
1               5

<210> SEQ ID NO 13
<211> LENGTH: 8
<212> TYPE: PRT
<213> ORGANISM: unknown
<220> FEATURE:
<223> OTHER INFORMATION: synthetic peptide

<400> SEQUENCE: 13

Lys Lys Lys Lys Lys Lys Lys Lys
1               5

<210> SEQ ID NO 14
<211> LENGTH: 10
<212> TYPE: PRT
<213> ORGANISM: unknown
<220> FEATURE:
<223> OTHER INFORMATION: synthetic peptide

<400> SEQUENCE: 14

Lys Arg Lys Lys Arg Lys Lys Arg Lys Lys
1               5                   10

<210> SEQ ID NO 15
<211> LENGTH: 12
<212> TYPE: PRT
<213> ORGANISM: unknown
<220> FEATURE:
<223> OTHER INFORMATION: synthetic peptide
```

```
<400> SEQUENCE: 15

Lys Arg Lys Lys Arg Lys Lys Arg Lys Lys Arg Lys
1               5                   10

<210> SEQ ID NO 16
<211> LENGTH: 14
<212> TYPE: PRT
<213> ORGANISM: unknown
<220> FEATURE:
<223> OTHER INFORMATION: synthetic peptide

<400> SEQUENCE: 16

Lys Arg Lys Lys Arg Lys Lys Arg Lys Lys Arg Lys Lys Arg
1               5                   10

<210> SEQ ID NO 17
<211> LENGTH: 16
<212> TYPE: PRT
<213> ORGANISM: unknown
<220> FEATURE:
<223> OTHER INFORMATION: synthetic peptide

<400> SEQUENCE: 17

Lys Lys Lys Lys Lys Lys Lys Lys Lys Lys Lys Lys Lys Lys Lys Lys
1               5                   10                  15

<210> SEQ ID NO 18
<211> LENGTH: 19
<212> TYPE: PRT
<213> ORGANISM: unknown
<220> FEATURE:
<223> OTHER INFORMATION: synthetic peptide

<400> SEQUENCE: 18

Lys Arg Lys Lys Arg Lys Lys Arg Lys Lys Arg Lys Lys Arg Lys Lys
1               5                   10                  15

Arg Lys Lys

<210> SEQ ID NO 19
<211> LENGTH: 19
<212> TYPE: PRT
<213> ORGANISM: unknown
<220> FEATURE:
<223> OTHER INFORMATION: synthetic peptide

<400> SEQUENCE: 19

Arg Arg Arg Arg Arg Arg Arg Arg Arg Arg Arg Arg Arg Arg Arg Arg
1               5                   10                  15

Arg Arg Arg

<210> SEQ ID NO 20
<211> LENGTH: 19
<212> TYPE: PRT
<213> ORGANISM: unknown
<220> FEATURE:
<223> OTHER INFORMATION: synthetic peptide

<400> SEQUENCE: 20

Lys Lys Lys Lys Lys Lys Lys Lys Lys Lys Lys Lys Lys Lys Lys Lys
1               5                   10                  15

Lys Lys Lys

<210> SEQ ID NO 21
```

```
<211> LENGTH: 20
<212> TYPE: PRT
<213> ORGANISM: unknown
<220> FEATURE:
<223> OTHER INFORMATION: synthetic peptide

<400> SEQUENCE: 21

Lys Arg Lys Lys Arg Lys Lys Arg Lys Arg Ser Lys Arg Lys Lys Arg
1               5                   10                  15

Lys Lys Arg Lys
            20

<210> SEQ ID NO 22
<211> LENGTH: 21
<212> TYPE: PRT
<213> ORGANISM: unknown
<220> FEATURE:
<223> OTHER INFORMATION: synthetic peptide

<400> SEQUENCE: 22

Lys Arg Lys Lys Arg Lys Lys Arg Lys Arg Ser Lys Arg Lys Lys Arg
1               5                   10                  15

Lys Lys Arg Lys Lys
            20

<210> SEQ ID NO 23
<211> LENGTH: 21
<212> TYPE: PRT
<213> ORGANISM: unknown
<220> FEATURE:
<223> OTHER INFORMATION: synthetic peptide

<400> SEQUENCE: 23

Lys Arg Lys Lys Arg Lys Lys Arg Lys Lys Arg Lys Lys Arg Lys Lys
1               5                   10                  15

Arg Lys Lys Arg Lys
            20

<210> SEQ ID NO 24
<211> LENGTH: 22
<212> TYPE: PRT
<213> ORGANISM: unknown
<220> FEATURE:
<223> OTHER INFORMATION: synthetic peptide

<400> SEQUENCE: 24

Lys Arg Lys Lys Arg Lys Lys Arg Lys Arg Gly Ser Gly Lys Arg Lys
1               5                   10                  15

Lys Arg Lys Lys Arg Lys
            20

<210> SEQ ID NO 25
<211> LENGTH: 24
<212> TYPE: PRT
<213> ORGANISM: unknown
<220> FEATURE:
<223> OTHER INFORMATION: synthetic peptide

<400> SEQUENCE: 25

Lys Arg Lys Lys Arg Lys Lys Arg Lys Arg Gly Ser Gly Ser Gly Lys
1               5                   10                  15

Arg Lys Lys Arg Lys Lys Arg Lys
            20
```

<210> SEQ ID NO 26
<211> LENGTH: 25
<212> TYPE: PRT
<213> ORGANISM: unknown
<220> FEATURE:
<223> OTHER INFORMATION: synthetic peptide

<400> SEQUENCE: 26

Lys Arg Lys Lys Arg Lys Lys Arg Lys Lys Arg Lys Lys Arg Lys Lys
1               5                   10                  15

Arg Lys Lys Arg Lys Lys Arg Lys Lys
            20                  25

<210> SEQ ID NO 27
<211> LENGTH: 31
<212> TYPE: PRT
<213> ORGANISM: unknown
<220> FEATURE:
<223> OTHER INFORMATION: synthetic peptide

<400> SEQUENCE: 27

Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys
            20                  25                  30

<210> SEQ ID NO 28
<211> LENGTH: 38
<212> TYPE: PRT
<213> ORGANISM: unknown
<220> FEATURE:
<223> OTHER INFORMATION: synthetic peptide

<400> SEQUENCE: 28

Lys Arg Lys Lys Arg Lys Lys Arg Lys Arg Gly Ser Gly Ser Gly Lys
1               5                   10                  15

Arg Lys Lys Arg Lys Lys Arg Lys Gly Ser Gly Ser Gly Lys Arg Lys
            20                  25                  30

Lys Arg Lys Lys Arg Lys
        35

<210> SEQ ID NO 29
<211> LENGTH: 39
<212> TYPE: PRT
<213> ORGANISM: unknown
<220> FEATURE:
<223> OTHER INFORMATION: synthetic peptide

<400> SEQUENCE: 29

Lys Arg Lys Lys Arg Lys Lys Arg Lys Lys Arg Lys Lys Arg Lys Lys
1               5                   10                  15

Arg Lys Lys Arg Lys Lys Arg Lys Lys Arg Lys Lys Arg Lys Lys Arg
            20                  25                  30

Lys Lys Arg Lys Lys Arg Lys
        35

<210> SEQ ID NO 30
<211> LENGTH: 42
<212> TYPE: PRT
<213> ORGANISM: unknown
<220> FEATURE:
<223> OTHER INFORMATION: synthetic peptide

<400> SEQUENCE: 30

```
Lys Arg Lys Lys Arg Lys Arg Lys Arg Ser Lys Arg Lys Lys Arg
1               5                   10                  15

Lys Lys Arg Lys Arg Ser Lys Arg Lys Lys Arg Lys Lys Arg Lys Arg
            20                  25                  30

Ser Lys Arg Lys Lys Arg Lys Lys Arg Lys
        35                  40
```

<210> SEQ ID NO 31
<211> LENGTH: 4
<212> TYPE: PRT
<213> ORGANISM: unknown
<220> FEATURE:
<223> OTHER INFORMATION: synthetic peptide

<400> SEQUENCE: 31

```
Ala Met Ser Gly
1
```

<210> SEQ ID NO 32
<211> LENGTH: 5
<212> TYPE: PRT
<213> ORGANISM: unknown
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: wherein Xaa is any other amino acid residue
      than lysine, arginine and histidine

<400> SEQUENCE: 32

```
Lys Arg Xaa Lys Arg
1               5
```

<210> SEQ ID NO 33
<211> LENGTH: 5
<212> TYPE: PRT
<213> ORGANISM: unknown
<220> FEATURE:
<223> OTHER INFORMATION: synthetic peptide

<400> SEQUENCE: 33

```
Lys Arg Ser Lys Arg
1               5
```

<210> SEQ ID NO 34
<211> LENGTH: 5
<212> TYPE: PRT
<213> ORGANISM: unknown
<220> FEATURE:
<223> OTHER INFORMATION: synthetic peptide

<400> SEQUENCE: 34

```
Lys Arg Gly Ser Gly
1               5
```

<210> SEQ ID NO 35
<211> LENGTH: 271
<212> TYPE: PRT
<213> ORGANISM: unknown
<220> FEATURE:
<223> OTHER INFORMATION: POLY-gp144

<400> SEQUENCE: 35

```
Met Gly Ser Lys Arg Lys Lys Arg Lys Lys Arg Lys Lys Val Leu Arg
1               5                   10                  15
```

```
Lys Gly Asp Arg Gly Asp Glu Val Cys Gln Leu Gln Thr Leu Leu Asn
            20                  25                  30

Leu Cys Gly Tyr Asp Val Gly Lys Pro Asp Gly Ile Phe Gly Asn Asn
        35                  40                  45

Thr Phe Asn Gln Val Val Lys Phe Gln Lys Asp Asn Cys Leu Asp Ser
 50                  55                  60

Asp Gly Ile Val Gly Lys Asn Thr Trp Ala Glu Leu Phe Ser Lys Tyr
 65                  70                  75                  80

Ser Pro Pro Ile Pro Tyr Lys Thr Ile Pro Met Pro Thr Ala Asn Lys
                 85                  90                  95

Ser Arg Ala Ala Ala Thr Pro Val Met Asn Ala Val Glu Asn Ala Thr
            100                 105                 110

Gly Val Arg Ser Gln Leu Leu Leu Thr Phe Ala Ser Ile Glu Ser Ala
        115                 120                 125

Phe Asp Tyr Glu Ile Lys Ala Lys Thr Ser Ser Ala Thr Gly Trp Phe
130                 135                 140

Gln Phe Leu Thr Gly Thr Trp Lys Thr Met Ile Glu Asn Tyr Gly Met
145                 150                 155                 160

Lys Tyr Gly Val Leu Thr Asp Pro Thr Gly Ala Leu Arg Lys Asp Pro
                165                 170                 175

Arg Ile Ser Ala Leu Met Gly Ala Glu Leu Ile Lys Glu Asn Met Asn
            180                 185                 190

Ile Leu Arg Pro Val Leu Lys Arg Glu Pro Thr Asp Thr Asp Leu Tyr
        195                 200                 205

Leu Ala His Phe Phe Gly Pro Gly Ala Ala Arg Arg Phe Leu Thr Thr
210                 215                 220

Gly Gln Asn Glu Leu Ala Ala Thr His Phe Pro Lys Glu Ala Gln Ala
225                 230                 235                 240

Asn Pro Ser Ile Phe Tyr Asn Lys Asp Gly Ser Pro Lys Thr Ile Gln
                245                 250                 255

Glu Val Tyr Asn Leu Met Asp Gly Lys Val Ala Ala His Arg Lys
            260                 265                 270

<210> SEQ ID NO 36
<211> LENGTH: 282
<212> TYPE: PRT
<213> ORGANISM: unknown
<220> FEATURE:
<223> OTHER INFORMATION: (POLY)2-gp144

<400> SEQUENCE: 36

Met Gly Ser Lys Arg Lys Arg Lys Lys Arg Lys Arg Ser Lys Arg
 1               5                  10                  15

Lys Lys Arg Lys Lys Arg Lys Lys Val Leu Arg Lys Gly Asp Arg Gly
            20                  25                  30

Asp Glu Val Cys Gln Leu Gln Thr Leu Leu Asn Leu Cys Gly Tyr Asp
        35                  40                  45

Val Gly Lys Pro Asp Gly Ile Phe Gly Asn Asn Thr Phe Asn Gln Val
 50                  55                  60

Val Lys Phe Gln Lys Asp Asn Cys Leu Asp Ser Asp Gly Ile Val Gly
 65                  70                  75                  80

Lys Asn Thr Trp Ala Glu Leu Phe Ser Lys Tyr Ser Pro Pro Ile Pro
                 85                  90                  95

Tyr Lys Thr Ile Pro Met Pro Thr Ala Asn Lys Ser Arg Ala Ala Ala
            100                 105                 110
```

Thr Pro Val Met Asn Ala Val Glu Asn Ala Thr Gly Val Arg Ser Gln
       115                 120                 125

Leu Leu Leu Thr Phe Ala Ser Ile Glu Ser Ala Phe Asp Tyr Glu Ile
130                 135                 140

Lys Ala Lys Thr Ser Ser Ala Thr Gly Trp Phe Gln Phe Leu Thr Gly
145                 150                 155                 160

Thr Trp Lys Thr Met Ile Glu Asn Tyr Gly Met Lys Tyr Gly Val Leu
            165                 170                 175

Thr Asp Pro Thr Gly Ala Leu Arg Lys Asp Pro Arg Ile Ser Ala Leu
            180                 185                 190

Met Gly Ala Glu Leu Ile Lys Glu Asn Met Asn Ile Leu Arg Pro Val
        195                 200                 205

Leu Lys Arg Glu Pro Thr Asp Thr Asp Leu Tyr Leu Ala His Phe Phe
    210                 215                 220

Gly Pro Gly Ala Ala Arg Arg Phe Leu Thr Thr Gly Gln Asn Glu Leu
225                 230                 235                 240

Ala Ala Thr His Phe Pro Lys Glu Ala Gln Ala Asn Pro Ser Ile Phe
                245                 250                 255

Tyr Asn Lys Asp Gly Ser Pro Lys Thr Ile Gln Glu Val Tyr Asn Leu
            260                 265                 270

Met Asp Gly Lys Val Ala Ala His Arg Lys
            275                 280

<210> SEQ ID NO 37
<211> LENGTH: 293
<212> TYPE: PRT
<213> ORGANISM: unknown
<220> FEATURE:
<223> OTHER INFORMATION: (POLY)3-gp144

<400> SEQUENCE: 37

Met Gly Ser Lys Arg Lys Lys Arg Lys Arg Ser Lys Arg
1               5                   10              15

Lys Lys Arg Lys Lys Arg Lys Ser Lys Arg Lys Arg Lys Lys
            20                  25                  30

Arg Lys Lys Val Leu Arg Lys Gly Asp Arg Gly Asp Glu Val Cys Gln
            35                  40                  45

Leu Gln Thr Leu Leu Asn Leu Cys Gly Tyr Asp Val Gly Lys Pro Asp
    50                  55                  60

Gly Ile Phe Gly Asn Asn Thr Phe Asn Gln Val Val Lys Phe Gln Lys
65                  70                  75                  80

Asp Asn Cys Leu Asp Ser Asp Gly Ile Val Gly Lys Asn Thr Trp Ala
                85                  90                  95

Glu Leu Phe Ser Lys Tyr Ser Pro Pro Ile Pro Tyr Lys Thr Ile Pro
            100                 105                 110

Met Pro Thr Ala Asn Lys Ser Arg Ala Ala Thr Pro Val Met Asn
            115                 120                 125

Ala Val Glu Asn Ala Thr Gly Val Arg Ser Gln Leu Leu Leu Thr Phe
    130                 135                 140

Ala Ser Ile Glu Ser Ala Phe Asp Tyr Glu Ile Lys Ala Lys Thr Ser
145                 150                 155                 160

Ser Ala Thr Gly Trp Phe Gln Phe Leu Thr Gly Thr Trp Lys Thr Met
                165                 170                 175

Ile Glu Asn Tyr Gly Met Lys Tyr Gly Val Leu Thr Asp Pro Thr Gly
            180                 185                 190

```
Ala Leu Arg Lys Asp Pro Arg Ile Ser Ala Leu Met Gly Ala Glu Leu
            195                 200                 205

Ile Lys Glu Asn Met Asn Ile Leu Arg Pro Val Leu Lys Arg Glu Pro
    210                 215                 220

Thr Asp Thr Asp Leu Tyr Leu Ala His Phe Phe Gly Pro Gly Ala Ala
225                 230                 235                 240

Arg Arg Phe Leu Thr Thr Gly Gln Asn Glu Leu Ala Ala Thr His Phe
                245                 250                 255

Pro Lys Glu Ala Gln Ala Asn Pro Ser Ile Phe Tyr Asn Lys Asp Gly
                260                 265                 270

Ser Pro Lys Thr Ile Gln Glu Val Tyr Asn Leu Met Asp Gly Lys Val
            275                 280                 285

Ala Ala His Arg Lys
            290

<210> SEQ ID NO 38
<211> LENGTH: 304
<212> TYPE: PRT
<213> ORGANISM: unknown
<220> FEATURE:
<223> OTHER INFORMATION: (POLY)4-gp144

<400> SEQUENCE: 38

Met Gly Ser Lys Arg Lys Lys Arg Lys Lys Arg Lys Arg Ser Lys Arg
1               5                   10                  15

Lys Lys Arg Lys Lys Arg Lys Ser Lys Arg Lys Lys Arg Lys Lys
            20                  25                  30

Arg Lys Arg Ser Lys Arg Lys Lys Arg Lys Lys Arg Lys Lys Val Leu
            35                  40                  45

Arg Lys Gly Asp Arg Gly Asp Glu Val Cys Gln Leu Gln Thr Leu Leu
    50                  55                  60

Asn Leu Cys Gly Tyr Asp Val Gly Lys Pro Asp Gly Ile Phe Gly Asn
65                  70                  75                  80

Asn Thr Phe Asn Gln Val Val Lys Phe Gln Lys Asp Asn Cys Leu Asp
                85                  90                  95

Ser Asp Gly Ile Val Gly Lys Asn Thr Trp Ala Glu Leu Phe Ser Lys
            100                 105                 110

Tyr Ser Pro Pro Ile Pro Tyr Lys Thr Ile Pro Met Pro Thr Ala Asn
        115                 120                 125

Lys Ser Arg Ala Ala Ala Thr Pro Val Met Asn Ala Val Glu Asn Ala
    130                 135                 140

Thr Gly Val Arg Ser Gln Leu Leu Leu Thr Phe Ala Ser Ile Glu Ser
145                 150                 155                 160

Ala Phe Asp Tyr Glu Ile Lys Ala Lys Thr Ser Ser Ala Thr Gly Trp
                165                 170                 175

Phe Gln Phe Leu Thr Gly Thr Trp Lys Thr Met Ile Glu Asn Tyr Gly
            180                 185                 190

Met Lys Tyr Gly Val Leu Thr Asp Pro Thr Gly Ala Leu Arg Lys Asp
        195                 200                 205

Pro Arg Ile Ser Ala Leu Met Gly Ala Glu Leu Ile Lys Glu Asn Met
    210                 215                 220

Asn Ile Leu Arg Pro Val Leu Lys Arg Glu Pro Thr Asp Thr Asp Leu
225                 230                 235                 240

Tyr Leu Ala His Phe Phe Gly Pro Gly Ala Ala Arg Arg Phe Leu Thr
                245                 250                 255
```

```
Thr Gly Gln Asn Glu Leu Ala Ala Thr His Phe Pro Lys Glu Ala Gln
                260                 265                 270

Ala Asn Pro Ser Ile Phe Tyr Asn Lys Asp Gly Ser Pro Lys Thr Ile
            275                 280                 285

Gln Glu Val Tyr Asn Leu Met Asp Gly Lys Val Ala Ala His Arg Lys
        290                 295                 300

<210> SEQ ID NO 39
<211> LENGTH: 303
<212> TYPE: PRT
<213> ORGANISM: unknown
<220> FEATURE:
<223> OTHER INFORMATION: POLY-gp188

<400> SEQUENCE: 39

Met Gly Ser Lys Arg Lys Lys Arg Lys Lys Arg Lys Asn Phe Arg Thr
1               5                   10                  15

Lys Asn Gly Tyr Arg Asp Leu Gln Ala Leu Val Lys Glu Leu Gly Leu
            20                  25                  30

Tyr Thr Gly Gln Ile Asp Gly Val Trp Gly Lys Gly Thr Ser Ser Ser
        35                  40                  45

Thr Glu Thr Leu Leu Arg Gly Tyr Ala Glu Val Gly Lys Asn Thr
    50                  55                  60

Gly Gly Ile Gly Leu Pro Thr Thr Ser Asp Ala Ser Gly Tyr Asn Val
65                  70                  75                  80

Ile Thr Ala Leu Gln Arg Asn Leu Ala Phe Leu Gly Leu Tyr Ser Leu
                85                  90                  95

Thr Val Asp Gly Ile Trp Gly Asn Gly Thr Leu Ser Gly Leu Asp Lys
            100                 105                 110

Ala Phe Glu Val Tyr Lys Glu Arg Tyr Arg Thr Pro Thr Tyr Asp Ile
        115                 120                 125

Ala Trp Ser Gly Lys Val Ser Pro Ala Phe Thr Ala Lys Val Lys Asp
130                 135                 140

Trp Cys Gly Val His Val Pro Asn His Arg Ala Pro His Trp Leu Met
145                 150                 155                 160

Ala Cys Met Ala Phe Glu Thr Gly Gln Thr Phe Ser Pro Ser Ile Lys
                165                 170                 175

Asn Ala Ala Gly Ser Glu Ala Tyr Gly Leu Ile Gln Phe Met Ser Pro
            180                 185                 190

Ala Ala Asn Asp Leu Asn Val Pro Leu Ser Val Ile Arg Ser Met Asp
        195                 200                 205

Gln Leu Thr Gln Leu Asp Leu Val Phe Lys Tyr Phe Glu Met Trp Met
    210                 215                 220

Lys Arg Gly Lys Arg Tyr Thr Gln Leu Glu Asp Phe Tyr Leu Thr Ile
225                 230                 235                 240

Phe His Pro Ala Ser Val Gly Lys Lys Ala Asp Glu Val Leu Phe Leu
                245                 250                 255

Gln Gly Ser Lys Ala Tyr Leu Gln Asn Lys Gly Phe Asp Val Asp Lys
            260                 265                 270

Asp Gly Lys Ile Thr Leu Gly Glu Ile Ser Ser Thr Leu Tyr Thr Thr
        275                 280                 285

Tyr Tyr Lys Gly Leu Leu Pro Glu Asn Arg His Val Ile Ser Tyr
    290                 295                 300

<210> SEQ ID NO 40
<211> LENGTH: 314
```

```
<212> TYPE: PRT
<213> ORGANISM: unknown
<220> FEATURE:
<223> OTHER INFORMATION: (POLY)2-gp188

<400> SEQUENCE: 40

Met Gly Ser Lys Arg Lys Lys Arg Lys Lys Arg Lys Ser Lys Arg
1               5                   10                  15

Lys Lys Arg Lys Lys Arg Lys Asn Phe Arg Thr Lys Asn Gly Tyr Arg
            20                  25                  30

Asp Leu Gln Ala Leu Val Lys Glu Leu Gly Leu Tyr Thr Gly Gln Ile
                35                  40                  45

Asp Gly Val Trp Gly Lys Gly Thr Ser Ser Thr Glu Thr Leu Leu
    50                  55                  60

Arg Gly Tyr Ala Glu Val Val Gly Lys Asn Thr Gly Ile Gly Leu
65                  70                  75                  80

Pro Thr Thr Ser Asp Ala Ser Gly Tyr Asn Val Ile Thr Ala Leu Gln
                85                  90                  95

Arg Asn Leu Ala Phe Leu Gly Leu Tyr Ser Leu Thr Val Asp Gly Ile
                100                 105                 110

Trp Gly Asn Gly Thr Leu Ser Gly Leu Asp Lys Ala Phe Glu Val Tyr
            115                 120                 125

Lys Glu Arg Tyr Arg Thr Pro Thr Tyr Asp Ile Ala Trp Ser Gly Lys
130                 135                 140

Val Ser Pro Ala Phe Thr Ala Lys Val Lys Asp Trp Cys Gly Val His
145                 150                 155                 160

Val Pro Asn His Arg Ala Pro His Trp Leu Met Ala Cys Met Ala Phe
                165                 170                 175

Glu Thr Gly Gln Thr Phe Ser Pro Ser Ile Lys Asn Ala Ala Gly Ser
            180                 185                 190

Glu Ala Tyr Gly Leu Ile Gln Phe Met Ser Pro Ala Ala Asn Asp Leu
        195                 200                 205

Asn Val Pro Leu Ser Val Ile Arg Ser Met Asp Gln Leu Thr Gln Leu
    210                 215                 220

Asp Leu Val Phe Lys Tyr Phe Glu Met Trp Met Lys Arg Gly Lys Arg
225                 230                 235                 240

Tyr Thr Gln Leu Glu Asp Phe Tyr Leu Thr Ile Phe His Pro Ala Ser
                245                 250                 255

Val Gly Lys Lys Ala Asp Glu Val Leu Phe Leu Gln Gly Ser Lys Ala
            260                 265                 270

Tyr Leu Gln Asn Lys Gly Phe Asp Val Asp Lys Asp Gly Lys Ile Thr
        275                 280                 285

Leu Gly Glu Ile Ser Ser Thr Leu Tyr Thr Thr Tyr Tyr Lys Gly Leu
    290                 295                 300

Leu Pro Glu Asn Arg His Val Ile Ser Tyr
305                 310

<210> SEQ ID NO 41
<211> LENGTH: 325
<212> TYPE: PRT
<213> ORGANISM: unknown
<220> FEATURE:
<223> OTHER INFORMATION: (POLY)3-gp188

<400> SEQUENCE: 41

Met Gly Ser Lys Arg Lys Lys Arg Lys Lys Arg Lys Ser Lys Arg
1               5                   10                  15
```

```
Lys Lys Arg Lys Lys Arg Lys Arg Ser Lys Arg Lys Lys Arg Lys Lys
                20                  25                  30

Arg Lys Asn Phe Arg Thr Lys Asn Gly Tyr Arg Asp Leu Gln Ala Leu
            35                  40                  45

Val Lys Glu Leu Gly Leu Tyr Thr Gly Gln Ile Asp Gly Val Trp Gly
 50                  55                  60

Lys Gly Thr Ser Ser Thr Glu Thr Leu Leu Arg Gly Tyr Ala Glu
 65                  70                  75                  80

Val Val Gly Lys Asn Thr Gly Gly Ile Gly Leu Pro Thr Thr Ser Asp
                 85                  90                  95

Ala Ser Gly Tyr Asn Val Ile Thr Ala Leu Gln Arg Asn Leu Ala Phe
                100                 105                 110

Leu Gly Leu Tyr Ser Leu Thr Val Asp Gly Ile Trp Gly Asn Gly Thr
            115                 120                 125

Leu Ser Gly Leu Asp Lys Ala Phe Glu Val Tyr Lys Glu Arg Tyr Arg
130                 135                 140

Thr Pro Thr Tyr Asp Ile Ala Trp Ser Gly Lys Val Ser Pro Ala Phe
145                 150                 155                 160

Thr Ala Lys Val Lys Asp Trp Cys Gly Val His Val Pro Asn His Arg
                165                 170                 175

Ala Pro His Trp Leu Met Ala Cys Met Ala Phe Glu Thr Gly Gln Thr
            180                 185                 190

Phe Ser Pro Ser Ile Lys Asn Ala Ala Gly Ser Glu Ala Tyr Gly Leu
        195                 200                 205

Ile Gln Phe Met Ser Pro Ala Ala Asn Asp Leu Asn Val Pro Leu Ser
    210                 215                 220

Val Ile Arg Ser Met Asp Gln Leu Thr Gln Leu Asp Leu Val Phe Lys
225                 230                 235                 240

Tyr Phe Glu Met Trp Met Lys Arg Gly Lys Arg Tyr Thr Gln Leu Glu
                245                 250                 255

Asp Phe Tyr Leu Thr Ile Phe His Pro Ala Ser Val Gly Lys Lys Ala
            260                 265                 270

Asp Glu Val Leu Phe Leu Gln Gly Ser Lys Ala Tyr Leu Gln Asn Lys
        275                 280                 285

Gly Phe Asp Val Asp Lys Asp Gly Lys Ile Thr Leu Gly Glu Ile Ser
    290                 295                 300

Ser Thr Leu Tyr Thr Thr Tyr Tyr Lys Gly Leu Leu Pro Glu Asn Arg
305                 310                 315                 320

His Val Ile Ser Tyr
                325

<210> SEQ ID NO 42
<211> LENGTH: 336
<212> TYPE: PRT
<213> ORGANISM: unknown
<220> FEATURE:
<223> OTHER INFORMATION: (POLY)4-gp188

<400> SEQUENCE: 42

Met Gly Ser Lys Arg Lys Lys Arg Lys Lys Arg Lys Arg Ser Lys Arg
1               5                   10                  15

Lys Lys Arg Lys Lys Arg Lys Arg Ser Lys Arg Lys Lys Arg Lys Lys
                20                  25                  30

Arg Lys Arg Ser Lys Arg Lys Lys Arg Lys Lys Arg Lys Asn Phe Arg
            35                  40                  45
```

```
Thr Lys Asn Gly Tyr Arg Asp Leu Gln Ala Leu Val Lys Glu Leu Gly
     50                  55                  60

Leu Tyr Thr Gly Gln Ile Asp Gly Val Trp Lys Gly Thr Ser Ser
 65                  70                  75                  80

Ser Thr Glu Thr Leu Leu Arg Gly Tyr Ala Glu Val Val Gly Lys Asn
                 85                  90                  95

Thr Gly Gly Ile Gly Leu Pro Thr Thr Ser Asp Ala Ser Gly Tyr Asn
            100                 105                 110

Val Ile Thr Ala Leu Gln Arg Asn Leu Ala Phe Leu Gly Leu Tyr Ser
        115                 120                 125

Leu Thr Val Asp Gly Ile Trp Gly Asn Gly Thr Leu Ser Gly Leu Asp
    130                 135                 140

Lys Ala Phe Glu Val Tyr Lys Glu Arg Tyr Arg Thr Pro Thr Tyr Asp
145                 150                 155                 160

Ile Ala Trp Ser Gly Lys Val Ser Pro Ala Phe Thr Ala Lys Val Lys
                165                 170                 175

Asp Trp Cys Gly Val His Val Pro Asn His Arg Ala Pro His Trp Leu
            180                 185                 190

Met Ala Cys Met Ala Phe Glu Thr Gly Gln Thr Phe Ser Pro Ser Ile
        195                 200                 205

Lys Asn Ala Ala Gly Ser Glu Ala Tyr Gly Leu Ile Gln Phe Met Ser
    210                 215                 220

Pro Ala Ala Asn Asp Leu Asn Val Pro Leu Ser Val Ile Arg Ser Met
225                 230                 235                 240

Asp Gln Leu Thr Gln Leu Asp Leu Val Phe Lys Tyr Phe Glu Met Trp
                245                 250                 255

Met Lys Arg Gly Lys Arg Tyr Thr Gln Leu Glu Asp Phe Tyr Leu Thr
            260                 265                 270

Ile Phe His Pro Ala Ser Val Gly Lys Lys Ala Asp Glu Val Leu Phe
        275                 280                 285

Leu Gln Gly Ser Lys Ala Tyr Leu Gln Asn Lys Gly Phe Asp Val Asp
    290                 295                 300

Lys Asp Gly Lys Ile Thr Leu Gly Glu Ile Ser Ser Thr Leu Tyr Thr
305                 310                 315                 320

Thr Tyr Tyr Lys Gly Leu Leu Pro Glu Asn Arg His Val Ile Ser Tyr
                325                 330                 335

<210> SEQ ID NO 43
<211> LENGTH: 272
<212> TYPE: PRT
<213> ORGANISM: unknown
<220> FEATURE:
<223> OTHER INFORMATION: pKKZ144pET32b

<400> SEQUENCE: 43

Ala Met Gly Ser Lys Arg Lys Lys Arg Lys Lys Arg Lys Lys Val Leu
  1               5                  10                  15

Arg Lys Gly Asp Arg Gly Asp Glu Val Cys Gln Leu Gln Thr Leu Leu
                 20                  25                  30

Asn Leu Cys Gly Tyr Asp Val Gly Lys Pro Asp Gly Ile Phe Gly Asn
             35                  40                  45

Asn Thr Phe Asn Gln Val Val Lys Phe Gln Lys Asp Asn Cys Leu Asp
         50                  55                  60

Ser Asp Gly Ile Val Gly Lys Asn Thr Trp Ala Glu Leu Phe Ser Lys
 65                  70                  75                  80
```

```
Tyr Ser Pro Pro Ile Pro Tyr Lys Thr Ile Pro Met Pro Thr Ala Asn
                85                  90                  95

Lys Ser Arg Ala Ala Thr Pro Val Met Asn Ala Val Glu Asn Ala
            100                 105                 110

Thr Gly Val Arg Ser Gln Leu Leu Leu Thr Phe Ala Ser Ile Glu Ser
        115                 120                 125

Ala Phe Asp Tyr Glu Ile Lys Ala Lys Thr Ser Ser Ala Thr Gly Trp
    130                 135                 140

Phe Gln Phe Leu Thr Gly Thr Trp Lys Thr Met Ile Glu Asn Tyr Gly
145                 150                 155                 160

Met Lys Tyr Gly Val Leu Thr Asp Pro Thr Gly Ala Leu Arg Lys Asp
                165                 170                 175

Pro Arg Ile Ser Ala Leu Met Gly Ala Glu Leu Ile Lys Glu Asn Met
            180                 185                 190

Asn Ile Leu Arg Pro Val Leu Lys Arg Glu Pro Thr Asp Thr Asp Leu
        195                 200                 205

Tyr Leu Ala His Phe Phe Gly Pro Gly Ala Ala Arg Arg Phe Leu Thr
    210                 215                 220

Thr Gly Gln Asn Glu Leu Ala Ala Thr His Phe Pro Lys Glu Ala Gln
225                 230                 235                 240

Ala Asn Pro Ser Ile Phe Tyr Asn Lys Asp Gly Ser Pro Lys Thr Ile
                245                 250                 255

Gln Glu Val Tyr Asn Leu Met Asp Gly Lys Val Ala Ala His Arg Lys
            260                 265                 270

<210> SEQ ID NO 44
<211> LENGTH: 269
<212> TYPE: PRT
<213> ORGANISM: unknown
<220> FEATURE:
<223> OTHER INFORMATION: KRK_6_pET32b

<400> SEQUENCE: 44

Ala Met Gly Ser Lys Arg Lys Arg Lys Lys Val Leu Arg Lys Gly
1               5                   10                  15

Asp Arg Gly Asp Glu Val Cys Gln Leu Gln Thr Leu Leu Asn Leu Cys
            20                  25                  30

Gly Tyr Asp Val Gly Lys Pro Asp Gly Ile Phe Gly Asn Asn Thr Phe
        35                  40                  45

Asn Gln Val Val Lys Phe Gln Lys Asp Asn Cys Leu Asp Ser Asp Gly
    50                  55                  60

Ile Val Gly Lys Asn Thr Trp Ala Glu Leu Phe Ser Lys Tyr Ser Pro
65                  70                  75                  80

Pro Ile Pro Tyr Lys Thr Ile Pro Met Pro Thr Ala Asn Lys Ser Arg
                85                  90                  95

Ala Ala Ala Thr Pro Val Met Asn Ala Val Glu Asn Ala Thr Gly Val
            100                 105                 110

Arg Ser Gln Leu Leu Leu Thr Phe Ala Ser Ile Glu Ser Ala Phe Asp
        115                 120                 125

Tyr Glu Ile Lys Ala Lys Thr Ser Ser Ala Thr Gly Trp Phe Gln Phe
    130                 135                 140

Leu Thr Gly Thr Trp Lys Thr Met Ile Glu Asn Tyr Gly Met Lys Tyr
145                 150                 155                 160

Gly Val Leu Thr Asp Pro Thr Gly Ala Leu Arg Lys Asp Pro Arg Ile
                165                 170                 175
```

```
Ser Ala Leu Met Gly Ala Glu Leu Ile Lys Glu Asn Met Asn Ile Leu
            180                 185                 190

Arg Pro Val Leu Lys Arg Glu Pro Thr Asp Thr Asp Leu Tyr Leu Ala
            195                 200                 205

His Phe Phe Gly Pro Gly Ala Ala Arg Arg Phe Leu Thr Thr Gly Gln
            210                 215                 220

Asn Glu Leu Ala Ala Thr His Phe Pro Lys Glu Ala Gln Ala Asn Pro
225                 230                 235                 240

Ser Ile Phe Tyr Asn Lys Asp Gly Ser Pro Lys Thr Ile Gln Glu Val
            245                 250                 255

Tyr Asn Leu Met Asp Gly Lys Val Ala Ala His Arg Lys
            260                 265

<210> SEQ ID NO 45
<211> LENGTH: 275
<212> TYPE: PRT
<213> ORGANISM: unknown
<220> FEATURE:
<223> OTHER INFORMATION: KRK_12_pET32b

<400> SEQUENCE: 45

Ala Met Gly Ser Lys Arg Lys Arg Lys Arg Lys Lys Arg Lys
1               5                   10                  15

Lys Val Leu Arg Lys Gly Asp Arg Gly Asp Glu Val Cys Gln Leu Gln
            20                  25                  30

Thr Leu Leu Asn Leu Cys Gly Tyr Asp Val Gly Lys Pro Asp Gly Ile
            35                  40                  45

Phe Gly Asn Asn Thr Phe Asn Gln Val Val Lys Phe Gln Lys Asp Asn
50                  55                  60

Cys Leu Asp Ser Asp Gly Ile Val Gly Lys Asn Thr Trp Ala Glu Leu
65                  70                  75                  80

Phe Ser Lys Tyr Ser Pro Pro Ile Pro Tyr Lys Thr Ile Pro Met Pro
                85                  90                  95

Thr Ala Asn Lys Ser Arg Ala Ala Ala Thr Pro Val Met Asn Ala Val
            100                 105                 110

Glu Asn Ala Thr Gly Val Arg Ser Gln Leu Leu Thr Phe Ala Ser
            115                 120                 125

Ile Glu Ser Ala Phe Asp Tyr Glu Ile Lys Ala Lys Thr Ser Ser Ala
            130                 135                 140

Thr Gly Trp Phe Gln Phe Leu Thr Gly Thr Trp Lys Thr Met Ile Glu
145                 150                 155                 160

Asn Tyr Gly Met Lys Tyr Gly Val Leu Thr Asp Pro Thr Gly Ala Leu
                165                 170                 175

Arg Lys Asp Pro Arg Ile Ser Ala Leu Met Gly Ala Glu Leu Ile Lys
            180                 185                 190

Glu Asn Met Asn Ile Leu Arg Pro Val Leu Lys Arg Glu Pro Thr Asp
            195                 200                 205

Thr Asp Leu Tyr Leu Ala His Phe Gly Pro Gly Ala Ala Arg Arg
            210                 215                 220

Phe Leu Thr Thr Gly Gln Asn Glu Leu Ala Ala Thr His Phe Pro Lys
225                 230                 235                 240

Glu Ala Gln Ala Asn Pro Ser Ile Phe Tyr Asn Lys Asp Gly Ser Pro
                245                 250                 255

Lys Thr Ile Gln Glu Val Tyr Asn Leu Met Asp Gly Lys Val Ala Ala
            260                 265                 270
```

<210> SEQ ID NO 46
<211> LENGTH: 277
<212> TYPE: PRT
<213> ORGANISM: unknown
<220> FEATURE:
<223> OTHER INFORMATION: KRK_14_pET32b

<400> SEQUENCE: 46

Ala Met Gly Ser Lys Arg Lys Arg Lys Lys Arg Lys Lys Arg Lys
1               5                   10                  15

Lys Arg Lys Val Leu Arg Lys Gly Asp Arg Gly Asp Glu Val Cys Gln
            20                  25                  30

Leu Gln Thr Leu Leu Asn Leu Cys Gly Tyr Asp Val Gly Lys Pro Asp
        35                  40                  45

Gly Ile Phe Gly Asn Asn Thr Phe Asn Gln Val Val Lys Phe Gln Lys
    50                  55                  60

Asp Asn Cys Leu Asp Ser Asp Gly Ile Val Gly Lys Asn Thr Trp Ala
65                  70                  75                  80

Glu Leu Phe Ser Lys Tyr Ser Pro Pro Ile Pro Tyr Lys Thr Ile Pro
                85                  90                  95

Met Pro Thr Ala Asn Lys Ser Arg Ala Ala Thr Pro Val Met Asn
            100                 105                 110

Ala Val Glu Asn Ala Thr Gly Val Arg Ser Gln Leu Leu Leu Thr Phe
        115                 120                 125

Ala Ser Ile Glu Ser Ala Phe Asp Tyr Glu Ile Lys Ala Lys Thr Ser
    130                 135                 140

Ser Ala Thr Gly Trp Phe Gln Phe Leu Thr Gly Thr Trp Lys Thr Met
145                 150                 155                 160

Ile Glu Asn Tyr Gly Met Lys Tyr Gly Val Leu Thr Asp Pro Thr Gly
                165                 170                 175

Ala Leu Arg Lys Asp Pro Arg Ile Ser Ala Leu Met Gly Ala Glu Leu
            180                 185                 190

Ile Lys Glu Asn Met Asn Ile Leu Arg Pro Val Leu Lys Arg Glu Pro
        195                 200                 205

Thr Asp Thr Asp Leu Tyr Leu Ala His Phe Phe Gly Pro Gly Ala Ala
    210                 215                 220

Arg Arg Phe Leu Thr Thr Gly Gln Asn Glu Leu Ala Ala Thr His Phe
225                 230                 235                 240

Pro Lys Glu Ala Gln Ala Asn Pro Ser Ile Phe Tyr Asn Lys Asp Gly
                245                 250                 255

Ser Pro Lys Thr Ile Gln Glu Val Tyr Asn Leu Met Asp Gly Lys Val
            260                 265                 270

Ala Ala His Arg Lys
        275

<210> SEQ ID NO 47
<211> LENGTH: 272
<212> TYPE: PRT
<213> ORGANISM: unknown
<220> FEATURE:
<223> OTHER INFORMATION: R9_pET32b

<400> SEQUENCE: 47

Ala Met Gly Ser Arg Arg Arg Arg Arg Arg Arg Arg Arg Lys Val Leu

```
  1               5                  10                 15
Arg Lys Gly Asp Arg Gly Asp Glu Val Cys Gln Leu Gln Thr Leu Leu
                20                  25                 30
Asn Leu Cys Gly Tyr Asp Val Gly Lys Pro Asp Gly Ile Phe Gly Asn
                35                  40                 45
Asn Thr Phe Asn Gln Val Val Lys Phe Gln Lys Asp Asn Cys Leu Asp
                50                  55              60
Ser Asp Gly Ile Val Gly Lys Asn Thr Trp Ala Glu Leu Phe Ser Lys
 65                 70                75                     80
Tyr Ser Pro Pro Ile Pro Tyr Lys Thr Ile Pro Met Pro Thr Ala Asn
                    85                  90                 95
Lys Ser Arg Ala Ala Ala Thr Pro Val Met Asn Ala Val Glu Asn Ala
                100                 105               110
Thr Gly Val Arg Ser Gln Leu Leu Leu Thr Phe Ala Ser Ile Glu Ser
                115                 120                125
Ala Phe Asp Tyr Glu Ile Lys Ala Lys Thr Ser Ser Ala Thr Gly Trp
130                 135                 140
Phe Gln Phe Leu Thr Gly Thr Trp Lys Thr Met Ile Glu Asn Tyr Gly
145                 150                 155                 160
Met Lys Tyr Gly Val Leu Thr Asp Pro Thr Gly Ala Leu Arg Lys Asp
                    165                 170                 175
Pro Arg Ile Ser Ala Leu Met Gly Ala Glu Leu Ile Lys Glu Asn Met
                180                 185                 190
Asn Ile Leu Arg Pro Val Leu Arg Glu Pro Thr Asp Thr Asp Leu
                195                 200                 205
Tyr Leu Ala His Phe Phe Gly Pro Gly Ala Ala Arg Arg Phe Leu Thr
210                 215                 220
Thr Gly Gln Asn Glu Leu Ala Ala Thr His Phe Pro Lys Glu Ala Gln
225                 230                 235                 240
Ala Asn Pro Ser Ile Phe Tyr Asn Lys Asp Gly Ser Pro Lys Thr Ile
                    245                 250                 255
Gln Glu Val Tyr Asn Leu Met Asp Gly Lys Val Ala Ala His Arg Lys
                260                 265                 270

<210> SEQ ID NO 48
<211> LENGTH: 271
<212> TYPE: PRT
<213> ORGANISM: unknown
<220> FEATURE:
<223> OTHER INFORMATION: K8_pET32b

<400> SEQUENCE: 48

Ala Met Gly Ser Lys Lys Lys Lys Lys Lys Lys Lys Val Leu Arg
 1               5                  10                 15

Lys Gly Asp Arg Gly Asp Glu Val Cys Gln Leu Gln Thr Leu Leu Asn
                20                  25                 30

Leu Cys Gly Tyr Asp Val Gly Lys Pro Asp Gly Ile Phe Gly Asn Asn
                35                  40                 45

Thr Phe Asn Gln Val Val Lys Phe Gln Lys Asp Asn Cys Leu Asp Ser
                50                  55              60

Asp Gly Ile Val Gly Lys Asn Thr Trp Ala Glu Leu Phe Ser Lys Tyr
 65                 70                75                     80

Ser Pro Pro Ile Pro Tyr Lys Thr Ile Pro Met Pro Thr Ala Asn Lys
                    85                  90                 95

Ser Arg Ala Ala Ala Thr Pro Val Met Asn Ala Val Glu Asn Ala Thr
```

```
            100                 105                 110
Gly Val Arg Ser Gln Leu Leu Leu Thr Phe Ala Ser Ile Glu Ser Ala
            115                 120                 125

Phe Asp Tyr Glu Ile Lys Ala Lys Thr Ser Ser Ala Thr Gly Trp Phe
        130                 135                 140

Gln Phe Leu Thr Gly Thr Trp Lys Thr Met Ile Glu Asn Tyr Gly Met
145                 150                 155                 160

Lys Tyr Gly Val Leu Thr Asp Pro Thr Gly Ala Leu Arg Lys Asp Pro
                165                 170                 175

Arg Ile Ser Ala Leu Met Gly Ala Glu Leu Ile Lys Glu Asn Met Asn
            180                 185                 190

Ile Leu Arg Pro Val Leu Lys Arg Glu Pro Thr Asp Thr Asp Leu Tyr
        195                 200                 205

Leu Ala His Phe Phe Gly Pro Gly Ala Ala Arg Arg Phe Leu Thr Thr
        210                 215                 220

Gly Gln Asn Glu Leu Ala Ala Thr His Phe Pro Lys Glu Ala Gln Ala
225                 230                 235                 240

Asn Pro Ser Ile Phe Tyr Asn Lys Asp Gly Ser Pro Lys Thr Ile Gln
                245                 250                 255

Glu Val Tyr Asn Leu Met Asp Gly Lys Val Ala Ala His Arg Lys
            260                 265                 270

<210> SEQ ID NO 49
<211> LENGTH: 302
<212> TYPE: PRT
<213> ORGANISM: unknown
<220> FEATURE:
<223> OTHER INFORMATION: pK2KZ144_pET32b_mod3

<400> SEQUENCE: 49

Ala Met Gly Ser Lys Arg Lys Lys Arg Lys Lys Arg Lys Arg Gly Ser
1               5                   10                  15

Gly Ser Gly Lys Arg Lys Lys Arg Lys Lys Arg Lys Arg Gly Ser Gly
            20                  25                  30

Ser Gly Lys Arg Lys Lys Arg Lys Lys Arg Lys Lys Val Leu Arg Lys
        35                  40                  45

Gly Asp Arg Gly Asp Glu Val Cys Gln Leu Gln Thr Leu Leu Asn Leu
    50                  55                  60

Cys Gly Tyr Asp Val Gly Lys Pro Asp Gly Ile Phe Gly Asn Asn Thr
65                  70                  75                  80

Phe Asn Gln Val Val Lys Phe Gln Lys Asp Asn Cys Leu Asp Ser Asp
                85                  90                  95

Gly Ile Val Gly Lys Asn Thr Trp Ala Glu Leu Phe Ser Lys Tyr Ser
            100                 105                 110

Pro Pro Ile Pro Tyr Lys Thr Ile Pro Met Pro Thr Ala Asn Lys Ser
        115                 120                 125

Arg Ala Ala Ala Thr Pro Val Met Asn Ala Val Glu Asn Ala Thr Gly
    130                 135                 140

Val Arg Ser Gln Leu Leu Leu Thr Phe Ala Ser Ile Glu Ser Ala Phe
145                 150                 155                 160

Asp Tyr Glu Ile Lys Ala Lys Thr Ser Ser Ala Thr Gly Trp Phe Gln
                165                 170                 175

Phe Leu Thr Gly Thr Trp Lys Thr Met Ile Glu Asn Tyr Gly Met Lys
            180                 185                 190

Tyr Gly Val Leu Thr Asp Pro Thr Gly Ala Leu Arg Lys Asp Pro Arg
```

```
            195                 200                 205
Ile Ser Ala Leu Met Gly Ala Glu Leu Ile Lys Glu Asn Met Asn Ile
    210                 215                 220

Leu Arg Pro Val Leu Lys Arg Glu Pro Thr Asp Thr Asp Leu Tyr Leu
225                 230                 235                 240

Ala His Phe Phe Gly Pro Gly Ala Ala Arg Arg Phe Leu Thr Thr Gly
                245                 250                 255

Gln Asn Glu Leu Ala Ala Thr His Phe Pro Lys Glu Ala Gln Ala Asn
            260                 265                 270

Pro Ser Ile Phe Tyr Asn Lys Asp Gly Ser Pro Lys Thr Ile Gln Glu
                275                 280                 285

Val Tyr Asn Leu Met Asp Gly Lys Val Ala Ala His Arg Lys
            290                 295                 300

<210> SEQ ID NO 50
<211> LENGTH: 30
<212> TYPE: DNA
<213> ORGANISM: artificial sequence
<220> FEATURE:
<223> OTHER INFORMATION: primer PSP3gp10 forw r

<400> SEQUENCE: 50
atgggatccc cggtcattaa tactcaccag                                    30

<210> SEQ ID NO 51
<211> LENGTH: 22
<212> TYPE: DNA
<213> ORGANISM: artificial sequence
<220> FEATURE:
<223> OTHER INFORMATION: primer PSP3gp10 rev

<400> SEQUENCE: 51
tgccatcacc ccgccagccg tg                                            22

<210> SEQ ID NO 52
<211> LENGTH: 57
<212> TYPE: DNA
<213> ORGANISM: artificial sequence
<220> FEATURE:
<223> OTHER INFORMATION: primer PKPSP3gp10 forw

<400> SEQUENCE: 52
atgggatcca aacgcaagaa acgtaagaaa cgcaaaccgg tcattaatac tcaccag      57

<210> SEQ ID NO 53
<211> LENGTH: 176
<212> TYPE: PRT
<213> ORGANISM: unknown
<220> FEATURE:
<223> OTHER INFORMATION: PKPSP3gp10

<400> SEQUENCE: 53

Met Gly Ser Lys Arg Lys Lys Arg Lys Lys Arg Lys Pro Val Ile Asn
1               5                   10                  15

Thr His Gln Asn Ile Ala Ala Phe Leu Asp Met Leu Ala Tyr Ser Glu
            20                  25                  30

Gly Thr Ala Asn His Pro Leu Thr Lys Asn Arg Gly Tyr Asp Val Ile
        35                  40                  45

Val Thr Gly Phe Asp Gly Ser Pro Glu Ile Phe Thr Asp Tyr Ser Asp
    50                  55                  60

His Pro Phe Ala His Gly Arg Pro Pro Lys Val Phe Asn Arg Arg Gly
```

```
                65                  70                  75                  80
Glu Lys Ser Thr Ala Ser Gly Arg Tyr Gln Gln Leu Tyr Ile Phe Trp
                    85                  90                  95

Pro His Tyr Lys Lys Gln Leu Ala Leu Pro Asp Phe Ser Pro Leu Ser
                    100                 105                 110

Gln Asp Lys Leu Ala Ile Gln Leu Ile Arg Glu Arg Gly Ala Ile Asp
                    115                 120                 125

Asp Ile Arg Ala Gly Arg Ile Glu Arg Ala Val Ser Arg Cys Arg Asn
                130                 135                 140

Ile Trp Ala Ser Leu Pro Gly Ala Gly Tyr Gly Gln Arg Glu His Ser
145                 150                 155                 160

Leu Glu Lys Leu Val Thr Val Trp Arg Thr Ala Gly Val Met Ala
                    165                 170                 175

<210> SEQ ID NO 54
<211> LENGTH: 28
<212> TYPE: DNA
<213> ORGANISM: artificial sequence
<220> FEATURE:
<223> OTHER INFORMATION: primer SP2gp09 forw

<400> SEQUENCE: 54
atgggatccc cggtaattaa cacgcatc                                        28

<210> SEQ ID NO 55
<211> LENGTH: 25
<212> TYPE: DNA
<213> ORGANISM: artificial sequence
<220> FEATURE:
<223> OTHER INFORMATION: primer P2gp09 rev

<400> SEQUENCE: 55
agccggtacg ccgccagcgg tacgc                                           25

<210> SEQ ID NO 56
<211> LENGTH: 54
<212> TYPE: DNA
<213> ORGANISM: artificial sequence
<220> FEATURE:
<223> OTHER INFORMATION: primer PKP2gp09 forw

<400> SEQUENCE: 56
atgggatcca aacgcaagaa acgtaagaaa cgcaaaccgg taattaacac gcat          54

<210> SEQ ID NO 57
<211> LENGTH: 176
<212> TYPE: PRT
<213> ORGANISM: unknown
<220> FEATURE:
<223> OTHER INFORMATION: PKP2gp09

<400> SEQUENCE: 57

Met Gly Ser Lys Arg Lys Lys Arg Lys Lys Arg Lys Pro Val Ile Asn
1               5                   10                  15

Thr His Gln Asn Ile Ala Ala Phe Leu Asp Met Leu Ala Val Ser Glu
                20                  25                  30

Gly Thr Ala Asn His Pro Leu Thr Lys Asn Arg Gly Tyr Asp Val Ile
                35                  40                  45

Val Thr Gly Leu Asp Gly Lys Pro Glu Ile Phe Thr Asp Tyr Ser Asp
            50                  55                  60

His Pro Phe Ala His Gly Arg Pro Ala Lys Val Phe Asn Arg Arg Gly
```

```
                65                  70                  75                  80
Glu Lys Ser Thr Ala Ser Gly Arg Tyr Gln Gln Leu Tyr Leu Phe Trp
                    85                  90                  95

Pro His Tyr Arg Lys Gln Leu Ala Leu Pro Asp Phe Ser Pro Leu Ser
                100                 105                 110

Gln Asp Arg Leu Ala Ile Gln Leu Ile Arg Glu Arg Gly Ala Leu Asp
            115                 120                 125

Asp Ile Arg Ala Gly Arg Ile Glu Arg Ala Ile Ser Arg Cys Arg Asn
        130                 135                 140

Ile Trp Ala Ser Leu Pro Gly Ala Gly Tyr Gly Gln Arg Glu His Ser
145                 150                 155                 160

Leu Glu Lys Leu Val Thr Val Trp Arg Thr Ala Gly Val Pro Ala
                165                 170                 175

<210> SEQ ID NO 58
<211> LENGTH: 21
<212> TYPE: DNA
<213> ORGANISM: artificial sequence
<220> FEATURE:
<223> OTHER INFORMATION: primer OBPgpLYS forward

<400> SEQUENCE: 58
atgaaaaata gcgagaagaa t                                              21

<210> SEQ ID NO 59
<211> LENGTH: 24
<212> TYPE: DNA
<213> ORGANISM: artificial sequence
<220> FEATURE:
<223> OTHER INFORMATION: primer OBPgpLYS reverse

<400> SEQUENCE: 59
aactattccg agtgctttct ttgt                                           24

<210> SEQ ID NO 60
<211> LENGTH: 54
<212> TYPE: DNA
<213> ORGANISM: artificial sequence
<220> FEATURE:
<223> OTHER INFORMATION: primer PKOBPgpLYS forward

<400> SEQUENCE: 60
atgggatcca aacgcaagaa acgtaagaaa cgcaaaaaaa atagcgagaa gaat          54

<210> SEQ ID NO 61
<211> LENGTH: 339
<212> TYPE: PRT
<213> ORGANISM: unknown
<220> FEATURE:
<223> OTHER INFORMATION: PKOBPgpLYS

<400> SEQUENCE: 61

Met Gly Ser Lys Arg Lys Lys Arg Lys Lys Arg Lys Lys Asn Ser Glu
1               5                   10                  15

Lys Asn Ala Ser Ile Ile Met Ser Ile Gln Arg Thr Leu Ala Ser Leu
            20                  25                  30

Ser Leu Tyr Gly Gly Arg Ile Asp Gly Leu Phe Gly Lys Cys Arg
        35                  40                  45

Gly Ala Ile Ile Leu Met Leu Asn Lys Val Tyr Pro Asn Phe Ser Thr
    50                  55                  60

Asn Lys Leu Pro Ser Asn Thr Tyr Glu Ala Glu Ser Val Phe Thr Phe
```

```
                65                  70                  75                  80
Leu Gln Thr Ala Leu Ala Gly Val Gly Leu Tyr Thr Ile Thr Ile Asp
                85                  90                  95
Gly Lys Trp Gly Gly Thr Ser Gln Gly Ala Ile Asp Ala Leu Val Lys
                100                 105                 110
Ser Tyr Arg Gln Ile Thr Glu Ala Glu Arg Ala Gly Ser Thr Leu Pro
                115                 120                 125
Leu Gly Leu Ala Thr Val Met Ser Lys His Met Ser Ile Glu Gln Leu
130                 135                 140
Arg Ala Met Leu Pro Thr Asp Arg Gln Gly Tyr Ala Glu Val Tyr Ile
145                 150                 155                 160
Asp Pro Leu Asn Glu Thr Met Asp Ile Phe Glu Ile Asn Thr Pro Leu
                165                 170                 175
Arg Ile Ala His Phe Met Ala Gln Ile Leu His Glu Thr Ala Cys Phe
                180                 185                 190
Lys Tyr Thr Glu Glu Leu Ala Ser Gly Lys Ala Tyr Glu Gly Arg Ala
                195                 200                 205
Asp Leu Gly Asn Thr Arg Pro Gly Asp Gly Pro Leu Phe Lys Gly Arg
210                 215                 220
Gly Leu Leu Gln Ile Thr Gly Arg Leu Asn Tyr Val Lys Cys Gln Val
225                 230                 235                 240
Tyr Leu Arg Glu Lys Leu Lys Asp Pro Thr Phe Asp Ile Thr Ser Ser
                245                 250                 255
Val Thr Cys Ala Gln Gln Leu Ser Glu Ser Pro Leu Leu Ala Ala Leu
                260                 265                 270
Ala Ser Gly Tyr Phe Trp Arg Phe Ile Lys Pro Lys Leu Asn Glu Thr
                275                 280                 285
Ala Asp Lys Asp Asp Ile Tyr Trp Val Ser Val Tyr Val Asn Gly Tyr
                290                 295                 300
Ala Lys Gln Ala Asn Pro Tyr Tyr Pro Asn Arg Asp Lys Glu Pro Asn
305                 310                 315                 320
His Met Lys Glu Arg Val Gln Met Leu Ala Val Thr Lys Lys Ala Leu
                325                 330                 335
Gly Ile Val

<210> SEQ ID NO 62
<211> LENGTH: 283
<212> TYPE: PRT
<213> ORGANISM: unknown
<220> FEATURE:
<223> OTHER INFORMATION: pK2KZ144pET32b

<400> SEQUENCE: 62

Ala Met Gly Ser Lys Arg Lys Lys Arg Lys Arg Lys Arg Ser Lys
1               5                   10                  15
Arg Lys Lys Arg Lys Lys Arg Lys Lys Val Leu Arg Lys Gly Asp Arg
                20                  25                  30
Gly Asp Glu Val Cys Gln Leu Gln Thr Leu Leu Asn Leu Cys Gly Tyr
                35                  40                  45
Asp Val Gly Lys Pro Asp Gly Ile Phe Gly Asn Asn Thr Phe Asn Gln
50                  55                  60
Val Val Lys Phe Gln Lys Asp Asn Cys Leu Asp Ser Asp Gly Ile Val
65                  70                  75                  80
Gly Lys Asn Thr Trp Ala Glu Leu Phe Ser Lys Tyr Ser Pro Pro Ile
                85                  90                  95
```

```
Pro Tyr Lys Thr Ile Pro Met Pro Thr Ala Asn Lys Ser Arg Ala Ala
            100                 105                 110

Ala Thr Pro Val Met Asn Ala Val Glu Asn Ala Thr Gly Val Arg Ser
        115                 120                 125

Gln Leu Leu Leu Thr Phe Ala Ser Ile Glu Ser Ala Phe Asp Tyr Glu
    130                 135                 140

Ile Lys Ala Lys Thr Ser Ser Ala Thr Gly Trp Phe Gln Phe Leu Thr
145                 150                 155                 160

Gly Thr Trp Lys Thr Met Ile Glu Asn Tyr Gly Met Lys Tyr Gly Val
                165                 170                 175

Leu Thr Asp Pro Thr Gly Ala Leu Arg Lys Asp Pro Arg Ile Ser Ala
            180                 185                 190

Leu Met Gly Ala Glu Leu Ile Lys Glu Asn Met Asn Ile Leu Arg Pro
        195                 200                 205

Val Leu Lys Arg Glu Pro Thr Asp Thr Asp Leu Tyr Leu Ala His Phe
    210                 215                 220

Phe Gly Pro Gly Ala Ala Arg Arg Phe Leu Thr Thr Gly Gln Asn Glu
225                 230                 235                 240

Leu Ala Ala Thr His Phe Pro Lys Glu Ala Gln Ala Asn Pro Ser Ile
                245                 250                 255

Phe Tyr Asn Lys Asp Gly Ser Pro Lys Thr Ile Gln Glu Val Tyr Asn
            260                 265                 270

Leu Met Asp Gly Lys Val Ala Ala His Arg Lys
        275                 280

<210> SEQ ID NO 63
<211> LENGTH: 294
<212> TYPE: PRT
<213> ORGANISM: unknown
<220> FEATURE:
<223> OTHER INFORMATION: pK3KZ144pET32b

<400> SEQUENCE: 63

Ala Met Gly Ser Lys Arg Lys Arg Lys Lys Arg Lys Arg Ser Lys
1               5                   10                  15

Arg Lys Lys Arg Lys Lys Arg Lys Arg Ser Lys Arg Lys Lys Arg Lys
                20                  25                  30

Lys Arg Lys Lys Val Leu Arg Lys Gly Asp Arg Gly Asp Glu Val Cys
                35                  40                  45

Gln Leu Gln Thr Leu Leu Asn Leu Cys Gly Tyr Asp Val Gly Lys Pro
    50                  55                  60

Asp Gly Ile Phe Gly Asn Asn Thr Phe Asn Gln Val Val Lys Phe Gln
65                  70                  75                  80

Lys Asp Asn Cys Leu Asp Ser Asp Gly Ile Val Gly Lys Asn Thr Trp
                85                  90                  95

Ala Glu Leu Phe Ser Lys Tyr Ser Pro Pro Ile Pro Tyr Lys Thr Ile
                100                 105                 110

Pro Met Pro Thr Ala Asn Lys Ser Arg Ala Ala Ala Thr Pro Val Met
        115                 120                 125

Asn Ala Val Glu Asn Ala Thr Gly Val Arg Ser Gln Leu Leu Leu Thr
    130                 135                 140

Phe Ala Ser Ile Glu Ser Ala Phe Asp Tyr Glu Ile Lys Ala Lys Thr
145                 150                 155                 160

Ser Ser Ala Thr Gly Trp Phe Gln Phe Leu Thr Gly Thr Trp Lys Thr
                165                 170                 175
```

```
Met Ile Glu Asn Tyr Gly Met Lys Tyr Gly Val Leu Thr Asp Pro Thr
            180                 185                 190

Gly Ala Leu Arg Lys Asp Pro Arg Ile Ser Ala Leu Met Gly Ala Glu
        195                 200                 205

Leu Ile Lys Glu Asn Met Asn Ile Leu Arg Pro Val Leu Lys Arg Glu
    210                 215                 220

Pro Thr Asp Thr Asp Leu Tyr Leu Ala His Phe Phe Gly Pro Gly Ala
225                 230                 235                 240

Ala Arg Arg Phe Leu Thr Thr Gly Gln Asn Glu Leu Ala Ala Thr His
            245                 250                 255

Phe Pro Lys Glu Ala Gln Ala Asn Pro Ser Ile Phe Tyr Asn Lys Asp
        260                 265                 270

Gly Ser Pro Lys Thr Ile Gln Glu Val Tyr Asn Leu Met Asp Gly Lys
    275                 280                 285

Val Ala Ala His Arg Lys
    290

<210> SEQ ID NO 64
<211> LENGTH: 305
<212> TYPE: PRT
<213> ORGANISM: unknown
<220> FEATURE:
<223> OTHER INFORMATION: pK4KZ144pET32b

<400> SEQUENCE: 64

Ala Met Gly Ser Lys Arg Lys Lys Arg Lys Lys Arg Lys Arg Ser Lys
1               5                   10                  15

Arg Lys Lys Arg Lys Lys Arg Lys Arg Ser Lys Arg Lys Lys Arg Lys
            20                  25                  30

Lys Arg Lys Arg Ser Lys Arg Lys Lys Arg Lys Lys Arg Lys Lys Val
        35                  40                  45

Leu Arg Lys Gly Asp Arg Gly Asp Glu Val Cys Gln Leu Gln Thr Leu
50                  55                  60

Leu Asn Leu Cys Gly Tyr Asp Val Gly Lys Pro Asp Gly Ile Phe Gly
65                  70                  75                  80

Asn Asn Thr Phe Asn Gln Val Val Lys Phe Gln Lys Asp Asn Cys Leu
                85                  90                  95

Asp Ser Asp Gly Ile Val Gly Lys Asn Thr Trp Ala Glu Leu Phe Ser
            100                 105                 110

Lys Tyr Ser Pro Pro Ile Pro Tyr Lys Thr Ile Pro Met Pro Thr Ala
        115                 120                 125

Asn Lys Ser Arg Ala Ala Ala Thr Pro Val Met Asn Ala Val Glu Asn
130                 135                 140

Ala Thr Gly Val Arg Ser Gln Leu Leu Leu Thr Phe Ala Ser Ile Glu
145                 150                 155                 160

Ser Ala Phe Asp Tyr Glu Ile Lys Ala Lys Thr Ser Ser Ala Thr Gly
                165                 170                 175

Trp Phe Gln Phe Leu Thr Gly Thr Trp Lys Thr Met Ile Glu Asn Tyr
            180                 185                 190

Gly Met Lys Tyr Gly Val Leu Thr Asp Pro Thr Gly Ala Leu Arg Lys
        195                 200                 205

Asp Pro Arg Ile Ser Ala Leu Met Gly Ala Glu Leu Ile Lys Glu Asn
    210                 215                 220

Met Asn Ile Leu Arg Pro Val Leu Lys Arg Glu Pro Thr Asp Thr Asp
225                 230                 235                 240
```

```
Leu Tyr Leu Ala His Phe Phe Gly Pro Gly Ala Ala Arg Arg Phe Leu
            245                 250                 255

Thr Thr Gly Gln Asn Glu Leu Ala Ala Thr His Phe Pro Lys Glu Ala
        260                 265                 270

Gln Ala Asn Pro Ser Ile Phe Tyr Asn Lys Asp Gly Ser Pro Lys Thr
        275                 280                 285

Ile Gln Glu Val Tyr Asn Leu Met Asp Gly Lys Val Ala Ala His Arg
    290                 295                 300

Lys
305

<210> SEQ ID NO 65
<211> LENGTH: 18
<212> TYPE: PRT
<213> ORGANISM: artificial sequence
<220> FEATURE:
<223> OTHER INFORMATION: primer gp188 for

<400> SEQUENCE: 65

Ala Thr Gly Ala Ala Cys Thr Thr Cys Cys Gly Gly Ala Cys Gly Ala
1               5                   10                  15

Ala Gly

<210> SEQ ID NO 66
<211> LENGTH: 282
<212> TYPE: PRT
<213> ORGANISM: unknown
<220> FEATURE:
<223> OTHER INFORMATION: KRK_19_pET32b

<400> SEQUENCE: 66

Ala Met Gly Ser Lys Arg Lys Lys Arg Lys Lys Arg Lys
1               5                   10                  15

Lys Arg Lys Lys Arg Lys Lys Lys Val Leu Arg Lys Gly Asp Arg Gly
            20                  25                  30

Asp Glu Val Cys Gln Leu Gln Thr Leu Leu Asn Leu Cys Gly Tyr Asp
        35                  40                  45

Val Gly Lys Pro Asp Gly Ile Phe Gly Asn Asn Thr Phe Asn Gln Val
    50                  55                  60

Val Lys Phe Gln Lys Asp Asn Cys Leu Asp Ser Asp Gly Ile Val Gly
65                  70                  75                  80

Lys Asn Thr Trp Ala Glu Leu Phe Ser Lys Tyr Ser Pro Pro Ile Pro
                85                  90                  95

Tyr Lys Thr Ile Pro Met Pro Thr Ala Asn Lys Ser Arg Ala Ala Ala
            100                 105                 110

Thr Pro Val Met Asn Ala Val Glu Asn Ala Thr Gly Val Arg Ser Gln
        115                 120                 125

Leu Leu Leu Thr Phe Ala Ser Ile Glu Ser Ala Phe Asp Tyr Glu Ile
    130                 135                 140

Lys Ala Lys Thr Ser Ser Ala Thr Gly Trp Phe Gln Phe Leu Thr Gly
145                 150                 155                 160

Thr Trp Lys Thr Met Ile Glu Asn Tyr Gly Met Lys Tyr Gly Val Leu
                165                 170                 175

Thr Asp Pro Thr Gly Ala Leu Arg Lys Asp Pro Arg Ile Ser Ala Leu
            180                 185                 190

Met Gly Ala Glu Leu Ile Lys Glu Asn Met Asn Ile Leu Arg Pro Val
        195                 200                 205
```

Leu Lys Arg Glu Pro Thr Asp Thr Asp Leu Tyr Leu Ala His Phe Phe
    210                 215                 220

Gly Pro Gly Ala Ala Arg Arg Phe Leu Thr Thr Gly Gln Asn Glu Leu
225                 230                 235                 240

Ala Ala Thr His Phe Pro Lys Glu Ala Gln Ala Asn Pro Ser Ile Phe
                245                 250                 255

Tyr Asn Lys Asp Gly Ser Pro Lys Thr Ile Gln Glu Val Tyr Asn Leu
            260                 265                 270

Met Asp Gly Lys Val Ala Ala His Arg Lys
        275                 280

<210> SEQ ID NO 67
<211> LENGTH: 284
<212> TYPE: PRT
<213> ORGANISM: unknown
<220> FEATURE:
<223> OTHER INFORMATION: KRK_21_pET32b

<400> SEQUENCE: 67

Ala Met Gly Ser Lys Arg Lys Arg Lys Arg Lys Arg Lys Arg Lys
1               5                   10                  15

Lys Arg Lys Lys Arg Lys Arg Lys Lys Val Leu Arg Lys Gly Asp
                20                  25                  30

Arg Gly Asp Glu Val Cys Gln Leu Gln Thr Leu Leu Asn Leu Cys Gly
                35                  40                  45

Tyr Asp Val Gly Lys Pro Asp Gly Ile Phe Gly Asn Asn Thr Phe Asn
            50                  55                  60

Gln Val Val Lys Phe Gln Lys Asp Asn Cys Leu Asp Ser Asp Gly Ile
65                  70                  75                  80

Val Gly Lys Asn Thr Trp Ala Glu Leu Phe Ser Lys Tyr Ser Pro Pro
                85                  90                  95

Ile Pro Tyr Lys Thr Ile Pro Met Pro Thr Ala Asn Lys Ser Arg Ala
                100                 105                 110

Ala Ala Thr Pro Val Met Asn Ala Val Glu Asn Ala Thr Gly Val Arg
            115                 120                 125

Ser Gln Leu Leu Leu Thr Phe Ala Ser Ile Glu Ser Ala Phe Asp Tyr
130                 135                 140

Glu Ile Lys Ala Lys Thr Ser Ser Ala Thr Gly Trp Phe Gln Phe Leu
145                 150                 155                 160

Thr Gly Thr Trp Lys Thr Met Ile Glu Asn Tyr Gly Met Lys Tyr Gly
                165                 170                 175

Val Leu Thr Asp Pro Thr Gly Ala Leu Arg Lys Asp Pro Arg Ile Ser
            180                 185                 190

Ala Leu Met Gly Ala Glu Leu Ile Lys Glu Asn Met Asn Ile Leu Arg
            195                 200                 205

Pro Val Leu Lys Arg Glu Pro Thr Asp Thr Asp Leu Tyr Leu Ala His
        210                 215                 220

Phe Phe Gly Pro Gly Ala Ala Arg Arg Phe Leu Thr Thr Gly Gln Asn
225                 230                 235                 240

Glu Leu Ala Ala Thr His Phe Pro Lys Glu Ala Gln Ala Asn Pro Ser
                245                 250                 255

Ile Phe Tyr Asn Lys Asp Gly Ser Pro Lys Thr Ile Gln Glu Val Tyr
            260                 265                 270

Asn Leu Met Asp Gly Lys Val Ala Ala His Arg Lys
        275                 280

<210> SEQ ID NO 68
<211> LENGTH: 288
<212> TYPE: PRT
<213> ORGANISM: unknown
<220> FEATURE:
<223> OTHER INFORMATION: KRK_25_pET32b

<400> SEQUENCE: 68

```
Ala Met Gly Ser Lys Arg Lys Lys Arg Lys Lys Arg Lys Lys Arg Lys
1               5                   10                  15

Lys Arg Lys Lys Arg Lys Lys Arg Lys Lys Arg Lys Lys Lys Val Leu
            20                  25                  30

Arg Lys Gly Asp Arg Gly Asp Glu Val Cys Gln Leu Gln Thr Leu Leu
        35                  40                  45

Asn Leu Cys Gly Tyr Asp Val Gly Lys Pro Asp Gly Ile Phe Gly Asn
    50                  55                  60

Asn Thr Phe Asn Gln Val Val Lys Phe Gln Lys Asp Asn Cys Leu Asp
65                  70                  75                  80

Ser Asp Gly Ile Val Gly Lys Asn Thr Trp Ala Glu Leu Phe Ser Lys
                85                  90                  95

Tyr Ser Pro Pro Ile Pro Tyr Lys Thr Ile Pro Met Pro Thr Ala Asn
            100                 105                 110

Lys Ser Arg Ala Ala Ala Thr Pro Val Met Asn Ala Val Glu Asn Ala
        115                 120                 125

Thr Gly Val Arg Ser Gln Leu Leu Leu Thr Phe Ala Ser Ile Glu Ser
    130                 135                 140

Ala Phe Asp Tyr Glu Ile Lys Ala Lys Thr Ser Ser Ala Thr Gly Trp
145                 150                 155                 160

Phe Gln Phe Leu Thr Gly Thr Trp Lys Thr Met Ile Glu Asn Tyr Gly
                165                 170                 175

Met Lys Tyr Gly Val Leu Thr Asp Pro Thr Gly Ala Leu Arg Lys Asp
            180                 185                 190

Pro Arg Ile Ser Ala Leu Met Gly Ala Glu Leu Ile Lys Glu Asn Met
        195                 200                 205

Asn Ile Leu Arg Pro Val Leu Lys Arg Glu Pro Thr Asp Thr Asp Leu
    210                 215                 220

Tyr Leu Ala His Phe Phe Gly Pro Gly Ala Ala Arg Arg Phe Leu Thr
225                 230                 235                 240

Thr Gly Gln Asn Glu Leu Ala Ala Thr His Phe Pro Lys Glu Ala Gln
                245                 250                 255

Ala Asn Pro Ser Ile Phe Tyr Asn Lys Asp Gly Ser Pro Lys Thr Ile
            260                 265                 270

Gln Glu Val Tyr Asn Leu Met Asp Gly Lys Val Ala Ala His Arg Lys
        275                 280                 285
```

<210> SEQ ID NO 69
<211> LENGTH: 302
<212> TYPE: PRT
<213> ORGANISM: unknown
<220> FEATURE:
<223> OTHER INFORMATION: KRK_39_pET32b

<400> SEQUENCE: 69

```
Ala Met Gly Ser Lys Arg Lys Lys Arg Lys Lys Arg Lys Lys Arg Lys
1               5                   10                  15

Lys Arg Lys Lys Arg Lys Lys Arg Lys Lys Arg Lys Lys Arg Lys Lys
```

-continued

```
                20                  25                  30
Arg Lys Lys Arg Lys Lys Arg Lys Lys Arg Lys Lys Val Leu Arg Lys
             35                  40                  45
Gly Asp Arg Gly Asp Glu Val Cys Gln Leu Gln Thr Leu Leu Asn Leu
 50                  55                  60
Cys Gly Tyr Asp Val Gly Lys Pro Asp Gly Ile Phe Gly Asn Asn Thr
 65                  70                  75                  80
Phe Asn Gln Val Val Lys Phe Gln Lys Asp Asn Cys Leu Asp Ser Asp
                 85                  90                  95
Gly Ile Val Gly Lys Asn Thr Trp Ala Glu Leu Phe Ser Lys Tyr Ser
            100                 105                 110
Pro Pro Ile Pro Tyr Lys Thr Ile Pro Met Pro Thr Ala Asn Lys Ser
            115                 120                 125
Arg Ala Ala Thr Pro Val Met Asn Ala Val Glu Asn Ala Thr Gly
    130                 135                 140
Val Arg Ser Gln Leu Leu Leu Thr Phe Ala Ser Ile Glu Ser Ala Phe
145                 150                 155                 160
Asp Tyr Glu Ile Lys Ala Lys Thr Ser Ser Ala Thr Gly Trp Phe Gln
                165                 170                 175
Phe Leu Thr Gly Thr Trp Lys Thr Met Ile Glu Asn Tyr Gly Met Lys
            180                 185                 190
Tyr Gly Val Leu Thr Asp Pro Thr Gly Ala Leu Arg Lys Asp Pro Arg
            195                 200                 205
Ile Ser Ala Leu Met Gly Ala Glu Leu Ile Lys Glu Asn Met Asn Ile
            210                 215                 220
Leu Arg Pro Val Leu Lys Arg Glu Pro Thr Asp Thr Asp Leu Tyr Leu
225                 230                 235                 240
Ala His Phe Phe Gly Pro Gly Ala Ala Arg Arg Phe Leu Thr Thr Gly
                245                 250                 255
Gln Asn Glu Leu Ala Ala Thr His Phe Pro Lys Glu Ala Gln Ala Asn
            260                 265                 270
Pro Ser Ile Phe Tyr Asn Lys Asp Gly Ser Pro Lys Thr Ile Gln Glu
            275                 280                 285
Val Tyr Asn Leu Met Asp Gly Lys Val Ala Ala His Arg Lys
            290                 295                 300

<210> SEQ ID NO 70
<211> LENGTH: 282
<212> TYPE: PRT
<213> ORGANISM: unknown
<220> FEATURE:
<223> OTHER INFORMATION: K19_pET32b

<400> SEQUENCE: 70

Ala Met Gly Ser Lys Arg Lys Lys Arg Lys Lys Arg Lys Lys Arg Lys
  1               5                  10                  15
Lys Arg Lys Lys Arg Lys Lys Val Leu Arg Lys Gly Asp Arg Gly
             20                  25                  30
Asp Glu Val Cys Gln Leu Gln Thr Leu Leu Asn Leu Cys Gly Tyr Asp
             35                  40                  45
Val Gly Lys Pro Asp Gly Ile Phe Gly Asn Asn Thr Phe Asn Gln Val
         50                  55                  60
Val Lys Phe Gln Lys Asp Asn Cys Leu Asp Ser Asp Gly Ile Val Gly
 65                  70                  75                  80
Lys Asn Thr Trp Ala Glu Leu Phe Ser Lys Tyr Ser Pro Pro Ile Pro
```

```
            85                  90                  95
Tyr Lys Thr Ile Pro Met Pro Thr Ala Asn Lys Ser Arg Ala Ala
                100                 105                 110

Thr Pro Val Met Asn Ala Val Glu Asn Ala Thr Gly Val Arg Ser Gln
            115                 120                 125

Leu Leu Leu Thr Phe Ala Ser Ile Glu Ser Ala Phe Asp Tyr Glu Ile
        130                 135                 140

Lys Ala Lys Thr Ser Ser Ala Thr Gly Trp Phe Gln Phe Leu Thr Gly
145                 150                 155                 160

Thr Trp Lys Thr Met Ile Glu Asn Tyr Gly Met Lys Tyr Gly Val Leu
                165                 170                 175

Thr Asp Pro Thr Gly Ala Leu Arg Lys Asp Pro Arg Ile Ser Ala Leu
            180                 185                 190

Met Gly Ala Glu Leu Ile Lys Glu Asn Met Asn Ile Leu Arg Pro Val
        195                 200                 205

Leu Lys Arg Glu Pro Thr Asp Thr Asp Leu Tyr Leu Ala His Phe Phe
210                 215                 220

Gly Pro Gly Ala Ala Arg Arg Phe Leu Thr Thr Gly Gln Asn Glu Leu
225                 230                 235                 240

Ala Ala Thr His Phe Pro Lys Glu Ala Gln Ala Asn Pro Ser Ile Phe
                245                 250                 255

Tyr Asn Lys Asp Gly Ser Pro Lys Thr Ile Gln Glu Val Tyr Asn Leu
            260                 265                 270

Met Asp Gly Lys Val Ala Ala His Arg Lys
        275                 280

<210> SEQ ID NO 71
<211> LENGTH: 279
<212> TYPE: PRT
<213> ORGANISM: unknown
<220> FEATURE:
<223> OTHER INFORMATION: K16_pET32b

<400> SEQUENCE: 71

Ala Met Gly Ser Lys Lys Lys Lys Lys Lys Lys Lys Lys Lys Lys
1               5                   10                  15

Lys Lys Lys Lys Lys Val Leu Arg Lys Gly Asp Arg Gly Asp Glu Val
            20                  25                  30

Cys Gln Leu Gln Thr Leu Leu Asn Leu Cys Gly Tyr Asp Val Gly Lys
        35                  40                  45

Pro Asp Gly Ile Phe Gly Asn Asn Thr Phe Asn Gln Val Val Lys Phe
    50                  55                  60

Gln Lys Asp Asn Cys Leu Asp Ser Asp Gly Ile Val Gly Lys Asn Thr
65                  70                  75                  80

Trp Ala Glu Leu Phe Ser Lys Tyr Ser Pro Pro Ile Pro Tyr Lys Thr
                85                  90                  95

Ile Pro Met Pro Thr Ala Asn Lys Ser Arg Ala Ala Ala Thr Pro Val
            100                 105                 110

Met Asn Ala Val Glu Asn Ala Thr Gly Val Arg Ser Gln Leu Leu Leu
        115                 120                 125

Thr Phe Ala Ser Ile Glu Ser Ala Phe Asp Tyr Glu Ile Lys Ala Lys
    130                 135                 140

Thr Ser Ser Ala Thr Gly Trp Phe Gln Phe Leu Thr Gly Thr Trp Lys
145                 150                 155                 160

Thr Met Ile Glu Asn Tyr Gly Met Lys Tyr Gly Val Leu Thr Asp Pro
```

```
                    165                 170                 175
Thr Gly Ala Leu Arg Lys Asp Pro Arg Ile Ser Ala Leu Met Gly Ala
                180                 185                 190

Glu Leu Ile Lys Glu Asn Met Asn Ile Leu Arg Pro Val Leu Lys Arg
            195                 200                 205

Glu Pro Thr Asp Thr Asp Leu Tyr Leu Ala His Phe Gly Pro Gly
    210                 215                 220

Ala Ala Arg Arg Phe Leu Thr Thr Gly Gln Asn Glu Leu Ala Ala Thr
225                 230                 235                 240

His Phe Pro Lys Glu Ala Gln Ala Asn Pro Ser Ile Phe Tyr Asn Lys
                245                 250                 255

Asp Gly Ser Pro Lys Thr Ile Gln Glu Val Tyr Asn Leu Met Asp Gly
                260                 265                 270

Lys Val Ala Ala His Arg Lys
                275

<210> SEQ ID NO 72
<211> LENGTH: 294
<212> TYPE: PRT
<213> ORGANISM: unknown
<220> FEATURE:
<223> OTHER INFORMATION: pKKZ-144_K2_pET32b

<400> SEQUENCE: 72

Ala Met Gly Ser Lys Arg Lys Arg Lys Arg Lys Lys Val Leu
1               5                   10                  15

Arg Lys Gly Asp Arg Gly Asp Glu Val Cys Gln Leu Gln Thr Leu Leu
                20                  25                  30

Asn Leu Cys Gly Tyr Asp Val Gly Lys Pro Asp Gly Ile Phe Gly Asn
            35                  40                  45

Asn Thr Phe Asn Gln Val Val Lys Phe Gln Lys Asp Asn Cys Leu Asp
        50                  55                  60

Ser Asp Gly Ile Val Gly Lys Asn Thr Trp Ala Glu Leu Phe Ser Lys
65                  70                  75                  80

Tyr Ser Pro Pro Ile Pro Tyr Lys Thr Ile Pro Met Pro Thr Ala Asn
                85                  90                  95

Lys Ser Arg Ala Ala Ala Thr Pro Val Met Asn Ala Val Glu Asn Ala
            100                 105                 110

Thr Gly Val Arg Ser Gln Leu Leu Leu Thr Phe Ala Ser Ile Glu Ser
        115                 120                 125

Ala Phe Asp Tyr Glu Ile Lys Ala Lys Thr Ser Ser Ala Thr Gly Trp
    130                 135                 140

Phe Gln Phe Leu Thr Gly Thr Trp Lys Thr Met Ile Glu Asn Tyr Gly
145                 150                 155                 160

Met Lys Tyr Gly Val Leu Thr Asp Pro Thr Gly Ala Leu Arg Lys Asp
                165                 170                 175

Pro Arg Ile Ser Ala Leu Met Gly Ala Glu Leu Ile Lys Glu Asn Met
            180                 185                 190

Asn Ile Leu Arg Pro Val Leu Arg Glu Pro Thr Asp Thr Asp Leu
        195                 200                 205

Tyr Leu Ala His Phe Gly Pro Gly Ala Ala Arg Arg Phe Leu Thr
    210                 215                 220

Thr Gly Gln Asn Glu Leu Ala Ala Thr His Phe Pro Lys Glu Ala Gln
225                 230                 235                 240

Ala Asn Pro Ser Ile Phe Tyr Asn Lys Asp Gly Ser Pro Lys Thr Ile
```

```
                245                 250                 255
Gln Glu Val Tyr Asn Leu Met Asp Gly Lys Val Ala Ala His Arg Lys
            260                 265                 270

Leu Glu Lys Arg Lys Lys Arg Lys Lys Arg Lys Arg Ser Lys Arg Lys
            275                 280                 285

Lys Arg Lys Lys Arg Lys
        290

<210> SEQ ID NO 73
<211> LENGTH: 285
<212> TYPE: PRT
<213> ORGANISM: unknown
<220> FEATURE:
<223> OTHER INFORMATION: pK2KZ144_pET32b_mod1

<400> SEQUENCE: 73

Ala Met Gly Ser Lys Arg Lys Lys Arg Lys Lys Arg Lys Arg Gly Ser
1               5                   10                  15

Gly Lys Arg Lys Lys Arg Lys Lys Arg Lys Lys Val Leu Arg Lys Gly
            20                  25                  30

Asp Arg Gly Asp Glu Val Cys Gln Leu Gln Thr Leu Leu Asn Leu Cys
        35                  40                  45

Gly Tyr Asp Val Gly Lys Pro Asp Gly Ile Phe Gly Asn Asn Thr Phe
    50                  55                  60

Asn Gln Val Val Lys Phe Gln Lys Asp Asn Cys Leu Asp Ser Asp Gly
65                  70                  75                  80

Ile Val Gly Lys Asn Thr Trp Ala Glu Leu Phe Ser Lys Tyr Ser Pro
                85                  90                  95

Pro Ile Pro Tyr Lys Thr Ile Pro Met Pro Thr Ala Asn Lys Ser Arg
            100                 105                 110

Ala Ala Ala Thr Pro Val Met Asn Ala Val Glu Asn Ala Thr Gly Val
        115                 120                 125

Arg Ser Gln Leu Leu Thr Phe Ala Ser Ile Glu Ser Ala Phe Asp
    130                 135                 140

Tyr Glu Ile Lys Ala Lys Thr Ser Ser Ala Thr Gly Trp Phe Gln Phe
145                 150                 155                 160

Leu Thr Gly Thr Trp Lys Thr Met Ile Glu Asn Tyr Gly Met Lys Tyr
                165                 170                 175

Gly Val Leu Thr Asp Pro Thr Gly Ala Leu Arg Lys Asp Pro Arg Ile
            180                 185                 190

Ser Ala Leu Met Gly Ala Glu Leu Ile Lys Glu Asn Met Asn Ile Leu
        195                 200                 205

Arg Pro Val Leu Lys Arg Glu Pro Thr Asp Thr Asp Leu Tyr Leu Ala
    210                 215                 220

His Phe Phe Gly Pro Gly Ala Ala Arg Arg Phe Leu Thr Thr Gly Gln
225                 230                 235                 240

Asn Glu Leu Ala Ala Thr His Phe Pro Lys Gly Ala Gln Ala Asn Pro
                245                 250                 255

Ser Ile Phe Tyr Asn Lys Asp Gly Ser Pro Lys Thr Ile Gln Glu Val
            260                 265                 270

Tyr Asn Leu Met Asp Gly Lys Val Ala Ala His Arg Lys
        275                 280                 285

<210> SEQ ID NO 74
<211> LENGTH: 287
<212> TYPE: PRT
```

<213> ORGANISM: unknown
<220> FEATURE:
<223> OTHER INFORMATION: pK2KZ144_pET32b_mod2

<400> SEQUENCE: 74

Ala Met Gly Ser Lys Arg Lys Arg Lys Lys Arg Lys Arg Gly Ser
1               5                   10                  15

Gly Ser Gly Lys Arg Lys Arg Lys Arg Lys Lys Val Leu Arg
            20                  25                  30

Lys Gly Asp Arg Gly Asp Glu Val Cys Gln Leu Gln Thr Leu Leu Asn
            35                  40                  45

Leu Cys Gly Tyr Asp Val Gly Lys Pro Asp Gly Ile Phe Gly Asn Asn
50                  55                  60

Thr Phe Asn Gln Val Val Lys Phe Gln Lys Asp Asn Cys Leu Asp Ser
65                  70                  75                  80

Asp Gly Ile Val Gly Lys Asn Thr Trp Ala Glu Leu Phe Ser Lys Tyr
                85                  90                  95

Ser Pro Pro Ile Pro Tyr Lys Thr Ile Pro Met Pro Thr Ala Asn Lys
                100                 105                 110

Ser Arg Ala Ala Ala Thr Pro Val Met Asn Ala Val Glu Asn Ala Thr
                115                 120                 125

Gly Val Arg Ser Gln Leu Leu Leu Thr Phe Ala Ser Ile Glu Ser Ala
                130                 135                 140

Phe Asp Tyr Glu Ile Lys Ala Lys Thr Ser Ser Ala Thr Gly Trp Phe
145                 150                 155                 160

Gln Phe Leu Thr Gly Thr Trp Lys Thr Met Ile Glu Asn Tyr Gly Met
                165                 170                 175

Lys Tyr Gly Val Leu Thr Asp Pro Thr Gly Ala Leu Arg Lys Asp Pro
                180                 185                 190

Arg Ile Ser Ala Leu Met Gly Ala Glu Leu Ile Lys Glu Asn Met Asn
                195                 200                 205

Ile Leu Arg Pro Val Leu Lys Arg Glu Pro Thr Asp Thr Asp Leu Tyr
                210                 215                 220

Leu Ala His Phe Phe Gly Pro Gly Ala Ala Arg Arg Phe Leu Thr Thr
225                 230                 235                 240

Gly Gln Asn Glu Leu Ala Ala Thr His Phe Pro Lys Glu Ala Gln Ala
                245                 250                 255

Asn Pro Ser Ile Phe Tyr Asn Lys Asp Gly Ser Pro Lys Thr Ile Gln
                260                 265                 270

Glu Val Tyr Asn Leu Met Asp Gly Lys Val Ala Ala His Arg Lys
                275                 280                 285

<210> SEQ ID NO 75
<211> LENGTH: 292
<212> TYPE: PRT
<213> ORGANISM: unknown
<220> FEATURE:
<223> OTHER INFORMATION: smi01_KRK9

<400> SEQUENCE: 75

Ala Met Gly Ser Lys Arg Lys Arg Lys Lys Arg Lys Glu Tyr Asp
1               5                   10                  15

Met Ile Leu Lys Phe Gly Ser Lys Gly Asp Ala Val Ala Thr Leu Gln
                20                  25                  30

Lys Gln Leu Ala Lys Met Gly Tyr Lys Gly Val Lys Asp Lys Pro Leu
            35                  40                  45

Ser Val Asp Gly His Phe Gly Glu Ser Thr Glu Phe Ala Val Ile Gln
    50                  55                  60

Leu Gln Arg Lys Phe Gly Leu Val Ala Asp Gly Lys Val Gly Asp Lys
65                  70                  75                  80

Thr Arg Gln Ala Leu Ala Gly Asp Ser Val Ser Lys Phe Leu Lys Asp
                85                  90                  95

Glu Asp Tyr Lys Lys Ala Ala Ile Arg Leu Lys Val Pro Glu Leu Val
            100                 105                 110

Ile Arg Val Phe Gly Ala Val Glu Gly Leu Gly Val Gly Phe Leu Pro
        115                 120                 125

Asn Gly Lys Ala Lys Ile Leu Phe Glu Arg His Arg Met Tyr Phe Tyr
    130                 135                 140

Leu Cys Gln Ala Leu Gly Lys Thr Phe Ala Asn Ser Gln Val Lys Ile
145                 150                 155                 160

Thr Pro Asn Ile Val Asn Thr Leu Thr Gly Gly Tyr Lys Gly Asp Ala
                165                 170                 175

Ala Glu Tyr Thr Arg Leu Ser Met Ala Ile Asn Ile His Lys Glu Ser
            180                 185                 190

Ala Leu Met Ser Thr Ser Trp Gly Gln Phe Gln Ile Met Gly Glu Asn
        195                 200                 205

Trp Lys Asp Leu Gly Tyr Ser Ser Val Gln Glu Phe Val Asp Gln Gln
    210                 215                 220

Gln Leu Asn Glu Gly Asn Gln Leu Glu Ala Phe Ile Arg Phe Ile Glu
225                 230                 235                 240

Trp Lys Pro Gly Leu Leu Glu Ala Leu Arg Lys Gln Asp Trp Asp Thr
                245                 250                 255

Val Phe Thr Leu Tyr Asn Gly Lys Asn Tyr Lys Lys Leu Gly Tyr Gln
            260                 265                 270

Ala Lys Phe Gln Lys Glu Trp Asp His Leu Glu Pro Ile Tyr Arg Glu
        275                 280                 285

Lys Thr Ala Ala
    290

<210> SEQ ID NO 76
<211> LENGTH: 176
<212> TYPE: PRT
<213> ORGANISM: unknown
<220> FEATURE:
<223> OTHER INFORMATION: smi02_KRK9

<400> SEQUENCE: 76

Ala Met Gly Ser Lys Arg Lys Lys Arg Lys Arg Lys Gly Asn Ile
1               5                   10                  15

Phe Glu Met Leu Arg Ile Asp Glu Gly Leu Arg Leu Lys Ile Tyr Lys
                20                  25                  30

Asp Thr Glu Gly Tyr Tyr Thr Ile Gly Ile Gly His Leu Leu Thr Lys
            35                  40                  45

Ser Pro Ser Leu Asn Ala Ala Lys Ser Glu Leu Asp Lys Ala Ile Gly
        50                  55                  60

Arg Asn Cys Asn Gly Val Ile Thr Lys Asp Glu Ala Glu Lys Leu Phe
65                  70                  75                  80

Asn Gln Asp Val Asp Ala Ala Val Arg Gly Ile Leu Arg Asn Ala Lys
                85                  90                  95

Leu Lys Pro Val Tyr Asp Ser Leu Asp Ala Val Arg Arg Cys Ala Leu
            100                 105                 110

```
Ile Asn Met Val Phe Gln Met Gly Glu Thr Gly Val Ala Gly Phe Thr
            115                 120                 125

Asn Ser Leu Arg Met Leu Gln Gln Lys Arg Trp Asp Glu Ala Ala Val
            130                 135                 140

Asn Leu Ala Lys Ser Arg Trp Tyr Asn Gln Thr Pro Asn Arg Ala Lys
145                 150                 155                 160

Arg Val Ile Thr Thr Phe Arg Thr Gly Thr Trp Asp Ala Tyr Lys Asn
                    165                 170                 175

<210> SEQ ID NO 77
<211> LENGTH: 164
<212> TYPE: PRT
<213> ORGANISM: unknown
<220> FEATURE:
<223> OTHER INFORMATION: smi03_KRK9

<400> SEQUENCE: 77

Ala Met Gly Ser Lys Arg Lys Lys Arg Lys Lys Arg Lys Val Ser Lys
1               5                   10                  15

Val Gln Phe Asn Pro Arg Ser Arg Thr Asp Ala Ile Phe Val His Cys
            20                  25                  30

Ser Ala Thr Lys Pro Glu Met Asp Ile Gly Val Glu Thr Ile Arg Met
        35                  40                  45

Trp His Lys Gln Gln Ala Trp Leu Asp Val Gly Tyr His Phe Ile Ile
    50                  55                  60

Lys Arg Asp Gly Thr Val Glu Glu Gly Arg Pro Val Asn Val Val Gly
65                  70                  75                  80

Ser His Val Lys Asp Trp Asn Ser Arg Ser Val Gly Val Cys Leu Val
                85                  90                  95

Gly Gly Ile Asn Ala Lys Gly Gln Phe Glu Ala Asn Phe Thr Pro Ala
            100                 105                 110

Gln Met Asn Ser Leu Arg Asn Lys Leu Asp Asp Leu Lys Val Met Tyr
        115                 120                 125

Pro Gln Ala Glu Ile Arg Ala His His Asp Val Ala Pro Lys Ala Cys
    130                 135                 140

Pro Ser Phe Asp Leu Gln Arg Trp Leu Ser Thr Asn Glu Leu Val Thr
145                 150                 155                 160

Ser Asp Arg Gly

<210> SEQ ID NO 78
<211> LENGTH: 194
<212> TYPE: PRT
<213> ORGANISM: unknown
<220> FEATURE:
<223> OTHER INFORMATION: smi04_KRK9

<400> SEQUENCE: 78

Ala Met Gly Ser Lys Arg Lys Lys Arg Lys Lys Arg Lys Gly Lys Pro
1               5                   10                  15

Lys Asp Glu Ile Phe Asp Glu Ile Leu Gly Lys Glu Gly Gly Tyr Val
            20                  25                  30

Asn His Pro Asp Asp Lys Gly Gly Pro Thr Lys Trp Gly Ile Thr Glu
        35                  40                  45

Lys Val Ala Arg Ala His Gly Tyr Arg Gly Asp Met Arg Asn Leu Thr
    50                  55                  60

Arg Gly Gln Ala Leu Glu Ile Leu Glu Thr Asp Tyr Trp Tyr Gly Pro
65                  70                  75                  80
```

```
Arg Phe Asp Arg Val Ala Lys Ala Ser Pro Asp Val Ala Ala Glu Leu
                85                  90                  95

Cys Asp Thr Gly Val Asn Met Gly Pro Ser Val Ala Ala Lys Met Leu
            100                 105                 110

Gln Arg Trp Leu Asn Val Phe Asn Gln Gly Gly Arg Leu Tyr Pro Asp
        115                 120                 125

Met Asp Thr Asp Gly Arg Ile Gly Pro Arg Thr Leu Asn Ala Leu Arg
130                 135                 140

Val Tyr Leu Glu Lys Arg Gly Lys Asp Gly Glu Arg Val Leu Leu Val
145                 150                 155                 160

Ala Leu Asn Cys Thr Gln Gly Glu Arg Tyr Leu Glu Leu Ala Glu Lys
                165                 170                 175

Arg Glu Ala Asp Glu Ser Phe Val Tyr Gly Trp Met Lys Glu Arg Val
            180                 185                 190

Leu Ile

<210> SEQ ID NO 79
<211> LENGTH: 52
<212> TYPE: DNA
<213> ORGANISM: artificial sequence
<220> FEATURE:
<223> OTHER INFORMATION: primer PKgp144 for

<400> SEQUENCE: 79
atgggatcca aacgcaagaa acgtaagaaa cgcaaaaaag tattacgcaa ag          52

<210> SEQ ID NO 80
<211> LENGTH: 51
<212> TYPE: DNA
<213> ORGANISM: artificial sequence
<220> FEATURE:
<223> OTHER INFORMATION: primer PKgp188 for

<400> SEQUENCE: 80
atgggatcca aacgcaagaa acgtaagaaa cgcaaaaact tccggacgaa g           51

<210> SEQ ID NO 81
<211> LENGTH: 18
<212> TYPE: DNA
<213> ORGANISM: artificial sequence
<220> FEATURE:
<223> OTHER INFORMATION: primer gp144 rev

<400> SEQUENCE: 81
ttttctatgt gctgcaac                                                18

<210> SEQ ID NO 82
<211> LENGTH: 19
<212> TYPE: DNA
<213> ORGANISM: artificial sequence
<220> FEATURE:
<223> OTHER INFORMATION: primer gp144 rev

<400> SEQUENCE: 82
atacgaaata acgtgacga                                               19
```

```
<210> SEQ ID NO 83
<211> LENGTH: 18
<212> TYPE: DNA
<213> ORGANISM: artificial sequence
<220> FEATURE:
<223> OTHER INFORMATION: primer gp144 for

<400> SEQUENCE: 83
atgaaagtat tacgcaaa                                                   18
```

ANTIMICROBIAL AGENTS

This application is a national phase application under 35 U.S.C. §371 of International Patent Application No. PCT/EP2009/060947 filed Aug. 25, 2009 which claims priority to Great Britain Patent Application No. GB 0815484.1 filed Aug. 26, 2008. The entire text of each of the above-referenced disclosures are specifically incorporated herein by reference without disclaimer.

The present invention relates to modified endolysin variants with improved antibacterial action against Gram-negative bacteria. Said modified endolysin variants comprise an endolysin and a cationic peptide fused to the endolysin, thus enhancing the cationicity of said endolysin. The present invention also relates to a microorganism transformed with a nucleic acid comprising a nucleotide sequence encoding a modified endolysin variant with enhanced cationicity. The invention further relates to a method for producing an endolysin variant using a microorganism transformed with a nucleic acid encoding an endolysin variant according to the present invention as production organism.

In particular the present invention relates to endolysin variants comprising an endolysin to which a peptide stretch with membrane or LPS disrupting activity is fused. Moreover, the present invention relates to nucleic acid molecules encoding said modified endolysin variant, vectors comprising said nucleic acid molecules and host cells comprising either said nucleic acid molecules or said vectors. In addition, the present invention relates to a method for producing said endolysin variant. Further, the present invention relates to said modified endolysin variant for use as a medicament, in particular for the treatment or prevention of Gram-negative bacterial infections, as diagnostic means, disinfectant or as cosmetic substance. The present invention also relates to the removal or reduction or prevention of Gram-negative bacterial contamination of foodstuff, of food processing equipment, of food processing plants, of surfaces coming into contact with foodstuff, of medical devices, of surfaces in hospitals and surgeries. Furthermore, the present invention relates to the use of said endolysin variant as a diagnostic means in medicinal, food or feed or environmental diagnostic. Finally, the present invention relates to a pharmaceutical composition comprising said modified endolysin variant.

Endolysins are peptidoglycan hydrolases encoded by bacteriophages (or bacterial viruses). They are synthesized during late gene expression in the lytic cycle of phage multiplication and mediate the release of progeny virions from infected cells through degradation of the bacterial peptidoglycan. They are either β(1,4)-glycosylases (lysozymes), transglycosylases, amidases or endopeptidases. Antimicrobial application of endolysins was already suggested in 1991 by Gasson (GB2243611). Although the killing capacity of endolysins has been known for a long time, the use of these enzymes as antibacterials was ignored due to the success and dominance of antibiotics. Only after the appearance of multiple antibiotic resistant bacteria this simple concept of combating human pathogens with endolysins received interest. A compelling need to develop totally new classes of antibacterial agents emerged and endolysins used as 'enzybiotics'—a hybrid term of 'enzymes' and 'antibiotics'—perfectly met this need. In 2001, Fischetti and coworkers demonstrated for the first time the therapeutic potential of bacteriophage Cl endolysin towards group A streptococci (Nelson et al., 2001). Since then many publications have established endolysins as an attractive and complementary alternative to control bacterial infections, particularly by Gram-positive bacteria. Subsequently different endolysins against other Gram-positive pathogens such as *Streptococcus pneumoniae* (Loeffler et al., 2001), *Bacillus anthracis* (Schuch et al., 2002), *S. agalactiae* (Cheng et al., 2005) and *Staphylococcus aureus* (Rashel et al, 2007) have proven their efficacy as enzybiotics. Nowadays, the most important challenge of endolysin therapy lies in the insensitivity of Gram-negative bacteria towards the exogenous action of endolysins, since the outer membrane shields the access of endolysins from the peptidoglycan. This currently prevents the expansion of the range of effective endolysins to important Gram-negative pathogens.

Gram-negative bacteria possess an outer membrane, with its characteristic asymmetric bilayer as a hallmark. The outer membrane bilayer consists of an inner monolayer containing phospholipids (primarily phosphatidyl ethanolamine) and an outer monolayer that is mainly composed of a single glycolipid, lipopolysaccharide (LPS). There is an immense diversity of LPS structures in the bacterial kingdom and the LPS structure may be modified in response to prevailing environmental conditions. The stability of the LPS layer and interaction between different LPS molecules is mainly achieved by the electrostatic interaction of divalent ions ($Mg^{2+}$, $Ca^{2+}$) with the anionic components of the LPS molecule (phosphate groups in the lipid A and the inner core and carboxyl groups of KDO). Therefore, the cation-binding sites are essential for the integrity of the outer membrane (Vaara, 1992). Polycationic agents such as poly-L-lysine polymers (of at least 20 residues) increase the outer membrane permeability by displacement of these stabilizing divalent cations. In addition, they exert a so-called 'self-promoted uptake' mechanism (Hancock and Wong, 1984). Due to their bulkiness, they disrupt the normal barrier function of the outer membrane and create transient cracks, promoting their own uptake (Vaara and Vaara, 1983). Furthermore, the dense and ordered packing of the hydrophobic moiety of lipid A, favored by the absence of unsaturated fatty acids, forms a rigid structure with high viscosity. This makes it less permeable for lipophilic molecules and confers additional stability to the outer membrane (OM).

Increasingly microbial resistance to antibiotics, however, is creating difficulties in treating more and more infections caused by bacteria. Particular difficulties arise with infections caused by Gram-negative bacteria like *Pseudomonas aeruginosa* and Enterobacteriaceae.

Thus, there is a need for new antimicrobial agents against Gram-negative bacteria.

This object is solved by the subject matter defined in the claims.

The following figures illustrate the present invention.

FIG. 1 is a schematic overview showing plasmid construction for recombinant production of (POLY)$^n$-gp144 ((POLY)$^n$-KZ144). Previously, pEXP5CT/POLY-gp144 (pEXP5CT/POLY-KZ144) was constructed by a tail PCR (with the BamHI restriction site and first polycation cassette in the 5' tail primer). The plasmid was linearized with BamHI, dephosphorylated and ligated with a cassette containing overhanging BamHI ends. This cassette originates from the hybridization of two complementary oligonucleotides and encodes 9 positively charged residues. One additional positive arginine residue is created at the junction site between the first and second cassette, together with a serine. Longer pEXP5CT/(POLY)$^n$-gp144 (pEXP5CT/(POLY)$^n$-KZ144) variants were constructed similarly by repeated cycles.

Figure 2:
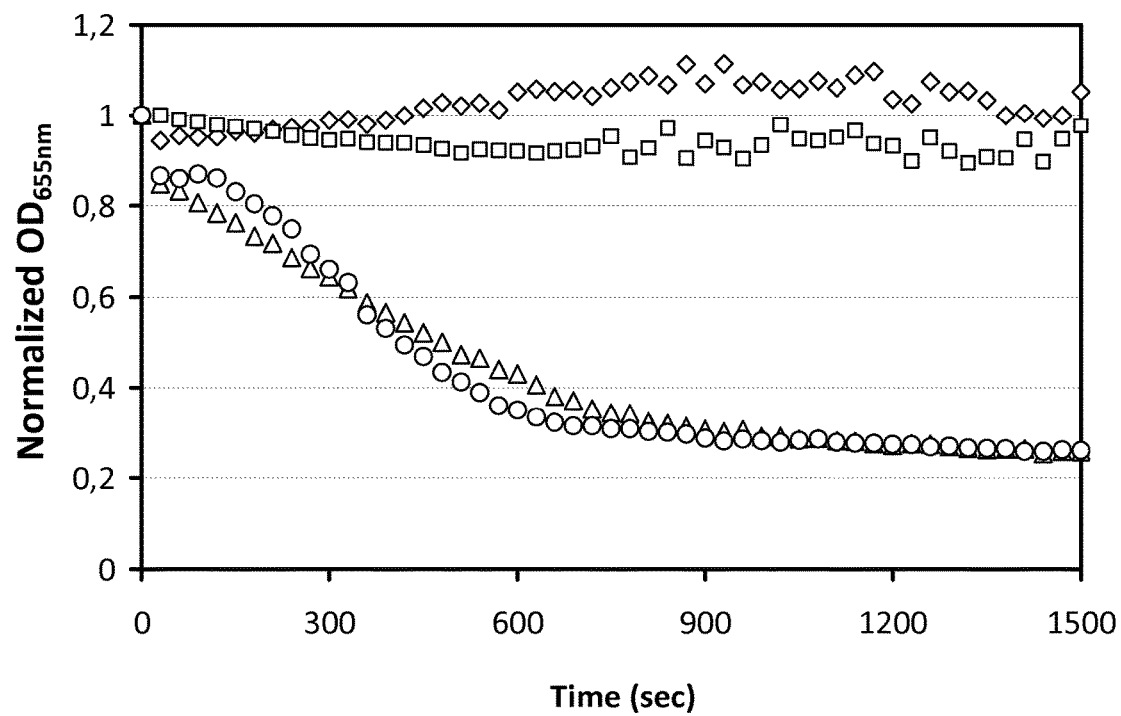

FIG. 2 shows the expression and secretion of POLY-gp144 by *Pichia pastoris*. An amount of 30 µl supernatant of a *P. pastoris* X33 expression culture [after 1 day (square), 3 days (triangle) and 4 days (circle)] is added to 270 µl chloroform-permeabilized *P. aeruginosa* PAO1p cells. The buffer conditions were the optimal enzymatic conditions of POLY-gp144 ($KH_2PO_4$/$K_2HPO_4$) I=120 mM pH 6.2). Subsequently, the optical density was spectrophotometrically recorded. A drop in optical density indicates the secretion of a muralytic enzyme by *P. pastoris*. As a negative control, *P. pastoris* X33 without expression plasmid is included (diamond).

Figure 3:
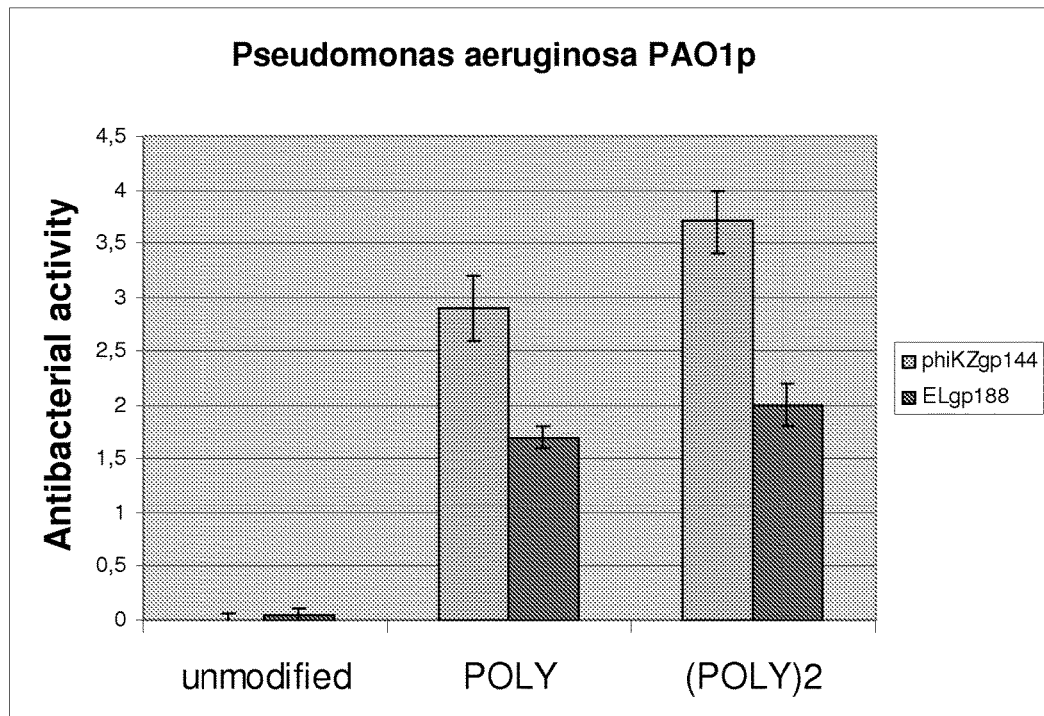

FIG. 3 shows in a graphical representation the antibacterial activity of the unmodified phiKZgp144 and ELgp188 endolysins, of the modified variants POLY-gp 144 and POLY-gp188 comprising a peptide stretch comprising 9 positively charged amino acid residues and of the modified variants $(POLY)^2$-gp144 and $(POLY)^2$-gp188 comprising a peptide stretch comprising 18 positively charged amino acid residues on *Pseudomonas aeruginosa* PAO1p cells. The error bars render the standard deviations of the mean.

Figure 4:
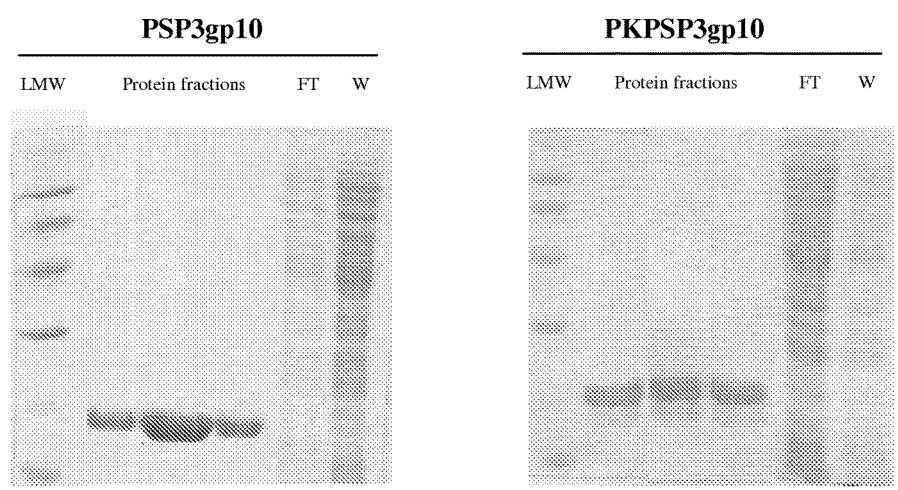

FIG. 4 shows a picture of a Coomassie-stained SDS-PAGE showing the results of the expression and purification of the unmodified endolysin PSP3gp10 and its modified endolysin variant PKPSP3gp10. The lane LMW pertains to a size marker (LMW ladder). The following three lanes pertain to protein fractions of the purified protein in Elution Buffer (20 mM $NaH_2PO_4$-NaOH pH7.4; 0.5 M NaCl; 500 mM imidazole) after $Ni^{2+}$ affinity chromatography. The lane FT pertains to the flow through and the lane W to waste fractions. Only minor secondary bands are visible in the purified protein fractions, indicating the high purity of the recombinant proteins (>90%).

Figure 5:
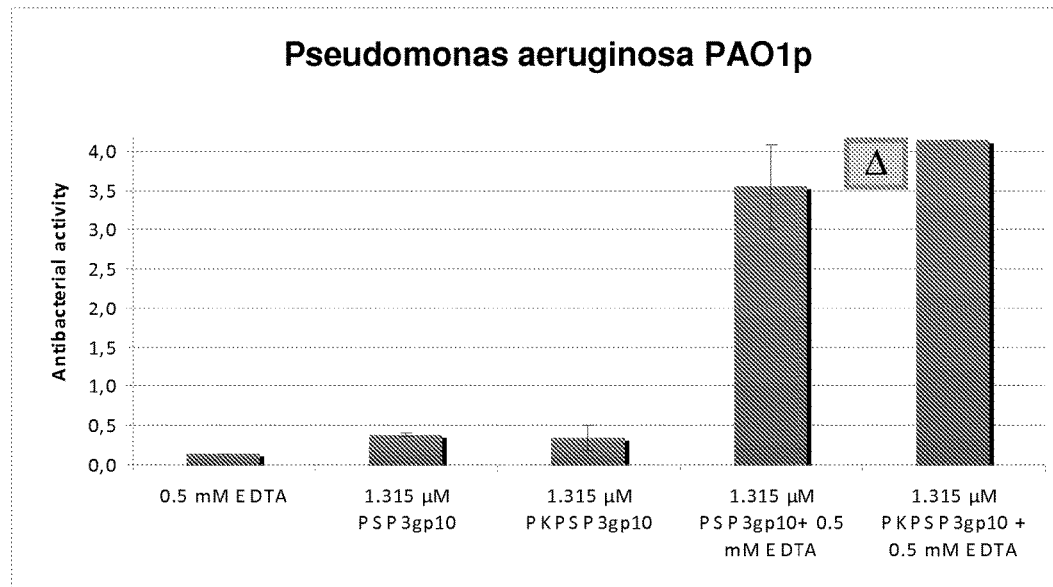
Figure 5:
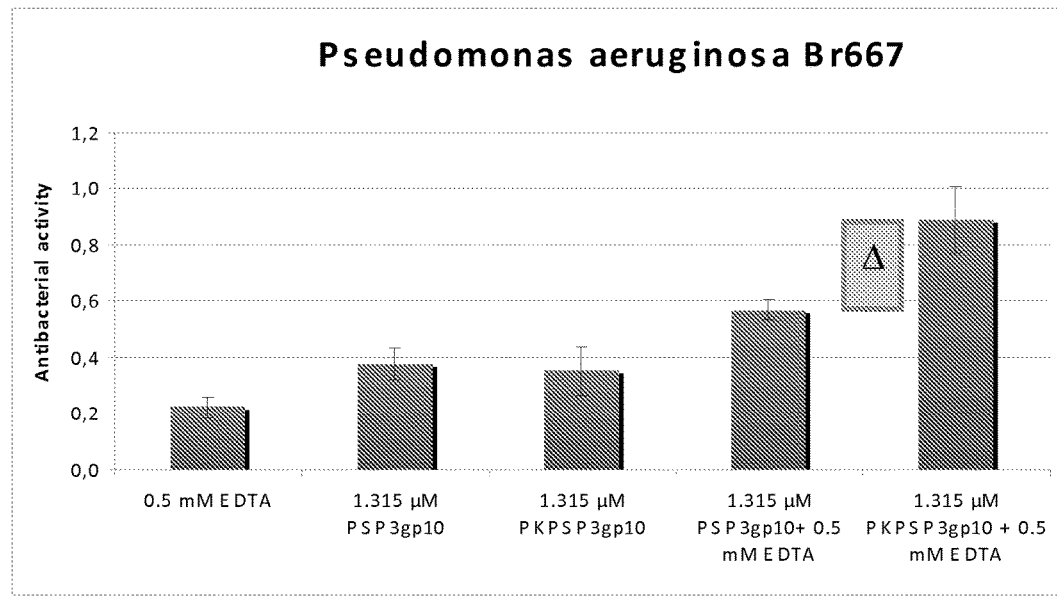
Figure 5:
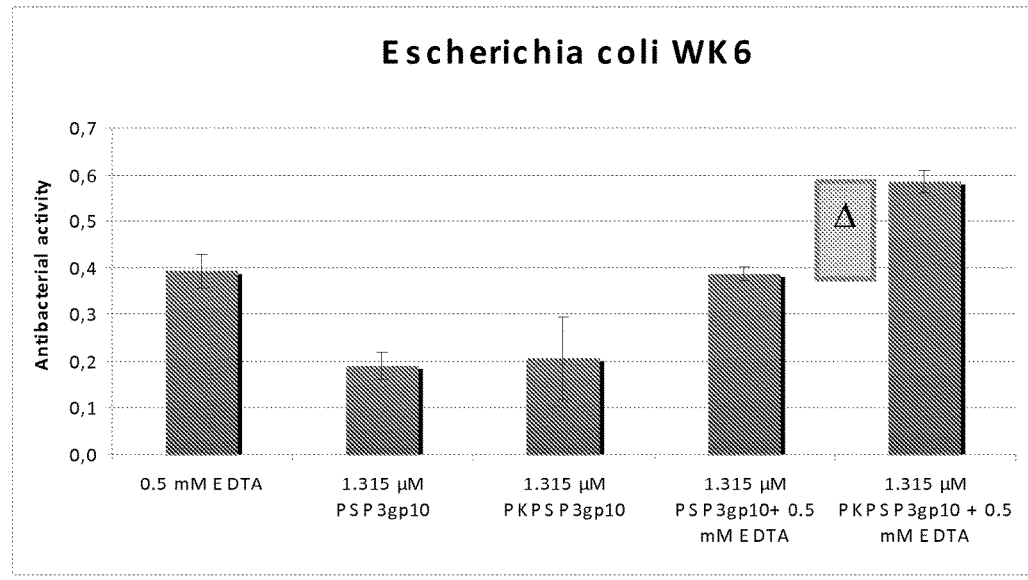
Figure 5:
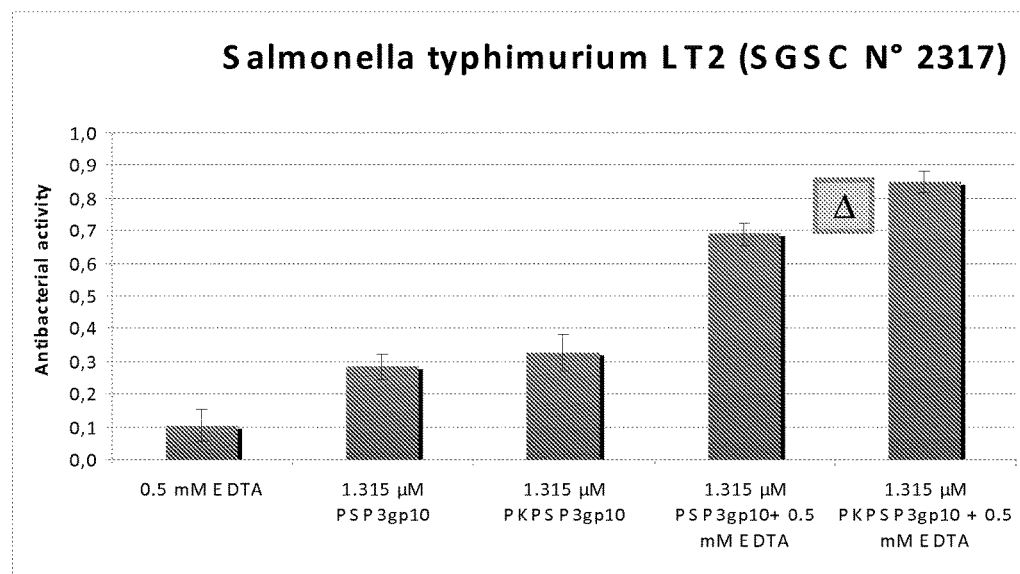

FIGS. 5A to D show in a graphic representation the antibacterial activities of unmodified PSP3gp10 and the modified PKPSP3gp10 in different compositions on several exponential growing Gram-negative bacteria after an incubation at room temperature and without shaking. Each species of Gram-negative bacteria was incubated for 30 minutes with a composition comprising 0.5 mM EDTA but no endolysin, with a composition comprising 1.315 µM unmodified PSP3gp10 but no EDTA, with a composition comprising 1.315 µM modified PKPSP3gp10 but no EDTA, with a composition comprising 1.315 µM unmodified PSP3gp10 and 0.5 mM EDTA and with a composition comprising 1.315 µM modified PKPSP3gp10 and 0.5 mM EDTA. In FIG. 5A the antibacterial activity on *P. aeruginosa* PAO1p cells is represented, in FIG. 5B the antibacterial activity on *P. aeruginosa* Br667 cells, in FIG. 5C he antibacterial activity on *E. coli* WK 6 cells and in FIG. 5D the antibacterial activity on *Salmonella typhimurium* cells. "Δ" gives the difference of activity between the respective PSP3gp10 and PKPSP3gp10 samples. The error bars render the standard deviations of the mean.

Figure 6:
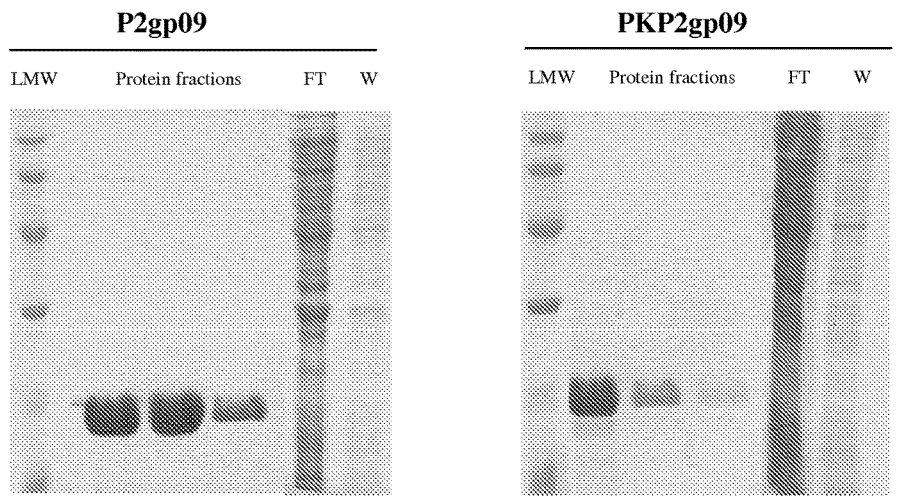

FIG. 6 shows a picture of a Coomassie-stained SDS-PAGE showing the results of the expression and purification of the unmodified endolysin P2gp09 and its modified endolysin variant PKP2gp09. The lane LMW pertains to a size marker (LMW ladder). The following three lanes pertain to protein fractions of the purified protein in Elution Buffer (20 mM $NaH_2PO_4$-NaOH pH7.4; 0.5 M NaCl; 500 mM imidazole) after $Ni^{2+}$ affinity chromatography. The lane FT pertains to the flow through and the lane W to waste fractions. Only minor secondary bands are visible in the purified protein fractions, indicating the high purity of the recombinant protein (>95%).

Figure 7:
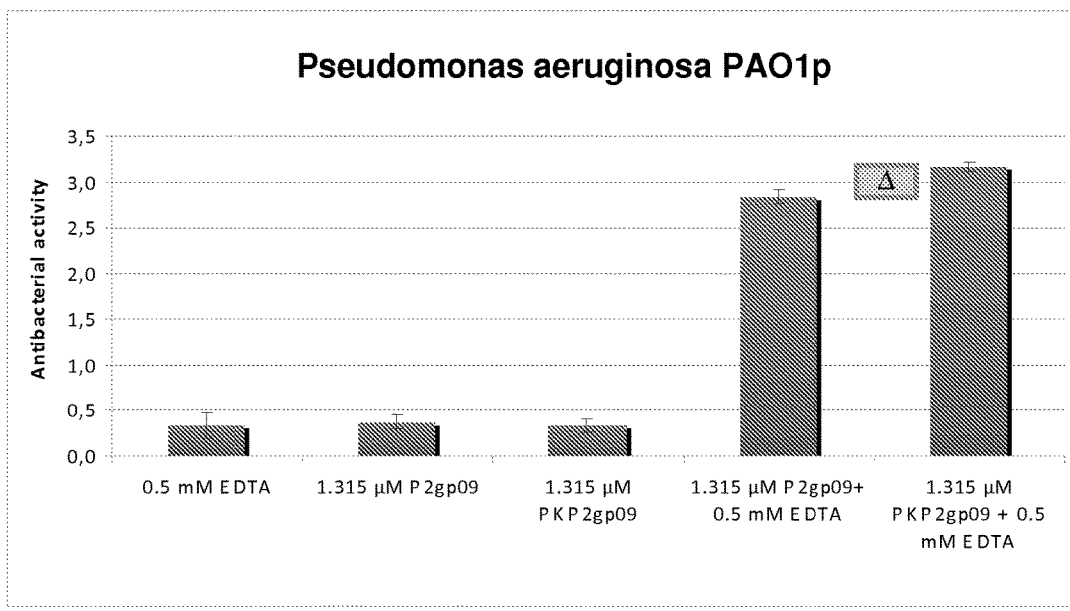
Figure 7:
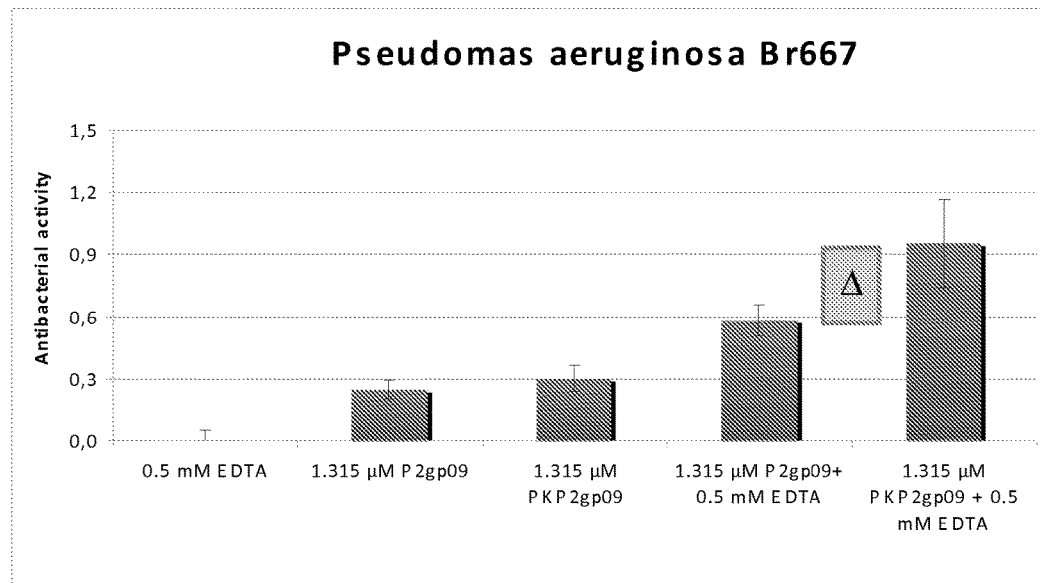
Figure 7:
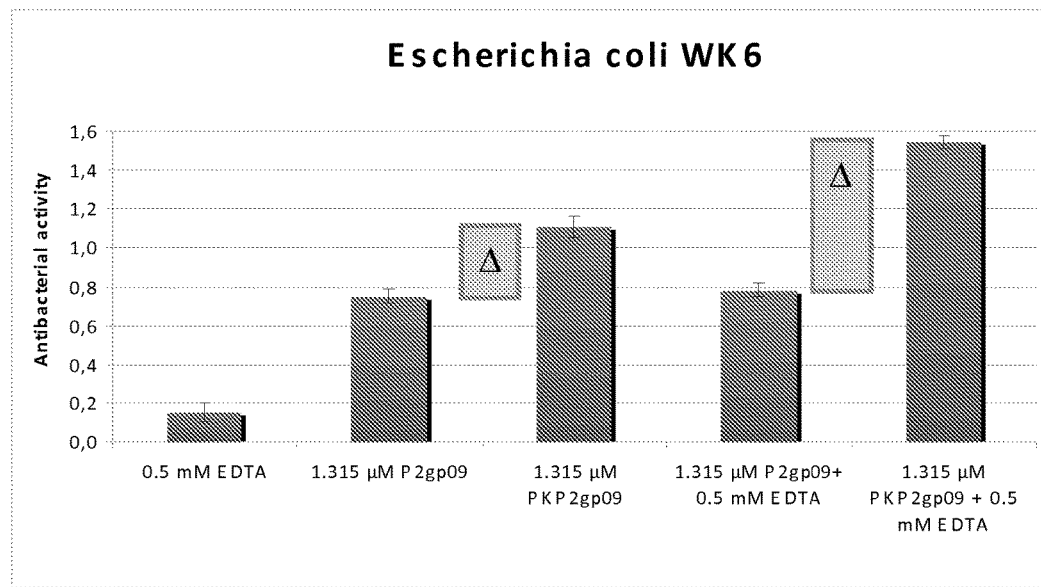
Figure 7:
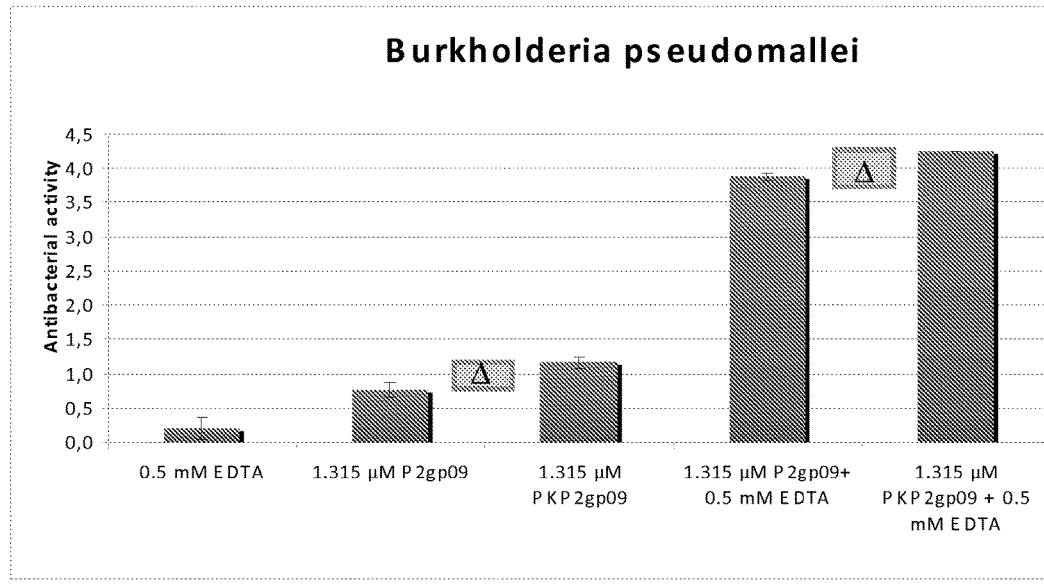
Figure 7:
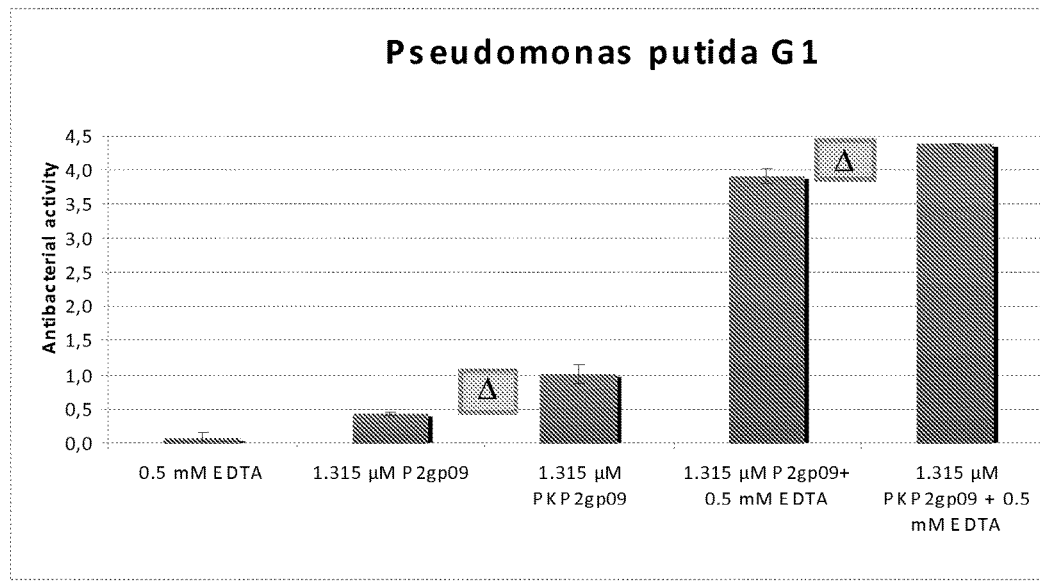
Figure 7:
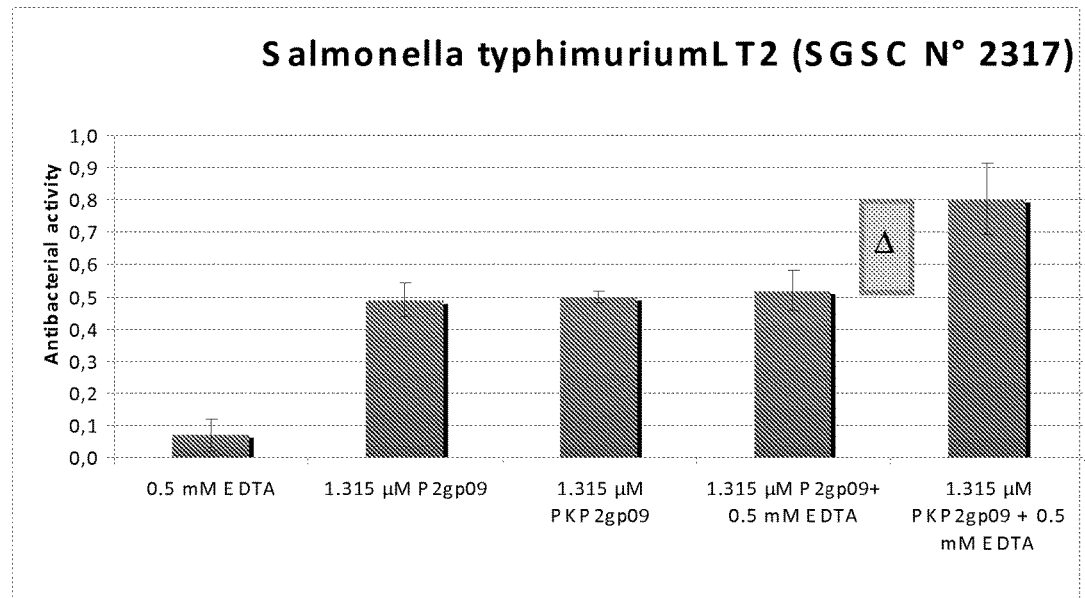

FIGS. 7A to F show in a graphic representation the antibacterial activities of unmodified P2gp09 and the modified PKP2gp09 in different compositions on several exponential growing Gram-negative bacteria after an incubation at room temperature and without shaking. Each species of Gram-negative bacteria was incubated for 30 minutes with a composition comprising 0.5 mM EDTA but no endolysin, with a composition comprising 1.315 µM unmodified P2gp09 but no EDTA, with a composition comprising 1.315 µM modified PKP2gp09 but no EDTA, with a composition comprising 1.315 µM unmodified P2gp09 and 0.5 mM EDTA and with a composition comprising 1.315 µM modified PKP2gp09 and 0.5 mM EDTA. In FIG. 7A the antibacterial activity on *P. aeruginosa* PAO1p cells is represented, in FIG. 7B the antibacterial activity on *P. aeruginosa* Br667 cells, in FIG. 7 C the antibacterial activity on *E. coli* WK 6 cells, in FIG. 7D the antibacterial activity on *Burkholderia pseudomallei* cells, in FIG. 7E the antibacterial activity on *Pseudomonas putida* G1 cells and in FIG. 7F the antibacterial activity on *Salmonella typhimurium* LT2 (SGSC N° 2317) cells. "Δ" gives the difference of activity between the respective P2gp09 and PKP2gp09 samples. The error bars render the standard deviations of the mean.

Figure 8:
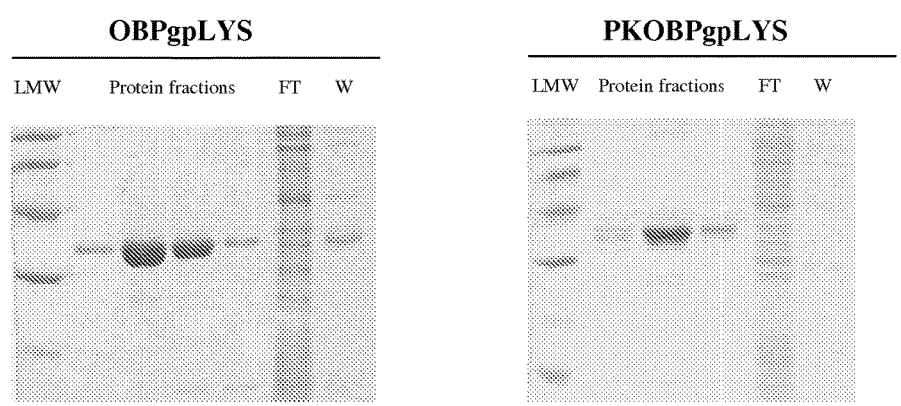

FIG. 8 shows a picture of a Coomassie-stained SDS-PAGE showing the results of the expression and purification of the unmodified endolysin OBPgpLYS and its modified endolysin variant PKOBPgpLYS. The lane LMW pertains to a size marker (LMW ladder). The following three lanes pertain to protein fractions of the purified protein in Elution Buffer (20 mM $NaH_2PO_4$-NaOH pH7.4; 0.5 M NaCl; 500 mM imidazole) after $Ni^{2+}$ affinity chromatography. The lane FT pertains to the flow through and the lane W to waste fractions. Only minor secondary bands are visible in the purified protein fractions, indicating the high purity of the recombinant proteins (>90%).

Figure 9:
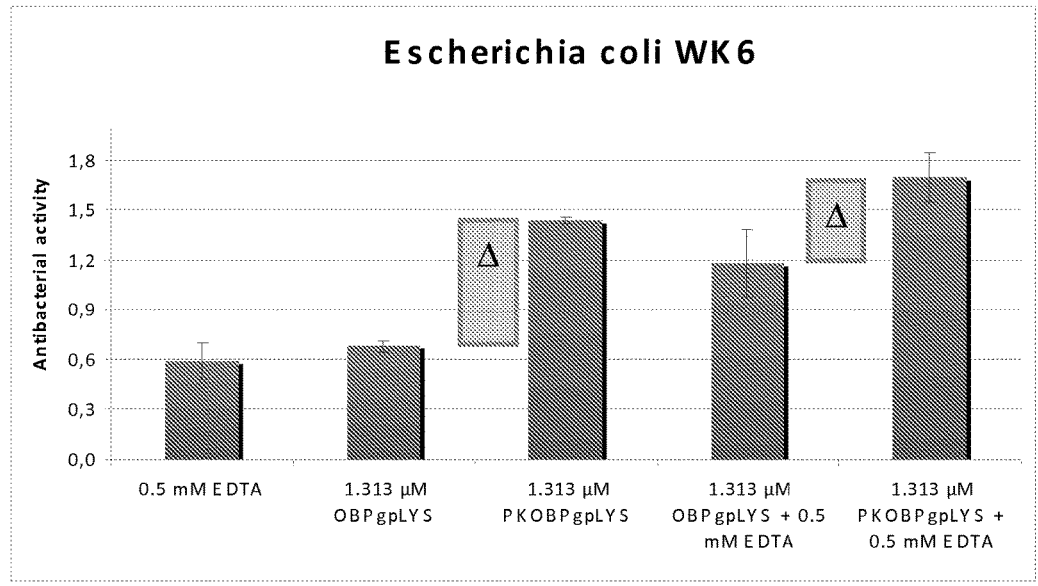
Figure 9:
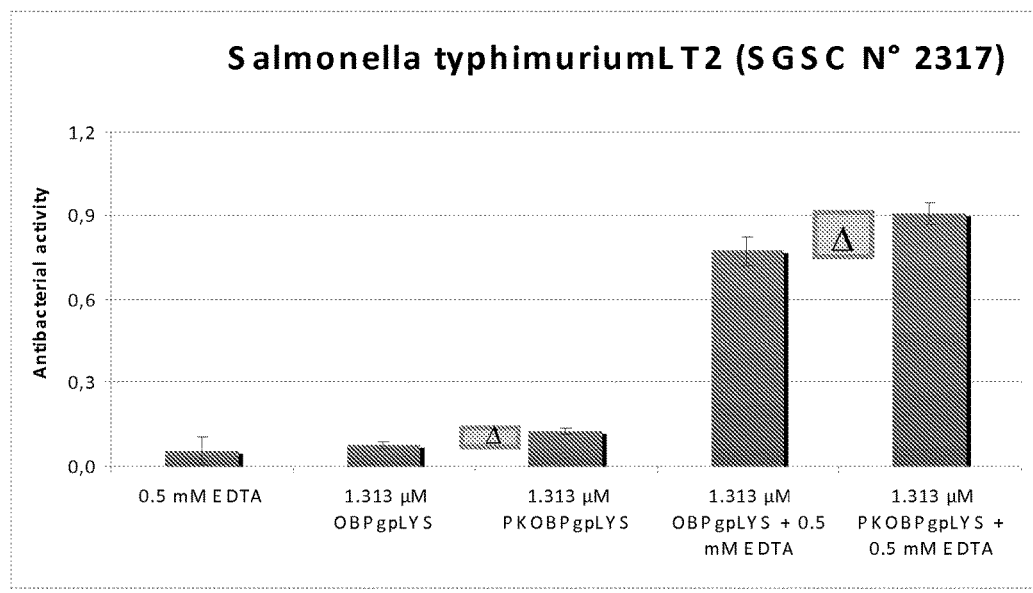
Figure 9:
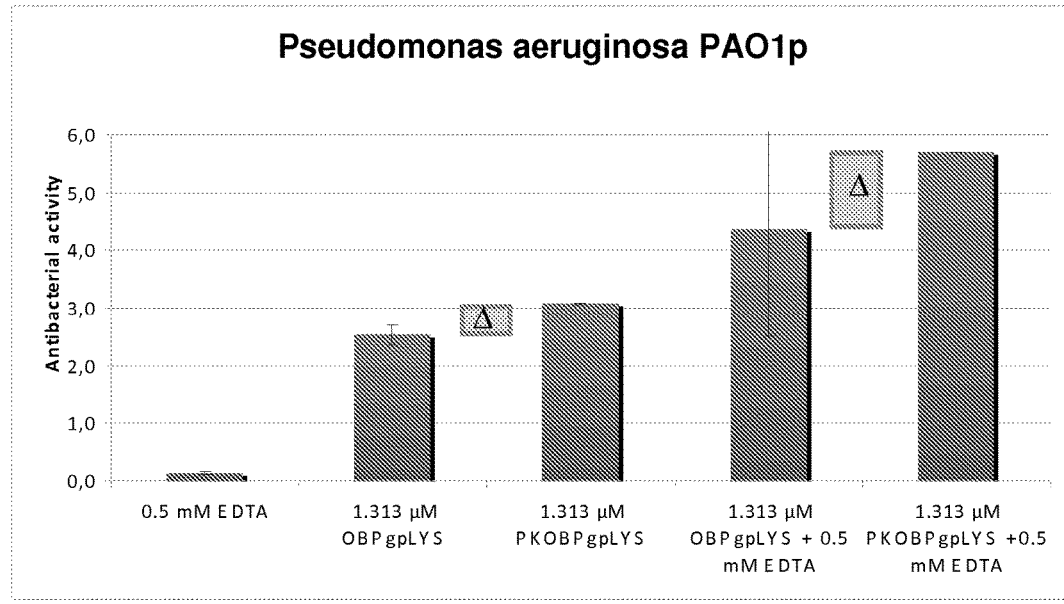
Figure 9:
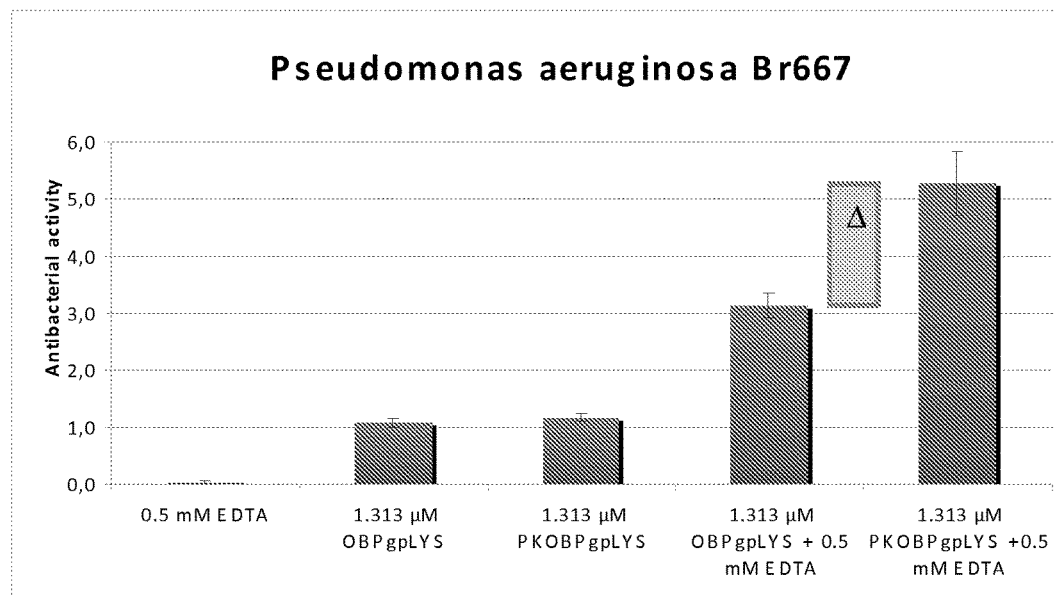
Figure 9:
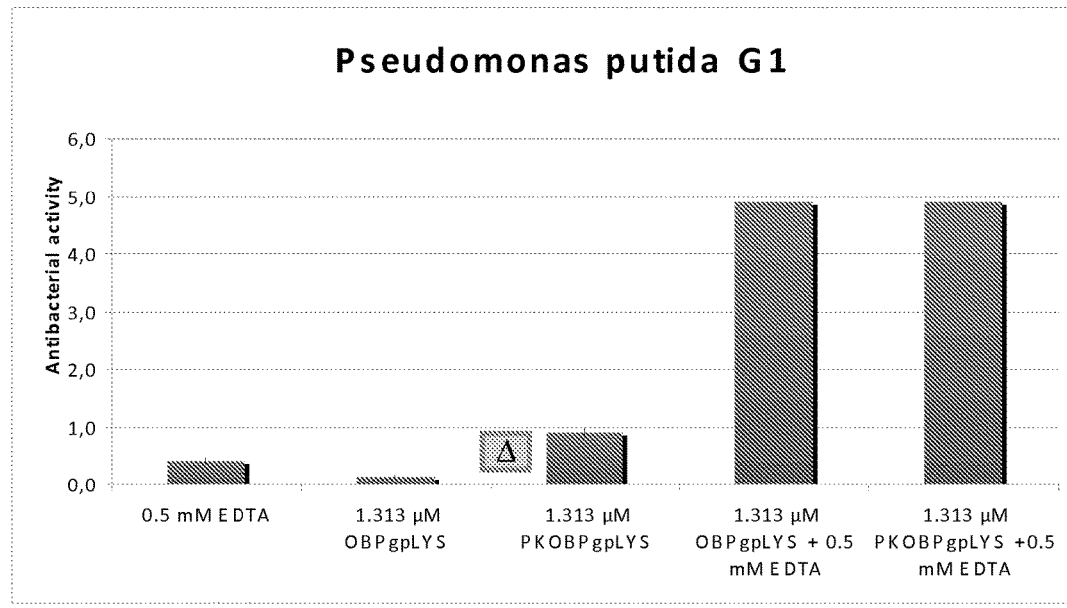
Figure 9:
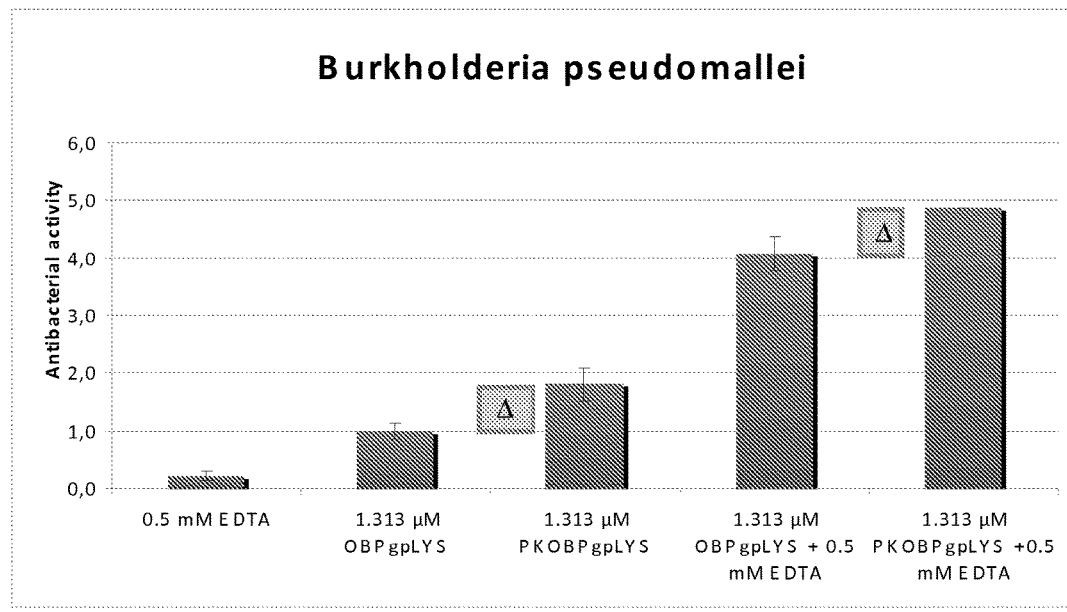

FIGS. 9A to F show in a graphic representation the antibacterial activities of different compositions of unmodified OBPgpLYS and the modified PKOBPgpLYS on several exponential growing Gram-negative bacteria after an incubation at room temperature and without shaking. Each species of Gram-negative bacteria was incubated for 30 minutes with a composition comprising 0.5 mM EDTA but no endolysin, with a composition comprising 1.315 µM unmodified OBPgpLYS but no EDTA, with a composition comprising 1.315 µM modified PKOBPgpLYS but no EDTA, with a composition comprising 1.315 µM unmodified OBPgpLYS and 0.5 mM EDTA and with a composition comprising 1.315 µM modified KOBPgpLYS and 0.5 mM EDTA. In FIG. 9A the antibacterial activity on *Escherichia coli* WK6 cells is represented, in FIG. 9B the antibacterial activity on *Salmonella typhimurium* LT2 (SGSC N° 2317) cells, in FIG. 9C the antibacterial activity on *Pseudomonas aeruginosa* PAO1p cells, in FIG. 9D the antibacterial activity on *Pseudomonas aeruginosa* Br667 cells, in FIG. 9E the antibacterial activity on *Pseudomonas putida* G1 cells and in FIG. 9F the antibacterial activity on *Burkholderia pseudomallei* cells. "Δ" gives the difference of activity between the respective OBPgpLYS and PKOBPgpLYS samples. The error bars render the standard deviations of the mean.

The term "protein" as used herein refers synonymously to the term "polypeptide". The term "protein" as used herein refers to a linear polymer of amino acid residues linked by peptide bonds in a specific sequence. The amino-acid residues of a protein may be modified by e.g.

covalent attachments of various groups such as carbohydrates and phosphate. Other substances may be more loosely associated with the polypeptide chains, such as heme or lipid, giving rise to the conjugated proteins which are also comprised by the term "protein" as used herein. There are various ways in which the polypeptide chains fold have been elucidated, in particular with regard to the presence of alpha helices and beta-pleated sheets. The term "protein" as used herein refers to all four classes of proteins being all-alpha, all-beta, alpha/beta and alpha plus beta.

The term "fusion protein" as used herein refers to an expression product resulting from the fusion of two nucleic acid sequences. Such a protein may be produced, e.g., in recombinant DNA expression systems. Moreover, the term "fusion protein" as used herein refers to a fusion of a first amino acid sequence, in particular an endolysin, autolysin and/or other peptidoglycan hydrolase, with a second or further amino acid sequence. The second or further amino acid sequence is preferably a peptide stretch, in particular a cationic and/or polycationic peptide. Preferably, said second and/or further amino acid sequence is foreign to and not substantially homologous with any domain of the first amino acid sequence.

The term "modified endolysin variant" is used herein synonymously with the term "endolysin variant". Both terms refer to a fusion protein comprising an endolysin and a peptide stretch, in particular a cationic and/or polycationic peptide.

The term "peptide stretch" as used herein refers to any kind of peptide linked to a protein such as an endolysin, autolysin and/or peptidoglycan hydrolase. In particular the term "peptide stretch" as used herein refers to a cationic peptide and/or a polycationic peptide. However, a peptide stretch in the meaning of the present invention does not refer to His-tags, Strep-tags, Avi-tags, Myc-tags, Gst-tags, JS-tags, cystein-tags, FLAG-tags or other tags known in the art, thioredoxin or maltose binding proteins (MBP). The term "tag" in contrast to the term "peptide stretch" as used herein refers to a peptide which can be useful to facilitate expression and/or affinity purification of a polypeptide, to immobilize a polypeptide to a surface or to serve as a marker or a label moiety for detection of a polypeptide e.g. by antibody binding in different ELISA assay formats as long as the function making the tag useful for one of the above listed facilitation is not caused by the positively charge of said peptide. However, the His-tag may, depending on the respective pH also be positively charged, but is used as affinity purification tool as it binds to immobilized divalent cations and is not used as a peptide stretch according to the present invention.

The term "peptide" as used herein refers to short polypeptides consisting of from about 2 to about 100 amino acid residues, more preferably from about 4 to about 50 amino acid residues, more preferably to about 5 to 30 amino acid residues, wherein the amino group of one amino acid residue is linked to the carboxyl group of another amino acid residue by a peptide bond. A peptide may have a specific function. A peptide can be a naturally occurring peptide or a synthetically designed and produced peptide. The peptide can be, for example, derived or removed from a native protein by enzymatic or chemical cleavage, or can be prepared using conventional peptide synthesis techniques (e.g., solid phase synthesis) or molecular biology techniques (see Sambrook, J. et al., Molecular Cloning: A Laboratory Manual, Cold Spring Harbor Press, Cold Spring Harbor, N.Y. (1989)). Preferred synthetically produced peptides are e.g. cationic or polycationic peptides.

As used herein, the term "cationic peptide" refers to a peptide having positively charged amino acid residues. Preferably a cationic peptide has a pKa-value of 9.0 or greater. Typically, at least four of the amino acid residues of the cationic peptide can be positively charged, for example, lysine or arginine. "Positively charged" refers to the side chains of the amino acid residues which have a net positive charge at about physiological conditions. The term "cationic peptide" as used herein refers also to polycationic peptides.

The term "polycationic peptide" as used herein refers to a synthetically designed and produced peptide composed of mostly positively charged amino acid residues, in particular lysine, arginine and/or histidine residues, more preferably lysine and/or arginine residues. A peptide is composed of mostly positively charged amino acid residues if at least about 20, 30, 40, 50, 60, 70, 75, 80, 85, 90, 95 or about 100% of the amino acid residues are positively charged amino acid residues, in particular lysine and/or arginine residues. The amino acid residues being not positively charged amino acid residues can be neutrally charged amino acid residues and/or negatively charged amino acid residues and/or hydrophobic amino acid residues. Preferably the amino acid residues being not positively charged amino acid residues are neutrally charged amino acid residues, in particular serine and/or glycine.

The term "endolysin" as used herein refers to an enzyme which is suitable to hydrolyse bacterial cell walls. "Endolysins" comprise of at least one "enzymatically active domain" (EAD) having at least one of the following activities: endopeptidase, N-acetyl-muramoyl-L-alanine-amidase (amidase), N-acetyl-muramidase, N-acetyl-glucosaminidase (lysozyme) or transglycosylases. In addition, the endolysins may contain also regions which are enzymatically inactive, and bind to the cell wall of the host bacteria, the so-called CBDs (cell wall binding domains). The endolysin may contain one, two or more CBDs. However, the term "endolysin" as used herein refers also to enzymes having at least one EAD but no CBDs. Generally, the cell wall binding domain is able to bind different components on the surface of bacteria. Preferably, the cell wall binding domain is a peptidoglycan binding domain and binds to the bacteria's peptidoglycan.

The term "cell wall" as used herein refers to all components that form the outer cell enclosure of the Gram-negative bacteria and thus guarantee their integrity. In particular, the term "cell wall" as used herein refers to peptidoglycan, the outer membrane of the Gram-negative bacteria with the lipopolysaccharide, the bacterial cell membrane, but also to additional layers deposited on the peptidoglycan as e.g. capsules, outer protein layers or slimes.

The term "autolysins" as used herein refers to enzymes related to endolysins but encoded by bacteria and involved in e.g. cell division and cell wall metabolism. An overview of autolysins can be found in "Bacterial peptidoglycan (murein) hydrolases. Vollmer W, Joris B, Charlier P, Foster S. FEMS Microbiol Rev. 2008 March; 32(2):259-86".

The term "EAD" as used herein refers to the enzymatically active domain of an endolysin. The EAD is responsible for hydrolysing bacterial peptidoglycans. It exhibits at least one enzymatic activity of an endolysin. The EAD can also be composed of more than one enzymatically active module. The term "EAD" is used herein synonymously with the term "catalytic domain".

The term "deletion" as used herein refers to the removal of 1, 2, 3, 4, 5 or more amino acid residues from the respective starting sequence.

The term "insertion" or "addition" as used herein refers to the insertion or addition of 1, 2, 3, 4, 5 or more amino acid residues to the respective starting sequence.

The term "substitution" as used herein refers to the exchange of an amino acid residue located at a certain position for a different one.

The present invention relates to improved antibacterial agents against Gram-negative bacteria, in case modified endolysin variants, comprising an endolysin fused to a peptide with lipopolysachharide (LPS) or in general membrane disrupting activity. LPS is a major component of the outer membrane of Gram-negative bacteria. It increases the negative charge of the cell membrane and protects the membrane from certain kinds of chemical attack. To a certain degree said LPS protects the membrane of Gram-negative bacteria also from endolysins added from outside of the bacteria. However, the LPS can be disrupted by peptide stretches having a LPS disrupting activity as e.g. positively charged peptides. Moreover, said peptide stretches may be involved in the outer membrane protein transport mechanism, a destabilisation of structural outer membrane proteins and/or in lipid-dependent destabilisation. The inventors of the present invention have surprisingly found, that a peptide stretch having LPS disrupting activity or in general membrane disrupting activity promotes the passage of an endolysin fused to said peptide stretch through the outer membrane of Gram-negative bacteria. After the promoted pass of the endolysin through the outer membrane of Gram-negative bacteria, the cell wall of the Gram-negative bacterium can be more easily be disrupted or desintegrated by the endolysin due to degradation of the peptidoglycan layer followed by osmotic lysis when the internal cell pressure of the bacterium cannot longer be resisted.

Thus, the present invention refers to fusion proteins composed of an endolysin having the activity of degrading the cell wall of Gram-negative bacteria and a peptide stretch with membrane disrupting activity, wherein said peptide stretch is fused to the enzyme at the N- and/or C-terminus. Said fusion proteins according to the present invention are also called modified endolysin variants or simply endolysin variants or modified endolysins.

The endolysin part of the modified endolysin variant is preferably encoded by bacteriophages specific for Gram-negative bacteria such as Gram-negative bacteria of bacterial groups, families, genera or species comprising strains pathogenic for humans or animals like Enterobacteriaceae (*Escherichia*, especially *E. coli, Salmonella, Shigella, Citrobacter, Edwardsiella, Enterobacter, Hafnia, Klebsiella*, especially *K. pneumoniae, Morganella, Proteus, Providencia, Serratia, Yersinia*), Pseudomonadaceae (*Pseudomonas*, especially *P. aeruginosa, Burkholderia, Stenotrophomonas, Shewanella, Sphingomonas, Comamonas*), *Neisseria, Moraxella, Vibrio, Aeromonas, Brucella, Francisella, Bordetella, Legionella, Bartonella, Coxiella, Haemophilus, Pasteurella, Mannheimia, Actinobacillus, Gardnerella*, Spirochaetaceae (*Treponema* and *Borrelia*), Leptospiraceae, *Campylobacter, Helicobacter, Spirillum, Streptobacillus*, Bacteroidaceae (*Bacteroides, Fusobacterium, Prevotella, Porphyromonas*), *Acinetobacter*, especially *A. baumanii*.

Moreover, the endolysin has preferably cell wall degrading activity against Gram-negative bacteria of bacterial groups, families, genera or species comprising strains pathogenic for humans or animals like Enterobacteriaceae (*Escherichia*, especially *E. coli, Salmonella, Shigella, Citrobacter, Edwardsiella, Enterobacter, Hafnia, Klebsiella*, especially *K. pneumoniae, Morganella, Proteus, Providencia, Serratia, Yersinia*), Pseudomonadaceae (*Pseudomonas*, especially *P. aeruginosa, Burkholderia, Stenotrophomonas, Shewanella, Sphingomonas, Comamonas*), *Neisseria, Moraxella, Vibrio, Aeromonas, Brucella, Francisella, Bordetella, Legionella, Bartonella, Coxiella, Haemophilus, Pasteurella, Mannheimia, Actinobacillus, Gardnerella*, Spirochaetaceae (*Treponema* and *Borrelia*), Leptospiraceae, *Campylobacter, Helicobacter, Spirillum, Streptobacillus*, Bacteroidaceae (*Bacteroides, Fusobacterium, Prevotella, Porphyromonas*), *Acinetobacter*, especially *A. baumanii*.

Preferably, the endolysin part derives from a phage or a wild type endolysin as depicted in the following table:

| phage | publication | Wild type endolysin | predicted function of the endolysin |
| --- | --- | --- | --- |
| φV10 | Perry, L. L. and Applegate, B. M. | PhiV10p30 | chitinase |
| FELS-1 | McClelland, M. and Wilson, R. K. | STM0907.Fels0 | chitinase |
| ϵ15 | Kropinksi, A. M. and McConnel, M. R. | epsilon15p25 | chitinase |
| YUA | Ceyssens. P. (Laboratory for Gene technology) | YuA20 | lytic transglycosylase (C)/1 transmembranair domain (N) |
| B3 | Braid, M. D. and Kitts, C. L. | ORF23 | lytic transglycosylase (C)/2 transmembranair domains (N) |
| BCEPµ | Summer, E. J. and Young, R. | BcepMu22 | lytic transglycosylase (M)/1 transmembranair domain (N) |
| F116 | Byrne, M. and Kropinski, A. M. | F116p62 | muraminidase (T4-like) |
| FELS-2 | McClelland, M. and Wilson, R. K. | STM2715.S.Fels2 | muraminidase (T4-like) |
| ES18 | Casjens, S. R. and Hendrix, R. W. | gp76 | muraminidase (T4-like) |
| SETP3 | De Lappe, N and Cormican, M. | SPSV3_gp23 | muraminidase (T4-like) |
| φECO32 | Savalia, D and Severinov, K | phi32_17 | muraminidase (T4-like) |
| HK022 | Juhala, R and Hendrix, R. W. | HK022p54 | muraminidase (lambdalike) |
| HK97 | Juhala, R and Hendrix, R. W. | HK97p58 | muraminidase (lambdalike) |
| HK620 | Clark, A. J. and Dhillon, T. S. | HK620p36 | muraminidase (lambdalike) |
| E1 | Pickard, D. and Dougan, G | VIP0007 | muraminidase (lambdalike) |
| SF6 | Casjens, S and Clark, A. J. | Sf6p62 | muraminidase (lambdalike) |
| SFV | Allison, G. E. and Verma, N. K. | R (SfVp40) | muraminidase (lambdalike) |
| BCEPC6B | Summer, E J and Young, R. | gp22 | muraminidase (lambdalike) |
| BCEPNAZGUL | Summer, E J and Young, R. | Nazgul38 | muraminidase (lambdalike) |
| P2 | Christie, G. E. and Calender, R. | K (P2p09) | muraminidase (lambdalike) |
| Wφ | Christie, G. E. and Esposito, D. | K (Wphi09) | muraminidase (lambdalike) |
| RV5 | Kropinski, A. M. and Johnson | rv5_gp085 | muraminidase (lambdalike) |
| JS98 | Zuber, S and Denou, E. | EpJS98_gp116 | muraminidase (T4-like) |
| 13A | Savalia, D and Molineux, I. | gp3.5 | muramoyl-L-alanine amidase |
| BA14 | Savalia, D and Molineux, I. | gp3.5 | muramoyl-L-alanine amidase |
| ECODS1 | Savalia, D and Molineux, I. | gp3.5 | muramoyl-L-alanine amidase |
| K1F | Scholl, D and Merril, C | CKV1F_gp16 | muramoyl-L-alanine amidase |
| T3 | Pajunen, M. I. and Mollineux, I. J. | T3p18 | muramoyl-L-alanine amidase |

-continued

| phage | publication | Wild type endolysin | predicted function of the endolysin |
|---|---|---|---|
| GH-1 | Kropinski, A. M. and Kovalyova, I. V. | gh-1p12 | muramoyl-L-alanine amidase |
| K11 | Molineux, I. and Savalia, D. | gp3.5 | muramoyl-L-alanine amidase |
| BIP-1 | Liu, M and Miller, J. F. | bip-1p02 | lysozyme (N)/PG-binding domain (C) |
| BMP-1 | Liu, M and Miller, J. F. | bmp-1pO2 | lysozyme (N)/PG-binding domain (C) |
| BPP-1 | Liu, M and Miller, J. F. | bpp2 | lysozyme (N)/PG-binding domain (C) |
| φCTX | Nakayama, K and Hayashi, T. | ORF12 | PG-binding domain (N)/muramidase (C) |
| BCEP43 | Summer, E J and Young, R. | Bcep43-27 | PG-binding domain (N)/muramidase (C) |
| BCEP781 | Summer, E J and Young, R. | Bcep781-27 | PG-binding domain (N)/muramidase (C) |
| BCEP1 | Summer, E J and Young, R. | Bcep1-28 | PG-binding domain (N)/muramidase (C) |
| BCEPNY3 | Summer, E J and Young, R. | BcepNY3gene26 | PG-binding domain (N)/muramidase (C) |
| φE12-2 | DeShazer, D and Nierman, W. C. | gp45 | PG-binding domain (N)/muramidase (C) |
| φ52237 | DeShazer, D and Nierman, W. C. | gp28 | PG-binding domain (N)/muramidase (C) |
| φP27 | Recktenwald, J and Schmidt, H. | P27p30 | endopeptidase |
| RB49 | Monod, C and Krisch, H. M. | RB49p102 | endopeptidase |
| φ1 | Arbiol, C. and Comeau, A. M. | phi1-p102 | endopeptidase |
| T5 | Pankova, N. V. and Ksenzenko, V. N. | lys (T5.040) | endopeptidase |
| 201phi2-1 | Thomas et al., 2008 | | PG-binding domain (N)/unknown catalytic domain (C) |
| Aeh1 | Monod, C and Krisch, H. M. | Aeh1p339 | muraminidase (T4-like) |
| YYZ-2008 | Kropinski, A. M. | YYZgp45 | muraminidase (lambda-like) |

Also preferred is the endolysin part deriving from endolysins of the *Pseudomonas aeruginosa* phages ΦKZ and EL, of the *Pseudomonas putida* phage OBP, of the phage LUZ24, or from T4 lysozyme, gp61 muramidase and PSP3 endolysin.

More preferably, the endolysin part is selected from the group consisting of phiKZgp144 according to SEQ ID NO:1, ELgp188 according to SEQ ID NO:2, *Salmonella* endolysin according to SEQ ID NO:3, Enterobacteria phage T4 endolysin according to SEQ ID NO:4, *Acinetobacter baumanii* endolysin according to SEQ ID NO:5, *E. coli* Phage K1F endolysin according to SEQ ID NO:6, OBPgpLYS according to SEQ ID NO: 7, PSP3 *Salmonella* endolysin (PSP3gp10) according to SEQ ID NO: 8 and *E. coli* Phage P2 endolysin (P2gp09) according to SEQ ID NO: 9.

In another preferred embodiment of the present invention the endolysins or the modified endolysin variants according to the present invention comprise modifications and/or alterations of the amino acid sequences. Such alterations and/or modifications may comprise mutations such as deletions, insertions and additions, substitutions or combinations thereof and/or chemical changes of the amino acid residues, e.g. biotinylation, acetylation, PEGylation, chemical changes of the amino-, SH- or carboxyl-groups. Said modified and/or altered endolysins exhibit the lytic activity of the respective wild type endolysin. However, said activity can be higher or lower as the activity of the respective wild type endolysin. Said activity can be about 10, 20, 30, 40, 50, 60, 70, 80, 90, 100, 110, 120, 130, 140, 150, 160, 170, 180, 190 or about 200% of the activity of the respective wild-type endolysin or even more. The activity can be measured by assays well known in the art by a person skilled in the art as e.g. the plate lysis assay or the liquid lysis assay which are e.g. described in (Briers et al., *J. Biochem. Biophys Methods* 70: 531-533, (2007)).

In one aspect of the invention the peptide with membrane and/or LPS disrupting activity comprises a positively charged peptide, which comprises one or more of the positively charged amino acids being lysine, arginine and/or histidine. Preferably, more than 80%, preferably more than 90%, preferably 100% of the amino acids in said peptide are positively charged amino acids. Advantageously, the cationic peptide is fused at the N-terminal and/or the C-terminal end of the endolysin variants, thus enhancing the cationicity of the latter proteins. In another embodiment of the invention, the cationic peptide fused to the endolysin is at least 5, more preferably at least 9 amino acids long.

In a preferred embodiment the endolysin variant comprises an endolysin and a peptide fused thereto said peptide comprising about 3 to about 50, more preferably about 5 to about 20, for instance about 5 to about 15 amino acid residues and at least 20, 30, 40, 50, 60 or 70%, more preferably at least 80%, for instance at least 90% of the said amino acid residues are either arginine or lysine residues. In another preferred embodiment the endolysin variant comprises an endolysin and a peptide fused thereto said peptide comprising about 3 to about 50, more preferably about 5 to about 20, for instance about 5 to about 15 amino acid residues and said amino acid residues are either arginine or lysine residues.

Preferably, the peptide stretch of the modified endolysin variant is fused to the N-terminus and/or to the C-terminus of the endolysin. In a particular preferred embodiment said peptide stretch is only fused to the N-terminus of the endolysin. However, also preferred are modified endolysin variants having a peptide stretch both on the N-terminus and on the C-terminus. Said peptide stretches on the N-terminus and on the C-terminus can be the same or distinct peptide stretches.

The peptide stretch of the modified endolysin variant according to the present invention is preferably covalently bound to the enzyme. Preferably, said peptide stretch consists of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100 amino acid residues. Especially preferred is a peptide stretch comprising about 5 to about 100 amino acid residues, about 5 to about 50 or about 5 to about 30 amino acid residues. More preferred is a peptide stretch comprising about 6 to about 42 amino acid residues, about 6 to about 39 amino acid residues, about 6 to about 38 amino acid residues, about 6 to about 31 amino acid residues, about 6 to about 25 amino acid residues, about 6 to about 24 amino acid residues, about 6 to about 22 amino acid residues, about 6 to about 21 amino acid residues, about 6 to about 20 amino acid residues, about 6 to about 19 amino acid residues, about 6 to about 16 amino acid residues, about 6 to about 14 amino acid residues, about 6 to about 12 amino acid residues, about 6 to about 10 amino acid residues or about 6 to about 9 amino acid residues.

In one aspect of the present invention the fused peptide stretch is a cationic and/or polycationic peptide, which comprises one or more of the positively charged amino acid residues of lysine, arginine and/or histidine, in particular of lysine and/or arginine. Preferably, more than about 20, 30, 40, 50, 60, 70, 75, 80, 85, 90, 95 or 99% of the amino acid residues in said peptide stretch are positively charged amino acid residues, in particular lysine and/or arginine residues. Especially preferred are peptide stretches consisting of about 100% positively charged amino acid residues, in particular arginine and/or lysine residues, wherein preferably about 60% to about 70% of said positively charged amino acid residues are lysine residues and about 30% to about 40% of said positively charged amino acid residues are arginine residues. More preferred is a peptide stretch consisting of about 100% positively charged amino acid residues, in particular arginine and/or lysine residues, wherein preferably about 64% to about 68% of said positively charged amino acid residues are lysine and about 32% to about 36% of said positively charged amino acid residues are arginine. Peptide stretches consisting of either only arginine or only lysine are also preferred.

Especially preferred are cationic and/or polycationic peptide stretches comprising at least one motive according to SEQ ID NO: 10 (KRKKRK). In particular cationic peptide stretches comprising at least 2, 3, 4, 5, 6, 7, 8, 9, 10, 11, 12, 13, 14, 15, 16 or 17 motives according to SEQ ID NO: 10 (KRKKRK) are preferred. More preferred are cationic peptide stretches comprising at least one KRK motive (lys-arg-lys), preferable at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 KRK motives.

In another preferred embodiment of the present invention the cationic peptide stretch comprises beside the positively charged amino acid residues, in particular lysine and/or arginine residues, neutrally charged amino acid residues, in particular glycine and/or serine residues. Preferred are cationic peptide stretches consisting of about 70% to about 100%, or about 80% to about 95%, or about 85% to about 90% positively charged amino acid residues, in particular lysine, arginine and/or histidine residues, more preferably lysine and/or arginine residues and of about 0% to about 30%, or about 5% to about 20%, or about 10% to about 20% neutrally charged amino acid residues, in particular glycine and/or serine residues. Preferred are polypeptide stretches consisting of about 4% to about 8% serine residues, of about 33% to about 36% arginine residues and of about 56% to about 63% lysine residues. Especially preferred are polypeptide stretches comprising at least one motive according to SEQ ID NO: 32 (KRXKR), wherein X is any other amino acid than lysine, arginine and histidine. Especially preferred are polypeptide stretches comprising at least one motive according to SEQ ID NO: 33 (KRSKR). More preferred are cationic stretches comprising at least about 2, 3, 4, 5, 6, 7, 8, 9, 10, 11, 12, 13, 14, 15, 16, 17, 18, 19 or about 20 motives according to SEQ ID NO: 32 (KRXKR) or SEQ ID NO: 33 (KRSKR).

Also preferred are polypeptide stretches consisting of about 9 to about 16% glycine residues, of about 4 to about 11% serine residues, of about 26 to about 32% arginine residues and of about 47 to about 55% lysine residues. Especially preferred are polypeptide stretches comprising at least one motive according to SEQ ID NO: 34 (KRGSG). More preferred are cationic stretches comprising at least about 2, 3, 4, 5, 6, 7, 8, 9, 10, 11, 12, 13, 14, 15, 16, 17, 18, 19 or about 20 motives according to SEQ ID NO: 34 (KRGSG).

In another preferred embodiment of the present invention the cationic peptide stretch comprises beside the positively charged amino acid residues, in particular lysine and/or arginine residues, hydrophobic amino acid residues, in particular valine, isoleucine, leucine, methionine, phenylalanine, tryptophan, cysteine, alanine, tyrosine, histidine, threonin, serine, proline and glycine residues, more preferably alanine, valine, leucine, isoleucine, phenylalanine, and/or tryptophan residues. Preferred are cationic peptide stretches consisting of about 70% to about 100%, or about 80% to about 95%, or about 85% to about 90% positively charged amino acid residues, in particular lysine and/or arginine residues and of about 0% to about 30%, or about 5% to about 20%, or about 10% to about 20% hydrophobic amino acid residues, valine, isoleucine, leucine, methionine, phenylalanine, tryptophan, cysteine, alanine, tyrosine, histidine, threonin, serine, proline and glycine residues, more preferably alanine, valine, leucine, isoleucine, phenylalanine, and/or tryptophan residues.

Especially preferred are peptide stretches selected from the group consisting of the following sequences:

| peptide stretch | length | SEQ ID NO: |
|---|---|---|
| KRKKRK | 6 | SEQ ID NO: 10 |
| KRKKRKKRK | 9 | SEQ ID NO: 11 |
| RRRRRRRRR | 9 | SEQ ID NO: 12 |
| KKKKKKKK | 8 | SEQ ID NO: 13 |
| KRKKRKKRKK | 10 | SEQ ID NO: 14 |
| KRKKRKKRKKRK | 12 | SEQ ID NO: 15 |
| KRKKRKKRKKRKKR | 14 | SEQ ID NO: 16 |
| KKKKKKKKKKKKKKKK | 16 | SEQ ID NO: 17 |
| KRKKRKKRKKRKKRKKRKK | 19 | SEQ ID NO: 18 |
| RRRRRRRRRRRRRRRRRRR | 19 | SEQ ID NO: 19 |
| KKKKKKKKKKKKKKKKKKK | 19 | SEQ ID NO: 20 |

-continued

| peptide stretch | length | SEQ ID NO: |
|---|---|---|
| KRKKRKKRKRSKRKKRKKRK | 20 | SEQ ID NO: 21 |
| KRKKRKKRKRSKRKKRKKRKK | 21 | SEQ ID NO: 22 |
| KRKKRKKRKRKRKKRKRKKRK | 21 | SEQ ID NO: 23 |
| KRKKRKKRKRGSGKRKKRKKRK | 22 | SEQ ID NO: 24 |
| KRKKRKKRKRGSGSGKRKKRKKRK | 24 | SEQ ID NO: 25 |
| KRKKRKKRKRKRKKRKKRKKRKKRKK | 25 | SEQ ID NO: 26 |
| KRKKRKKRKRSKRKKRKKRKRSKRKKRKKRK | 31 | SEQ ID NO: 27 |
| KRKKRKKRKRGSGSGKRKKRKKRKGSGSGKRKKRKKRK | 38 | SEQ ID NO: 28 |
| KRKKRKKRKRKRKKRKKRKKRKKRKKRKKRKKRKKRKKRK | 39 | SEQ ID NO: 29 |
| KRKKRKKRKRSKRKKRKKRKRSKRKKRKKRKRSKRKKRKKRK | 42 | SEQ ID NO: 30 |

Preferably, the peptide stretch is no tag such as a His-tag, Strep-tag, Avi-tag, Myc-tag, Gst-tag, JS-tag, cystein-tag, FLAG-tag or other tags known in the art and no thioredoxin or maltose binding proteins (MBP). However, the peptide stretch and/or the modified endolysin variant according to the present invention may comprise in addition such tag or tags.

Preferably, the peptide stretch has the function to lead the modified endolysin variant according to the present invention through the outer membrane of Gram-negative bacteria but has no or only low activity when administered without being fused to the enzyme. The function to lead the modified endolysin variant through the outer membrane of Gram-negative bacteria is caused by the potential of the outer membrane or LPS disrupting activity of said peptide stretch.

Especially preferred are modified endolysin variants selected from the group consisting of the following modified endolysin variants:

| Modified endolysin variant | SEQ ID NO: (modified endolysin variant) | Endolysin part | Peptide stretch (N-terminal unless otherwise indicated) |
|---|---|---|---|
| POLY-gp144 | SEQ ID NO: 35 | SEQ ID NO: 1 | SEQ ID NO: 11 |
| (POLY)²-gp144 | SEQ ID NO: 36 | SEQ ID NO: 1 | SEQ ID NO: 21 |
| (POLY)³-gp144 | SEQ ID NO: 37 | SEQ ID NO: 1 | SEQ ID NO: 27 |
| (POLY)⁴-gp144 | SEQ ID NO: 38 | SEQ ID NO: 1 | SEQ ID NO: 30 |
| POLY-gp188 | SEQ ID NO: 39 | SEQ ID NO: 2 | SEQ ID NO: 11 |
| (POLY)²-gp188 | SEQ ID NO: 40 | SEQ ID NO: 2 | SEQ ID NO: 21 |
| (POLY)³-gp188 | SEQ ID NO: 41 | SEQ ID NO: 2 | SEQ ID NO: 27 |
| (POLY)⁴-gp188 | SEQ ID NO: 42 | SEQ ID NO: 2 | SEQ ID NO: 30 |
| pKKZ144pET32b | SEQ ID NO: 43 | SEQ ID NO: 1 | SEQ ID NO: 14 |
| KRK_6_pET32b | SEQ ID NO: 44 | SEQ ID NO: 1 | SEQ ID NO: 10 |
| KRK_12_pET32b | SEQ ID NO: 45 | SEQ ID NO: 1 | SEQ ID NO: 15 |
| KRK_14_pET32b | SEQ ID NO: 46 | SEQ ID NO: 1 | SEQ ID NO: 16 |
| R9_pET32b | SEQ ID NO: 47 | SEQ ID NO: 1 | SEQ ID NO: 12 |
| K8_pET32b | SEQ ID NO: 48 | SEQ ID NO: 1 | SEQ ID NO: 13 |
| pK2KZ144_pET32b_mod3 | SEQ ID NO: 49 | SEQ ID NO: 1 | SEQ ID NO: 28 |
| PKPSP3gp10 | SEQ ID NO: 53 | SEQ ID NO: 8 | SEQ ID NO: 11 |
| PKP2gp09 | SEQ ID NO: 57 | SEQ ID NO: 9 | SEQ ID NO: 11 |
| PKOBPgpLYS | SEQ ID NO: 61 | SEQ ID NO: 7 | SEQ ID NO: 11 |
| pK2KZ144pET32b | SEQ ID NO: 62 | SEQ ID NO: 1 | SEQ ID NO: 22 |
| pK3KZ144pET32b | SEQ ID NO: 63 | SEQ ID NO: 1 | SEQ ID NO: 27 |
| pK4KZ144pET32b | SEQ ID NO: 64 | SEQ ID NO: 1 | SEQ ID NO: 30 |
| KRK_19_pET32b | SEQ ID NO: 66 | SEQ ID NO: 1 | SEQ ID NO: 18 |
| KRK_21_pET32b | SEQ ID NO: 67 | SEQ ID NO: 1 | SEQ ID NO: 23 |
| KRK_25_pET32b | SEQ ID NO: 68 | SEQ ID NO: 1 | SEQ ID NO: 26 |
| KRK_39_pET32b | SEQ ID NO: 69 | SEQ ID NO: 1 | SEQ ID NO: 29 |
| K19_pET32b | SEQ ID NO: 70 | SEQ ID NO: 1 | SEQ ID NO: 20 |
| K16_pET32b | SEQ ID NO: 71 | SEQ ID NO: 1 | SEQ ID NO: 17 |
| pKKZ-144_K2_pET32b | SEQ ID NO: 72 | SEQ ID NO: 1 | N-terminal: SEQ ID NO: 11 C-teiminal: SEQ ID NO: 21 |
| pK2KZ144_pET32b_mod1 | SEQ ID NO: 73 | SEQ ID NO: 1 | SEQ ID NO: 24 |
| pK2KZ144_pET32b_mod2 | SEQ ID NO: 74 | SEQ ID NO: 1 | SEQ ID NO: 25 |
| smi01_KRK9 | SEQ ID NO: 75 | SEQ ID NO: 1 | SEQ ID NO: 11 |
| smi02_KRK9 | SEQ ID NO: 76 | SEQ ID NO: 1 | SEQ ID NO: 11 |
| smi03_KRK9 | SEQ ID NO: 77 | SEQ ID NO: 1 | SEQ ID NO: 11 |
| smi04_KRK9 | SEQ ID NO: 78 | SEQ ID NO: 1 | SEQ ID NO: 11 |

The modified endolysin variants according to the present invention, and thus in particular the especially preferred modified endolysin variants according to SEQ ID NO: 35 to 49, 53, 57, 61 to 64 and 66 to 78, may additional comprise a tag e.g. for purification. Preferred is a His$_6$-tag, preferably at the C-terminus of the modified endolysin variant. Said tag can be linked to the modified endolysin variant by additional amino acid residues e.g. due to cloning reasons. Preferably said tag can be linked to the modified endolysin variant by at least 1, 2, 3, 4, 5, 6, 7, 8, 9 or 10 additional amino acid residues. In a preferred embodiment the modified endolysin variant comprises a His$_6$-tag at its C-terminus linked to the modified endolysin variant by the additional amino acid residues lysine and glycine (Lys-Gly) or leucine and glutamic acid (Leu-Glu).

In particular, the modified endolysin variants as used in the examples as described below are preferred. The modified endolysin variants according to SEQ ID NO: 35 to 42, 53, 57 and 61 as used in the examples comprise a His$_6$-tag at the C-terminus linked to the respective modified endolysin variant by the additional amino acid residues lysine and glycine (Lys-Gly). The modified endolysin variants according to SEQ ID NO: 43 to 49 and 75 as used in the examples comprise a His$_6$-tag at the C-terminus linked to the respective modified endolysin variant by the additional amino acid residues leucine and glutamic acid (Leu-Glu).

Fusion proteins are constructed by linking at least two nucleic acid sequences using standard cloning techniques as described e.g. by Sambrook et al. 2001, Molecular Cloning: A Laboratory Manual. Such a protein may be produced, e.g., in recombinant DNA expression systems. Such fusion proteins according to the present invention can be obtained by fusing the nucleic acids for endolysin and the respective peptide stretch.

As some fusion proteins may either be toxic upon expression in bacteria, or not homogenous due to protein degradation, the strategy might be to express these fusion proteins fused or linked to other additional proteins. Example for these other additional protein is Thioredoxin, which was shown to mediate expression of toxic antimicrobial peptides in *E. coli* (TrxA mediating fusion expression of antimicrobial peptide CM4 from multiple joined genes in *Escherichia coli*. Zhou L, Zhao Z, Li B, Cai Y, Zhang S. Protein Expr Purif. 2009 April; 64(2):225-230).

For antimicrobial function of the fusion proteins it may be necessary to remove the additional fusion protein by proteolytic cleavage. Commercially available kits like the pET32 expression system (Novagen), may need to modify e.g. the N-terminus of the fusion depending on the protease used, like from MGS to AMGS (SEQ ID NO: 31), were the remaining alanine residue results from an introduced Enterokinase cleavage site.

In another preferred embodiment of the present invention the peptide stretches of the modified endolysin variant according to the present invention comprise modifications and/or alterations of the amino acid sequences. Such alterations and/or modifications may comprise mutations such as deletions, insertions and additions, substitutions or combinations thereof and/or chemical changes of the amino acid residues, e.g. biotinylation, acetylation, PEGylation, chemical changes of the amino-, SH- or carboxyl-groups.

The present invention further relates to an isolated nucleic acid molecule encoding the modified endolysin variant according to the present invention. The present invention further relates to a vector comprising the nucleic acid molecule according to the present invention. Said vector may provide for the constitutive or inducible expression of said modified endolysin variant according to the present invention.

The invention also relates to a method for obtaining said modified endolysin variants from a micro-organism, such as a genetically modified suitable host cell which expresses said modified endolysin variants. Said host cell may be a micro-organism such as bacteria or yeast or fungi or an animal cell as e.g. a mammalian cell, in particular a human cell. In one embodiment of the present invention the yeast cell is a *Pichia pastoris* cell. The host may be selected due to mere biotechnological reasons, e.g. yield, solubility, costs, etc. but may be also selected from a medical point of view, e.g. a non-pathological bacteria or yeast, human cells.

Another aspect of the present invention is related to a method for genetically transforming a suitable host cell in order to obtain the expression of the modified endolysin variants according to the invention wherein the host cell is genetically modified by the introduction of a genetic material encoding said modified endolysin variants into the host cell and obtain their translation and expression by genetic engineering methods well known by a person skilled in the art.

In a further aspect the present invention relates to a composition, preferably a pharmaceutical composition, comprising a modified endolysin variant according to the present invention and/or a host transformed with a nucleic acid molecule or a vector comprising a nucleotide sequence encoding a modified endolysin variant according to the present invention.

In a preferred embodiment of the present invention the composition comprises additionally agents permeabilizing the outer membrane of Gram-negative bacteria such metal chelators as e.g. EDTA, TRIS, lactic acid, lactoferrin, polymyxin, citric acid and/or other substances as described e.g. by Vaara (Agents that increase the permeability of the outer membrane. Vaara M. Microbiol Rev. 1992 September; 56(3):395-441). Also preferred are compositions comprising combinations of the above mentioned permeabilizing agents. Especially preferred is a composition comprising about 10 µM to about 100 mM EDTA, more preferably about 50 µM to about 10 mM EDTA, more preferably about 0.5 mM to about 10 mM EDTA, more preferably about 0.5 mM to about 2 mM EDTA, more preferably about 0.5 mM to 1 mM EDTA. However, also compositions comprising about 10 µM to about 0.5 mM EDTA are preferred. Also preferred is a composition comprising about 0.5 mM to about 2 mM EDTA, more preferably about 1 mM EDTA and additionally about 10 to about 100 mM TRIS.

The present invention also relates to a modified endolysin variant according to the present invention and/or a host transformed with a nucleic acid comprising a nucleotide sequence encoding a modified endolysin variant according to the present invention for use as a medicament.

In a further aspect the present invention relates to the use of a modified endolysin variant according to the present invention and/or a host transformed with a vector comprising a nucleic acid molecule comprising a nucleotide sequence encoding a modified endolysin variant according to the present invention in the manufacture of a medicament for the treatment and/or prevention of a disorder, disease or condition associated with pathogenic Gram-negative bacteria. In particular the treatment and/or prevention of the disorder, disease or condition may be caused by Gram-negative bacteria of bacterial groups, families, genera or species comprising strains pathogenic for humans or animals like Enterobacteriaceae (*Escherichia*, especially *E. coli*,

*Salmonella, Shigella, Citrobacter, Edwardsiella, Enterobacter, Hafnia, Klebsiella*, especially *K. pneumoniae, Morganella, Proteus, Providencia, Serratia, Yersinia*), Pseudomonadaceae (*Pseudomonas*, especially *P. aeruginosa, Burkholderia, Stenotrophomonas, Shewanella, Sphingomonas, Comamonas*), *Neisseria, Moraxella, Vibrio, Aeromonas, Brucella, Francisella, Bordetella, Legionella, Bartonella, Coxiella, Haemophilus, Pasteurella, Mannheimia, Actinobacillus, Gardnerella*, Spirochaetaceae (*Treponema* and *Borrelia*), Leptospiraceae, *Campylobacter, Helicobacter, Spirillum, Streptobacillus*, Bacteroidaceae (*Bacteroides, Fusobacterium, Prevotella, Porphyromonas*), *Acinetobacter*, especially *A. baumanii* . Preferably, said disorder, disease or condition may be caused by *Pseudomonas*, in particular *Pseudomonas aeruginosa* and/or *Pseudomonas putida, Burkholderia*, in particular *Burkholderia pseudomallei* and/or *Burkholderia solanacearum, Salmonella*, in particular *Salmonella typhimurium* and/or *Salmonella Enteritidis, Acinetobacter*, in particular *Acinetobacter baumannii, Escherichia coli* and/or *Klebsiella*, in particular *Klebsiella pneumoniae.*

The present invention further relates to a medicament comprising a modified endolysin variant according to the present invention and/or a host transformed with a nucleic acid comprising a nucleotide sequence encoding a modified endolysin variant according to the present invention.

In a further aspect the present invention relates to a method of treating a disorder, disease or condition in a subject in need of treatment and/or prevention, which method comprises administering to said subject an effective amount of a modified endolysin variant according to the present invention and/or an effective amount of a host transformed with a nucleic acid comprising a nucleotide sequence encoding a modified endolysin variant according to the present invention or a composition according to the present invention. The subject may be a human or an animal.

Preferably said method of treatment may be for the treatment and/or prevention of infections caused by Gram-negative bacteria, in particular by the Gram-negative bacteria as listed above. In particular said method of treatment may be for the treatment and/or prevention of infections of the skin, of soft tissues, the respiratory system, the lung, the digestive tract, the eye, the ear, the teeth, the nasopharynx, the mouth, the bones, the vagina, of wounds of bacteraemia and/or endocarditis caused by Gram-negative bacteria, in particular by the Gram-negative bacteria as listed above.

The dosage and route of administration used in a method of treatment (or prophylaxis) according to the present invention depends on the specific disease/site of infection to be treated. The route of administration may be for example oral, topical, nasopharyngeal, parenteral, inhalational, intravenous, intramuscular, intrathecal, intraspinal, endobronchial, intrapulmonal, intraosseous, intracardial, intraarticular, rectal, vaginal or any other route of administration.

For application of a modified endolysin variant according to the present invention and/or an effective amount of a host transformed with a nucleic acid comprising a nucleotide sequence encoding a modified endolysin variant according to the present invention or a composition according to the present invention to a site of infection (or site endangered to be infected) a formulation may be used that protects the active compounds from environmental influences such as proteases, oxidation, immune response etc., until it reaches the site of infection. Therefore, the formulation may be capsule, dragee, pill, powder, suppository, emulsion, suspension, gel, lotion, cream, salve, injectable solution, syrup, spray, inhalant or any other medical reasonable galenic formulation. Preferably, the galenic formulation may comprise suitable carriers, stabilizers, flavourings, buffers or other suitable reagents. For example, for topical application the formulation may be a lotion, cream, gel, salve or plaster, for nasopharyngeal application the formulation may be saline solution to be applied via a spray to the nose. For oral administration in case of the treatment and/or prevention of a specific infection site e.g. in the intestine, it can be necessary to protect a modified endolysin variant according to the present invention from the harsh digestive environment of the gastrointestinal tract until the site of infection is reached. Thus, bacteria as carrier, which survive the initial steps of digestion in the stomach and which secret later on a modified endolysin variant according to the present invention into the intestinal environment can be used.

In a specific embodiment of the present invention the use of a modified endolysin variant according to the present invention and/or a host transformed with a vector comprising a nucleic acid molecule comprising a nucleotide sequence encoding a modified endolysin variant according to the present invention in the manufacture of a medicament for the treatment and/or prevention of a disorder, disease or condition caused by *Pseudomonas*, particularly by *Pseudomonas aeruginosa* in particular intestinal affections, in particular in infants, infections of the meninges, e.g. meningitis haemorrhagica, infections of the middle ear, the skin (Ecthyma gangraenosum), in particular burns, the urinary tract, rhinitis, bacteremic pneumonia, in particular wherein the patient is suffering from cystic fibrosis or hematologic malignancies such as leukemia, or with neutropenia from immunosuppressive therapy, septicemia, in particular because of long-term intravenous or urinary catheterization, invasive surgical procedures and severe burns, endocarditis, in particular wherein the patient is a intravenous drug user or a patient with complications from open heart surgery, highly destructive ocular infections, in particular after the use of contaminated ophthalmologic solutions or severe facial burns, osteochondritis, in particular as a result of severe trauma or puncture wounds through contaminated clothing.

In another specific embodiment of the present invention the disorder, disease or condition is caused by *Burkholderia pseudomallei*, in particular Whitmore's Disease, chronic pneumonia, septicemia, in particular wherein the patient has a traumatized skin lesion.

In another specific embodiment of the present invention the disorder, disease or condition is caused by *Salmonella thyphimurium* and *Salmonella enteritidis*, in particular acute gastroenteritis and local purulent processes, particularly osteomyelitis, endocarditis, cholecystitis and especially caused by *Salmonella thyphimurium* meningitis, in particular wherein the patient is less than two years old.

In another specific embodiment of the present invention the disorder, disease or condition is caused by *Acinetobacter baumannii*, in particular bronchitis, pneumonia, wound infections and septicemia, in particular as a result of intravenous catheterization.

In another specific embodiment of the present invention the disorder, disease or condition is caused by *Escherichia coli*, in particular extra intestinal infections, particularly appendicitis, purulent cholecystitis, peritonitis, purulent meningitis and infection of the urinary tract, intraintestinal *E. coli* infections, particularly epidemic enteritis, and infectious disease similar to dysentery, septicemia, enterotoxemia, mastitis and dysentery.

In another specific embodiment of the present invention the disorder, disease or condition is caused by *Klebsiella*

*pneumoniae*, in particular pneumonia, bacteremia, meningitis and infections of the urinary tract.

Preferably, a modified endolysin variant according to the present invention is used for medical treatment, if the infection to be treated (or prevented) is caused by multiresistant bacterial strains, in particular by strains resistant against one or more of the following antibiotics: streptomycin, tetracycline, cephalothin, gentamicin, cefotaxime, cephalosporin, ceftazidime or imipenem. Furthermore, a modified endolysin variant according to the present invention can be used in methods of treatment by administering it in combination with conventional antibacterial agents, such as antibiotics, lantibiotics, bacteriocins or endolysins, etc.

The present invention also relates to a pharmaceutical pack comprising one or more compartments, wherein at least one compartment comprises one or more modified endolysin variant according to the present invention and/or one or more hosts transformed with a nucleic acid comprising a nucleotide sequence encoding a modified endolysin variant according to the present invention or a composition according to the present invention.

In another aspect the present invention relates to a process of preparation of a pharmaceutical composition, said process comprising admixing one or more modified endolysin variant according to the present invention and/or one or more hosts transformed with a nucleic acid comprising a nucleotide sequence encoding a modified endolysin variant according to the present invention with a pharmaceutically acceptable diluent, excipient or carrier.

In an even further aspect the composition according to the present invention is a cosmetic composition. Several bacterial species can cause irritations on environmentally exposed surfaces of the patient's body such as the skin. In order to prevent such irritations or in order to eliminate minor manifestations of said bacterial pathogens, special cosmetic preparations may be employed, which comprise sufficient amounts of the modified endolysin variant according to the present invention in order to degrade already existing or freshly settling pathogenic Gram-negative bacteria.

In a further aspect the present invention relates to the modified endolysin variant according to the present invention for use as diagnostic means in medicinal, food or feed or environmental diagnostics, in particular as a diagnostic means for the diagnostic of bacteria infection caused in particular by Gram-negative bacteria. In this respect the modified endolysin variant according to the present invention may be used as a tool to specifically degrade pathogenic bacteria, in particular Gram-negative pathogenic bacteria. The degradation of the bacterial cells by the modified endolysin variant according to the present invention can be supported by the addition of detergents like Triton X-100 or other additives which weaken the bacterial cell envelope like polymyxin B. Specific cell degradation is needed as an initial step for subsequent specific detection of bacteria using nucleic acid based methods like PCR, nucleic acid hybridization or NASBA (Nucleic Acid Sequence Based Amplification), immunological methods like IMS, immunofluorescence or ELISA techniques, or other methods relying on the cellular content of the bacterial cells like enzymatic assays using proteins specific for distinct bacterial groups or species (e.g. β-galactosidase for enterobacteria, coagulase for coagulase positive strains).

In a further aspect the present invention relates to the use of the modified endolysin variant according to the present invention for the removal, reduction and/or prevention of Gram-negative bacterial contamination of foodstuff, of food processing equipment, of food processing plants, of surfaces coming into contact with foodstuff such as shelves and food deposit areas and in all other situations, where pathogenic, facultative pathogenic or other undesirable bacteria can potentially infest food material, of medical devices and of all kind of surfaces in hospitals and surgeries.

In particular, a modified endolysin variant of the present invention may be used prophylactically as sanitizing agent. Said sanitizing agent may be used before or after surgery, or for example during hemodialysis. Moreover, premature infants and immunocompromised persons, or those subjects with need for prosthetic devices may be treated with a modified endolysin variant according to the present invention. Said treatment may be either prophylactically or during acute infection. In the same context, nosocomial infections, especially by antibiotic resistant strains like *Pseudomonas aeruginosa* (FQRP), *Acinetobacter* species and Enterobacteriaceae such as *E. coli, Salmonella, Shigella, Citrobacter, Edwardsiella, Enterobacter, Hafnia, Klebsiella, Morganella, Proteus, Providencia, Serratia* and *Yersinia* species may be treated prophylactically or during acute phase with a modified endolysin variant of the present invention. Therefore, a modified endolysin variant according to the present invention may be used as a disinfectant also in combination with other ingredients useful in a disinfecting solution like detergents, tensids, solvents, antibiotics, lantibiotics, or bacteriocins.

For the use of the modified endolysin variant according to the present invention as a disinfectant e.g. in hospital, dental surgery, veterinary, kitchen or bathroom, the modified endolysin variant can be prepared in a composition in form of e.g. a fluid, a powder, a gel, or an ingredient of a wet wipe or a disinfection sheet product. Said composition may additionally comprise suitable carrier, additives, diluting agents and/or excipients for its respective use and form, respectively,—but also agents that support the antimicrobial activity like EDTA or agents enhance the antimicrobial activity of the fusion proteins. The fusion protein may also be used with common disinfectant agents like, Alcohols, Aldehydes, Oxidizing agents, Phenolics, Quaternary ammonium compounds or UV-light. For disinfecting for example surfaces, objects and/or devices the modified endolysin variant can be applied on said surfaces, objects and/or devices. The application may occur for instance by wetting the disinfecting composition with any means such as a cloth or rag, by spraying, pouring. The fusion proteins may be used in varying concentration depending on the respective application and the "reaction time" intended to obtain full antimicrobial activity.

Further scope of applicability of the present invention will become apparent from the detailed description given hereinafter, however, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

The following examples explain the present invention but are not considered to be limiting. Unless indicated differently, molecular biological standard methods were used, as e.g., described by Sambrock et al., 1989, Molecular Cloning:

A Laboratory Manual, 2nd edition, Cold Spring Harbor Laboratory Press, Cold Spring Harbor, N.Y.

EXAMPLE 1

Cloning, Expression and Purification of Modified phiKZgp144 and ELgpgp188 Endolysin Variants phiKZgp144 as depicted in SEQ ID NO: 1 and ELgp188 as depicted in SEQ ID NO: 2 are modular endolysins originating from *Pseudomonas aeruginosa* phages φKZ and EL with an N-terminal peptidoglycan binding and C-terminal catalytic domain (Briers et al., 2007).

For the amplification of the open reading frame (ORF) of phiKZgp144 and ELgp188 PCR a standard 5' primer (for phiKZgp144: 5' ATGAAAGTATTACGCAAA 3' (SEQ ID NO: 83); for ELgp188 5' ATGAACTTCCGGACGAAG 3' (SEQ ID NO: 65)) and the standard 3' primers according to SEQ ID NO: 81 and 82 were applied (for phiKZgp144: TTTTCTATGTGCTGCAAC (SEQ ID NO: 81); for ELgp188: ATACGAAAT AACGTGACGA (SEQ ID NO: 82)) was used. To extend the 5' end of the open reading frame encoding phiKZgp144 or ELgp188 with a gene fragment encoding nine positively charged residues (Lys-Arg-Lys-Lys-Arg-Lys-Lys-Arg-Lys—SEQ ID NO: 11) a tail PCR with an extended 5' primer (for phiKZgp 144: 5' ATGGGATCCAAACGCAAGAAACGTAAGAAA CGCAAAAAAGTATTACGCAAAG 3' (SEQ ID NO 79); for ELgp188: 5' ATGGGATCCAAACGCAAGAAACG-TAAGAAA CGCAAAAACTTCCGGACGAAG 3' (SEQ ID NO: 80)) and the standard 3' primers according to SEQ ID NO: 81 and 82 were applied. The PCR product was cloned in the pEXP5CT/TOPO® expression vector (Invitrogen, Carlsbad, Calif., USA) according to the protocol of the manufacturer. Arginine triplets were incorporated besides lysine triplets to avoid tRNA depletion and reduce the risk of frameshifts (the only two available triplets for lysine are AAA and AAG, leading to long A-stretches). Insertion of additional polycationic cassettes into the designed BamHI restriction site lengthens the tail with extra cationic residues. This insertion creates an arginine and serine triplet at each junction site (FIG. 1). Up to four polycationic peptide stretches were fused to both phiKZgp144 and ELgp188, designated (POLY)$^n$-gp144 or (POLY)$^n$-gp188 (n=1,2,3,4), comprising respectively 9, 19, 29 and 39 positively charged amino acid residues in the N-terminus. Accordingly, the following constructs were expressed in *E. coli* BL21 (DE3) pLysS cells (exponentially growing cells at 37° C., induction using 1 mM IPTG, expression for 4 h at 37° C.):

| Modified endolysin variant | SEQ ID NO: | Number of positively charged amino acid residues |
|---|---|---|
| POLY-gp144 | SEQ ID NO: 35 | 9 |
| (POLY)$^2$-gp144 | SEQ ID NO: 36 | 19 |
| (POLY)$^3$-gp144 | SEQ ID NO: 37 | 29 |
| (POLY)$^4$-gp144 | SEQ ID NO: 38 | 39 |
| POLY-gp188 | SEQ ID NO: 39 | 9 |
| (POLY)$^2$-gp188 | SEQ ID NO: 40 | 19 |
| (POLY)$^3$-gp188 | SEQ ID NO: 41 | 29 |
| (POLY)$^4$-gp188 | SEQ ID NO: 42 | 39 |

The modified endolysin variants POLY-gp 144 (SEQ ID NO: 35), (POLY)$^2$-gp 144 (SEQ ID NO: 36), POLY-gp188 (SEQ ID NO: 39) and (POLY)$^2$-gp188 (SEQ ID NO: 40) have been used for further investigations. Said proteins were purified by Ni$^{2+}$ affinity chromatography using the C-terminal 6× His-tag (Akta Fast Protein Liquid Chromatography using 1 ml His-trap Ni-NTA columns). The total yields per liter *E. coli* expression culture were determined by spectrophotometric measurement of the protein concentration and the total volume of the purified stock solution. The purification of gp188 derivatives was performed under more stringent conditions (65 mM imidazole) compared to gp144 derivatives (50 mM imidazole) to ensure high purity. The total yields per liter *E. coli* expression culture are shown in table 1.

TABLE 1

Yields of recombinant purification of endolysin derivatives per liter *E. coli* expression culture.

| | Endolysin | |
|---|---|---|
| Fusion | phiKZgp144 | ELgp188 |
| POLY | 2 mg | 48 mg |
| (POLY)$^2$ | 0.5 mg | 0.06 mg |

Purified stock solutions were ~90% pure. Mass spectrometric analysis of purified solutions of POLY-derivatives revealed traces of the *E. coli* 50S ribosomal subunit protein L2 and 16S rRNA uridine-516 pseudo-uridylate synthase. All phiKZgp144 derivatives showed multimer formation which could be converted to monomers by addition of β-mercaptoethanol, indicating that interdisulfide bonds cause multimerization.

EXAMPLE 2

Antibacterial Activity of Modified phiKZgp144 and ELgp188 Variants

Exponential (~10$^6$/ml) *P. aeruginosa* PAO1p cells (Pirnay J P et al. (2003), *J Clin Microbiol.*, 41(3):1192-1202) were 100× diluted (final density was ~10$^6$/ml) and incubated at room temperature with each 10 μg undialyzed protein (unmodified endolysins phiKZgp 144 (SEQ ID NO: 1) and ELpg188 (SEQ ID NO: 2) and modified endolysin variants POLY-gp144 (SEQ ID NO:35), (POLY)$^2$-gp144 (SEQ ID NO: 36), POLY-gp188 (SEQ ID NO: 39) and (POLY)$^2$-gp188 (SEQ ID NO: 40) at a final concentration of 100 μg/ml in buffer (20 mM NaH$_2$PO$_4$-NaOH pH7.4; 0.5 M NaCl; 0.5 M imidazole). After 1 hour cell suspensions were diluted in PBS buffer (10e-5, 10e-4 and 10e-3) and plated (standard LB-medium, incubated overnight at 37° C.). Additionally, a negative control containing cells in PBS buffer was plated. The residual colonies were counted after an overnight incubation. Based on the counted cell numbers the antibacterial activity as the relative inactivation (%) (=100−(N$_i$/No)*100 with N$_0$=number of untreated cells and N$_i$=number of treated cells) and in logarithmic units (=log$_{10}$N$_0$/N$_i$) was calculated (Table 2). All samples were replicated in six fold. Averages/standard deviations are represented. Statistical analysis was performed using a student's t-test.

Unmodified endolysins phiKZgp144 and ELgp188 do not reduce cell numbers significantly compared to the negative control. This observation illustrates the efficacy of the outer membrane as a barrier for the endolysin to degrade the cell wall of the Gram-negative bacteria. In contrast as shown in Table 2 the incubation with the modified endolysins POLY-gp144, (POLY)$^2$-gp144, POLY-gp188 and (POLY)$^2$-gp188 causes a significant reduction (α=0.05) of the bacterial cell number (99.85±0.09% for POLY-gp144 and 98.0±0.2% for POLY-gp188). An increase of the length of the polycationic peptide stretch further tends to strengthen the antibacterial activity, especially in case of phiKZgp144 (a reduction up to 99.98±0.02% or 3.7±0.3 log units is achieved within 1 hour for (POLY)²-gp144). Moreover, the experiments demonstrated that the modified endolysins of phiKZgp 144 have a higher antibacterial activity than the modified endolysins of ELgp188.

TABLE 2

Antibacterial effect of endolysins unmodified and modified phiKZgp144 and ELgp188 variants.

| Exponentially growing cells | Endolysins | | | |
|---|---|---|---|---|
| | phiKZgp144 | | ELgp188 | |
| | % | log | % | log |
| unmodified endolysin | 0 ± 15 | 0.00 ± 0.06 | 10 ± 13 | 0.05 ± 0.06 |
| POLY | 99.85 ± 0.09 | 2.9 ± 0.3 | 98.0 ± 0.2 | 1.7 ± 0.1 |
| (POLY)² | 99.98 ± 0.02 | 3.7 ± 0.3 | 98.9 ± 0.4 | 2.0 ± 0.2 |

Thus, the example demonstrated that the addition of a short peptide stretch of nine cationic residues N-terminally to phiKZgp144 (SEQ ID NO: 1) is already sufficient to kill almost 99.9% of the cells within 1 hour. Poly-L-Lysine has intrinsic antibacterial activity as well, although this property is so far only ascribed to polymers of at least 20 residues (Vaara and Vaara, 1983a, 1983b). However, the concerted action of the polycationic peptide stretch and the endolysin kills the cells.

In a further experiment the modified endolysin POLY-gp 144 was dialyzed to 50 mM $KH_2PO_4/K_2HPO_4$ pH 7 and used instead of undialyzed protein solution as described above. Thereby, the inactivation level was additionally increased from 2.9±0.3 log units to 3.9±0.2 log units.

EXAMPLE 3

Expression of Modified phiKZgp144 and ELgp188 Variants in *Pichia pastoris* as a Host for Non-Toxic Recombinant Production The open reading frame encoding POLY-gp144 (SEQ ID NO: 35) was cloned in the pPICZαA shuttle vector (Invitrogen), which was subsequently integrated in the *P. pastoris* genome by homologous recombination (as indicated by the manufacturer; *P. pastoris* X33 cells, Invitrogen). Gene expression was induced with methanol (1%) in BMMY-medium and the supernatant was analyzed for the presence of enzymatic activity after 1, 3 and 4 days. Therefore, an amount of 30 μl supernatant of the *P. pastoris* expression culture was added to 270 μl chloroform-permeabilized *P. aeruginosa* PAO1p cells (Pirnay JP et al. (2003), *J Clin Microbiol.*, 41(3):1192-1202) after 1, 3 and 4 days (buffer condition: $KH_2PO_4/K_2HPO_4$ I=120 mM pH 6.2). Subsequently, the optical density was spectrophotometrically recorded (FIG. 2). A drop in optical density indicates the secretion of a muralytic enzyme by *P. pastoris*. As a negative control, *P. pastoris* X33 without expression plasmid was included. Thus, the lysis of the substrate upon addition of the supernatants sample is a measure for successful recombinant production and secretion of POLY-gp144 (SEQ ID NO: 35) by *P. pastoris*. After 1 day, a limited enzymatic activity could be detected. The maximum activity was observed after 3 days since no significant increase of activity in the supernatants was observed at the fourth day. No toxic effect on the cell density of *P. pastoris* was observed.

During expression by *P. pastoris* the α-secretion signal of the vector causes secretion of the recombinant protein to the surrounding media, which allows a simplify purification since only a limited number of other proteins is secreted. A BamHI restriction site in the 5' end of the open reading frames enables the addition of more cassettes encoding additional polycationic peptide stretches.

EXAMPLE 4

Further Modified Endolysin phiKZgp144 Variants with Different Polycationic Peptide Stretches To test and to compare the potential of polycationic peptides variants of phiKZgp144 and other endolysin encoding genes were synthesised having different polycationic peptides at the N-terminal end of the protein. Peptide stretch variation concerns length, composition and insertion of linker sequences. On the one hand further polycationic peptide stretches having N-terminal multiples of the KRK motive were produced. On the other hand polycationic peptide stretches consisting only of arginine (R) or lysine (K) were produced. Moreover, to enhance the translation of long polycationic peptide stretches, polycationic peptide stretches comprising a linker sequence were produced.

The different products were cloned in the pET32b expression vector (Novagen, Darmstadt, Germany). pET32b was used to reduce potential toxicity of the polycationic peptide against the *E. coli* host. A vector-encoded fusion protein (thioredoxin) masks the polycationic peptide and can be eliminated during the purification process.

Accordingly, the following modified endolysin variants were expressed in *E. coli* BL21 (DE3) cells at 37° C. until an optical density of OD600 nm=0.6 was reached. Then protein expression was induced with 1 mM IPTG (final concentration) and expression was preformed for four hours. Then *E. coli* cells were harvested by centrifugation for 20 min at 6000 g and cell disruption and protein purification was performed according the S-tag purification kit (Novagen, Darmstadt, Germany):

| Modified endolysin variant | peptide stretch's length | Sequence of the peptide stretch |
|---|---|---|
| phiKZgp144 (SEQ ID NO: 1) | 0 | — |
| pKKZ144pET32b (SEQ ID NO: 43) | 10 | KRKKRKKRKK (SEQ ID NO: 14) |
| KRK_6_pET32b (SEQ ID NO: 44) | 6 | KRKKRK (SEQ ID NO: 10) |
| KRK_12_pET32b (SEQ ID NO: 45) | 12 | KRKKRKKRKKRK (SEQ ID NO: 15) |
| KRK_14_pET32b (SEQ ID NO: 46) | 14 | KRKKRKKRKKRKKR (SEQ ID NO: 16) |
| R9_pET32b (SEQ ID NO: 47) | 9 | RRRRRRRRR (SEQ ID NO: 12) |

-continued

| Modified endolysin variant | peptide stretch's length | Sequence of the peptide stretch |
|---|---|---|
| K8_pET32b (SEQ ID NO: 48) | 8 | KKKKKKKK (SEQ ID NO: 13) |
| pK2KZ144_pET32b_mod3 (SEQ ID NO: 49) | 38 | KRKKRKKRKRGSGSGKRKK RKKRKGSGSGKRKKRKKRK (SEQ ID NO: 28) |

All proteins were purified using the S-Tag™ rEK Purification Kit (Novagen, Darmstadt, Germany). Using the pET32b vector, the expressed proteins were not toxic to the host resulting in high yields of produced protein. Purified stock solutions showed high purity.

Exponential (~$10^6$/ml) P. aeruginosa PAO1p cells (Burn wound isolate, Queen Astrid Hospital, Brussels; Pirnay J P et al. (2003), J Clin Microbiol., 41(3):1192-1202) were 100× diluted (final density was ~$10^6$/ml) incubated at room temperature with each 10 μg undialyzed protein as listed above at a final concentration of 100 μg/ml in buffer (20 mM $NaH_2PO_4$-NaOH pH7.4; 0.5 M NaCl; 0.5 M imidazole). After 1 hour cell suspensions were diluted 1:100 and plated on LB. Additionally, a negative control was plated using buffer (20 mM $NaH_2PO_4$-NaOH pH7.4; 0.5 M NaCl; 0.5 M imidazole). The residual colonies were counted after an overnight incubation at 37° C. Based on the counted cell numbers the antibacterial activity as the relative inactivation (%) (=100−($N_f$/No)*100 with $N_0$=number of untreated cells and $N_f$=number of treated cells) was calculated (Table 3). All samples were replicated at least in four fold.

TABLE 3

Antibacterial effect of endolysins unmodified and modified phiKZgp144 and ELgp188

| Modified endolysin variant | Sequence of the peptide stretch | Reduction [%] |
|---|---|---|
| phiKZgp144 (SEQ ID NO: 1) | | 0 |
| pKKZ144pET32b (SEQ ID NO: 43) | KRKKRKKRKK (SEQ ID NO: 14) | 99-99.9 |
| KRK_6_pET32b (SEQ ID NO: 44) | KRKKRK (SEQ ID NO: 10) | 99.9 |
| KRK_12_pET32b (SEQ ID NO: 45) | KRKKRKKRKKRK (SEQ ID NO: 15) | 99-99.9 |
| KRK_14_pET32b (SEQ ID NO: 46) | KRKKRKKRKKRKKR (SEQ ID NO: 16) | 99.9 |
| R9_pET32b (SEQ ID NO: 47) | RRRRRRRRR (SEQ ID NO: 12) | 99 |
| K8_pET32b (SEQ ID NO: 48) | KKKKKKKK (SEQ ID NO: 13) | 99 |
| pK2KZ144_pET32b_mod3 (SEQ ID NO: 49) | KRKKRKKRKRGSGSGKRKK RKKRKGSGSGKRKKRKKRK (SEQ ID NO: 28) | 99.9 |

Unmodified phiKZgp144 does not reduce cell numbers significantly compared to the negative control. Beyond that, modified phiKZgp144 variants wearing a polycationic peptide of N-terminal multiples of the KRK motive enhance the antimicrobial effect immensely. However, also variants having a homomer peptide stretch of lysine or arginine show significant reduction of cells compared with unmodified phiKZgp144 as measured. Moreover, also the variant having a polycationic peptide stretch of 38 amino acid residues and comprising a linker sequence enhance the antimicrobial effect immensely.

EXAMPLE 5

Modified Endolysin Variants of Salmonella typhimurium Phage PSP3

PSP3gp10 according to SEQ ID NO: 8 is a globular endolysin with 165 amino acid residues originating from Salmonella typhimurium phage PSP3 with a catalytic lambda-like muramidase domain. As predicted by BLASTp and Pfam analysis the PSP3gp10 endolysin comprises its catalytic domain in the range of about amino acid residue 34 to about amino acid residue 152.

Purified genomic DNA of phage PSP3 was used as a template for the amplification of the open reading frame (ORF) of PSP3gp10 in a Hot Start Taq polymerase PCR reaction (Qiagen, Germany) using the following PCR parameters:

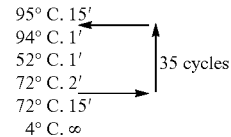

For said PCR a standard 5' primer (5' ATGGGATCCCCG-GTCATTAATACTCACCAG 3' (SEQ ID NO: 50)) and a standard 3' primer (5' TGCCATCACCCCGCCAGCCGTG 3' (SEQ ID NO: 51)) was used. To extend the 5' end of the ORF which encodes PSP3gp10 with a gene fragment encoding the polycationic 9-mer peptide Lys-Arg-Lys-Lys-Arg-Lys-Lys-Arg-Lys (SEQ ID NO: 11) a tail PCR (Hot Start Taq polymerase PCR with same parameters) with an extended 5' primer (5' ATGGGATCCAAACGCAAGAAACGTAA GAAACGCAAACCGGTCATTAATACTCACCAG 3' (SEQ ID NO: 52)) and the standard 3' primer according to SEQ ID NO: 51 was applied. Both the original unmodified PSP3gp10 PCR fragment and the PK-extended fragment were ligated in the pEXP5CT/TOPO® expression vector (Invitrogen, Carlsbad, Calif., USA) by following the TA-cloning protocol of the manufacturer.

Recombinant expression of PSP3gp10 according to SEQ ID NO: 8 and PKPSP3gp10 according to SEQ ID NO: 53 is performed in exponentially growing E. coli BL21 (λDE3) pLysS cells (Invitrogen) after induction with 1 mM IPTG (isopropylthiogalactoside) at 37° C. for a period of 4 hours. Both proteins were purified by $Ni^{2+}$ affinity chromatography (Akta FPLC, GE Healthcare) using the C-terminal 6× His-tag, encoded by the pEXP5CT/TOPO® expression vector. The $Ni^{2+}$ affinity chromatography is performed in 4 subsequent steps, all on room temperature:

1. Equilibration of the Histrap HP 1 ml column (GE Healthcare) with 10 column volumes of Washing Buffer (60 mM imidazole, 0.5 mM NaCl and 20 mM $NaH_2PO_4$-NaOH on pH 7.4) at a flow rate of 0.5 ml/min.
2. Loading of the total lysate (with wanted endolysin) on the Histrap HP 1 ml column at a flow rate of 0.5 ml/min.

3. Washing of the column with 15 column volumes of Washing Buffer at a flow rate of 1 ml/min.
4. Elution of bounded endolysin from the column with 10 column volumes of Elution Buffer (500 mM imidazole, 5 mM NaCl and 20 mM $NaH_2PO_4$-NaOH on pH 7.4) at a flow rate of 0.5 ml/min The total yields of both purified recombinant proteins per liter E. coli expression culture shown in Table 4. The values were determined by spectrophotometric measurement of the protein concentration and the total volume of the purified stock solution at a wavelength of 280 nm. Purified stock solutions consisting of PSP3gp10 and PKPSP3gp10, respectively, in Elution Buffer (20 mM $NaH_2PO_4$-NaOH pH7.4; 0.5 M NaCl; 500 mM imidazole) were at least 90% pure as determined visually on SDS-PAGE gels.

TABLE 4

Yields of purified recombinant PSP3gp10 endolysin and its modified variant PKPSP3gp10 per liter E. coli expression culture.

| Endolysins | Expression yield |
|---|---|
| PSP3gp10 (SEQ ID NO: 8) | 2.15 mg |
| PKPSP3gp10 (SEQ ID NO: 53) | 5.56 mg |

To determine the anti-Gram-negative spectrum of the PKPSP3gp10 endolysin according to SEQ ID NO: 53, a combination of 1.315 µM PKPSP3gp10 endolysin and 0.5 mM EDTA was tested on the clinical P. aeruginosa strains PAO1p and Br667, Escherichia coli WK6, and Salmonella typhimurium (see Table 5). Exponential growing bacterial cells ($OD_{600\ nm}$ of 0.6) were 100-fold diluted to a final density of about $10^6$/ml of each strain were incubated for 30 minutes at room temperature without shaking with unmodified endolysin PSP2gp10 (SEQ ID NO: 8) and modified endolysin PKPSP3gp10 (SEQ ID NO: 53) each in combination without and with 0.5 mM EDTA. For incubation, the endolysins were used each in buffer (20 mM $NaH_2PO_4$-NaOH pH7.4; 0.5 M NaCl; 0.5 M imidazole) and the incubation took place at a final concentration of endolysin of 1.315 µM. As a control each strain was also incubated for 30 minutes with 0.5 mM EDTA (in same buffer as outlined above) but no endolysin.

TABLE 5

List of used Gram-negative strains

| Gram-negative strain | Source | Reference |
|---|---|---|
| Pseudomonas aeruginosa PAO1p | Burn wound isolate, Queen Astrid Hospital, Brussels | Pirnay et al., 2003* |
| Pseudomonas aeruginosa Br667 | Burn wound isolate, Queen Astrid Hospital, Brussels | Pirnay et al., 2003* |
| Escherichia coli WK6 | Standard laboratory expression strain | Prof. C. Michiels |
| Salmonella typhimurium LT2 | SGSC N° 2317 | Prof. C. Michiels |

*Pirnay J P et al. (2003). Molecular epidemiology of Pseudomonas aeruginosa colonization in a burn unit: persistence of a multidrug-resistant clone and a silver sulfadiazine-resistant clone. J Clin Microbiol., 41(3): 1192-1202.

After incubation cell suspensions were diluted three times (respectively $10^5$-$10^4$-$10^3$ cells/ml) and 100 µl of each dilution was plated out on LB-medium. The residual colonies were counted after an overnight incubation on 37° C. Based on the counted cell numbers the antibacterial activity as the relative inactivation in logarithmic units (=$\log_{10} N_0/N_i$ with $N_0$=number of untreated cells and $N_i$=number of treated cells) was calculated (Table 6).

TABLE 6

Antibacterial activity of unmodified endolysin (PSP3gp10) and its modified endolysin variant (PKPSP3gp10) with and without EDTA-$Na_2$ on different exponential growing Gram-negative species.

|  | 0.5 mM EDTA | 1.315 µM PSP3gp10 | 1.315 µM PKPSP3gp10 | 1.315 µM PSP3gp10 + 0.5 mM EDTA | 1.315 µM PKPSP3gp10 + 0.5 mM EDTA |
|---|---|---|---|---|---|
| P. aeruginosa PAO1p | 0.146 +/− 0.002 | 0.383 +/− 0.015 | 0.344 +/− 0.163 | 3.552 +/− 0.536 | >4.146 |
| P. aeruginosa Br667 | 0.223 +/− 0.038 | 0.375 +/− 0.056 | 0.353 +/− 0.086 | 0.571 +/− 0.035 | 0.891 +/− 0.118 |
| Salmonella typhimurium | 0.104 +/− 0.049 | 0.283 +/− 0.038 | 0.327 +/− 0.057 | 0.690 +/− 0.036 | 0.850 +/− 0.032 |
| Escherichia coli WK6 | 0.393 +/− 0.035 | 0.190 +/− 0.029 | 0.205 +/− 0.088 | 0.387 +/− 0.014 | 0.584 +/− 0.024 |

All samples were replicated in threefold. Averages+/− standard deviations are represented. The maximal reduction observed is dependent on the detection level of 10 cells/ml and the initial cell density. For PAO1p, EDTA works synergistically with both the unmodified PSP3gp10 endolysin and its modified variant PKPSP3gp10.

EXAMPLE 6

Modified Endolysin Variants of Escherichia coli Phage P2

P2gp09 according to SEQ ID NO: 9 is a globular endolysin of 165 amino acid residues originating from Escherichia coli phage P2 with a catalytic lambda-like muramidase domain. As predicted by BLASTp and Pfam analysis the P2gp09 endolysin comprises its catalytic domain in the range of about amino acid residue 34 to about amino acid residue 152.

Purified genomic DNA of phage P2 was used as a template for the amplification of the open reading frame (ORF) of P2gp09 in standard PCR reaction with Pfu polymerase (Fermentas) using the following PCR parameters:

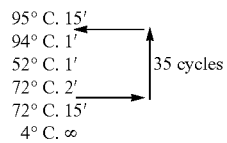

For said PCR a standard 5' primer (5' ATGGGATCCCCG-GTAATTAACACGCATC 3' (SEQ ID NO: 54)) and a standard 3' primer (5' AGCCGGTACGCCGCCAGCGGTACGC 3' (SEQ ID NO: 55)) was used. To extend the 5' end of the ORF which encodes P2gp09 with a gene fragment encoding the polycationic 9-mer peptide Lys-Arg-Lys-Lys-Arg-Lys-Lys-Arg-Lys (SEQ ID NO: 11) a tail PCR (with same parameters as standard PCR above) with an extended 5' primer (5' ATGGGATCCAAACGCAAGAAACG-TAAGAAACGC AAACCGGTAATTAACACGCATC 3' (SEQ ID NO: 56) and the standard 3' primer according to SEQ ID NO 55 was applied. Both the original unmodified P2gp09 PCR fragment and the extended fragment were ligated in the pEXP5CT/TOPO® expression vector (Invitrogen, Carlsbad, Calif., USA) by following the TA-cloning protocol of the manufacturer.

Recombinant expression of P2gp09 according to SEQ ID NO: 9 and PKP2gp09 according to SEQ ID NO: 57 is performed in exponentially growing E. coli BL21 (λDE3) pLysS cells (Invitrogen) after induction with 1 mM IPTG (isopropylthiogalactoside) at 37° C. for a period of 4 hours. Both proteins were purified by $Ni^{2+}$ affinity chromatography (Akta FPLC, GE Healthcare) using the C-terminal 6× His-tag, encoded by the pEXP5CT/TOPO® expression vector. The $Ni^{2+}$ affinity chromatography is performed in 4 subsequent steps, all on room temperature:

1. Equilibration of the Histrap HP 1 ml column (GE Healthcare) with 10 column volumes of Washing Buffer (60 mM imidazole, 0.5 mM NaCl and 20 mM $NaH_2PO_4$-NaOH on pH 7.4) at a flow rate of 0.5 ml/min.
2. Loading of the total lysate (with wanted endolysin) on the Histrap HP 1 ml column at a flow rate of 0.5 ml/min.
3. Washing of the column with 15 column volumes of Washing Buffer at a flow rate of 1 ml/min.
4. Elution of bounded endolysin from the column with 10 column volumes of Elution Buffer (500 mM imidazole, 5 mM NaCl and 20 mM $NaH_2PO_4$-NaOH on pH 7.4) at a flow rate of 0.5 ml/min The total yields of both purified recombinant proteins per liter E. coli expression culture shown in Table 7. The values were determined by spectrophotometric measurement of the protein concentration and the total volume of the purified stock solution at a wavelength of 280 nm. Purified stock solutions consisting of P2gp09 and PKP2gp09, respectively, in Elution Buffer (20 mM $NaH_2PO_4$-NaOH pH7.4; 0.5 M NaCl; 500 mM imidazole) were at least 95% pure as determined visually on SDS-PAGE gels.

TABLE 7

Yields of purified recombinant P2gp09 endolysin and its PK-modified derivative PKP2gp09 per liter E. coli expression culture.

| Endolysins | Expression yield |
|---|---|
| P2gp09 (SEQ ID NO: 9) | 5.52 mg |
| PKP2gp09 (SEQ ID NO: 57) | 3.40 mg |

To determine the anti-Gram-negative spectrum of the PK2gp09 endolysin according to SEQ ID NO: 57, a combination of 1.315 µM PK2gp09 endolysin and 0,5 mM EDTA was tested on the clinical P. aeruginosa strains PAO1p and Br667 and on Escherichia coli WK6 (see Table 9). Exponential growing bacterial cells ($OD_{600\,nm}$ of 0.6) were 100-fold diluted to a final density of about $10^6$/ml of each strain was incubated for 30 minutes at room temperature without shaking with unmodified endolysin P2gp09 (SEQ ID NO: 9) and modified endolysin PKP2gp09 (SEQ ID NO: 57) each in combination without and with 0.5 mM EDTA. For incubation, the endolysins were used each in buffer (20 mM $NaH_2PO_4$-NaOH pH7.4; 0.5 M NaCl; 0.5 M imidazole) and the incubation took place at a final concentration of endolysin of 1.315 µM. As a control each strain was also incubated for 30 minutes with 0.5 mM EDTA (in same buffer as outlined above) but no endolysin. After incubation cell suspensions were diluted three times (respectively $10^5$-$10^4$-$10^3$ cells/ml) and 100 µl of each dilution was plated out on LB-medium. The residual colonies were counted after an overnight incubation on 37° C. Based on the counted cell numbers the antibacterial activity as the relative inactivation in logarithmic units (=$log_{10}N_0/N_i$ with $N_0$=number of untreated cells and $N_i$=number of treated cells, both counted after incubation) was calculated (Table 8).

TABLE 8

Antibacterial activity of unmodified endolysin (P2gp09) and its modified endolysin variant (P2gp09) with and without EDTA-$Na_2$ on different exponential growing Gram-negative species.

| | 0.5 mM EDTA | 1.315 µM P2gp09 | 1.315 µM PKP2gp09 | Δ | 1.315 µM P2gp09 + 0.5 mM EDTA | 1.315 µM PKP2gp09 + 0.5 mM EDTA | Δ |
|---|---|---|---|---|---|---|---|
| P. aeruginosa PAO1p | 0.330 +/− 0.146 | 0.374 +/− 0.084 | 0.326 +/− 0.069 | −0.038 | 2.840 +/− 0.079 | 3.172 +/− 0.056 | 0.332 |
| P. aeruginosa Br667 | 0.003 +/− 0.051 | 0.246 +/− 0.042 | 0.300 +/− 0.062 | 0.054 | 0.582 +/− 0.074 | 0.952 +/− 0.213 | 0.370 |
| P. putida G1 | 0.072 +/− 0.084 | 0.419 +/− 0.024 | 1.014 +/− 0.139 | 0.595 | 3.919 +/− 0.118 | >4,386 | >0.467 |
| Burkholderia pseudomallei | 0.206 +/− 0.151 | 0.769 +/− 0.110 | 1.163 +/− 0.073 | 0.394 | 3.8909 +/− 0.056 | 4.255 +/− 0.001 | 0.365 |
| Escherichia coli WK6 | 0.153 +/− 0.046 | 0.751 +/− 0.053 | 1.104 +/− 0.039 | 0.353 | 0.784 +/− 0.071 | 1.545 +/− 0.102 | 0.749 |

All samples were replicated in threefold. Averages+/− standard deviations are represented. The maximal reduction observed is dependent on the detection level of 10 cells/ml and the initial cell density.

TABLE 9

List of used Gram-negative strains

| Gram-negative strain | Source | Reference |
|---|---|---|
| Pseudomonas aeruginosa PAO1p | Burn wound isolate, Queen Astrid Hospital, Brussels | Pirnay et al., 2003* |
| Pseudomonas aeruginosa Br667 | Burn wound isolate, Queen Astrid Hospital, Brussels | Pirnay et al., 2003* |
| Burkholderia pseudomallei | Clinical isolate, UZ Gasthuisberg, Leuven | Prof J. Verhaegen |
| Escherichia coli WK6 | Standard laboratory expression strain | Prof C. Michiels |
| Pseudomonas putida G1 | Soil isolate, Moskow | Prof V. Krylov |

*Pirnay J P et al., (2003). Molecular epidemiology of Pseudomonas aeruginosa colonization in a burn unit: persistence of a multidrug-resistant clone and a silver sulfadiazine-resistant clone. J Clin Microbiol., 41(3): 1192-1202.

EXAMPLE 7

Modified Endolysin Variants of *Pseudomonas putida* Phage OBP

OBPgpLYS according to SEQ ID NO: 7 is a modular endolysin of 328 amino acid residues originating from *Pseudomonas putida* phage OBP with a putative N-terminal peptidoglycan binding domains and a C-terminal catalytic chitinase domain. As predicted by BLASTp and Pfam analysis the OBPgpLYS endolysin comprises its catalytic domain in the range of about amino acid residue 126 to about amino acid residue 292 and the N-terminal peptidoglycan binding domain in the range of about amino acid residues 7 to 96.

Purified genomic DNA of phage OBP was used as a template for the amplification of the open reading frame (ORF) of OBPgpLYS in standard PCR reaction with Pfu polymerase (Fermentas, Ontario, Canada) using the following PCR parameters:

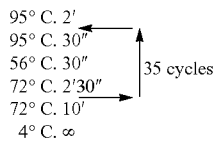

Therefore a standard 5' primer (5' ATGAAAAATAGC-GAGAAGAAT 3' (SEQ ID NO: 58)) and a standard 3' primer (5' AACTATTCCGAGTGCTTTCTTTGT 3' (SEQ ID NO: 59)) was used. To extend the 5' end of the ORF which encodes OBPgpLYS with a gene fragment encoding the polycationic 9-mer peptide Lys-Arg-Lys-Lys-Arg-Lys-Lys-Arg-Lys- (SEQ ID NO: 11) a tail PCR (with same parameters as standard PCR above) with an extended 5' primer (5' ATGGGATCCAAACGCAAGAAACG-TAAGAAACGCAAAAAAAATAGCGAG AAGAAT 3' (SEQ ID NO: 60)) and the standard 3' primer according to SEQ ID NO 59 was applied. Both the original unmodified OBPgpLYS PCR fragment and the extended fragment were ligated in the pEXP5CT/TOPO® expression vector (Invitrogen, Carlsbad, Calif., USA) by following the TA-cloning protocol of the manufacturer.

Recombinant expression of OBPgpLYS according to SEQ ID NO: 7 and PKOBPgpLYS according to SEQ ID NO: 61 is performed in exponentially growing *E. coli* BL21 (λDE3) pLysS cells (Invitrogen) after induction with 1 mM IPTG (isopropylthiogalactoside) at 37° C. for a period of 4 hours. Both proteins were purified by $Ni^{2+}$ affinity chromatography (Akta FPLC, GE Healthcare) using the C-terminal 6× His-tag, encoded by the pEXP5CT/TOPO® expression vector. The $Ni^{2+}$ affinity chromatography is performed in 4 subsequent steps, all on room temperature:

1. Equilibration of the Histrap HP 1 ml column (GE Healthcare) with 10 column volumes of Washing Buffer (60 mM imidazole, 0.5 mM NaCl and 20 mM $NaH_2PO_4$-NaOH on pH 7.4) at a flow rate of 0.5 ml/min.
2. Loading of the total lysate (with wanted endolysin) on the Histrap HP 1 ml column at a flow rate of 0.5 ml/min.
3. Washing of the column with 15 column volumes of Washing Buffer at a flow rate of 1 ml/min.
4. Elution of bounded endolysin from the column with 10 column volumes of Elution Buffer (500 mM imidazole, 5 mM NaCl and 20 mM $NaH_2PO_4$-NaOH on pH 7.4) at a flow rate of 0.5 ml/min The total yields of both purified recombinant proteins per liter *E. coli* expression culture shown in Table 10. The values were determined by spectrophotometric measurement of the protein concentration and the total volume of the purified stock solution at a wavelength of 280 nm. Purified stock solutions consisting of OBPgpLYS and PKOBPgpLYS, respectively, in Elution Buffer (20 mM $NaH_2PO_4$-NaOH pH7.4; 0.5 M NaCl; 500 mM imidazole) were at least 90% pure as determined visually on SDS-PAGE gels.

TABLE 10

Yields of purified recombinant OBPgpLYS endolysin and its PK-modified derivative PKOBPgpLYS per liter *E. coli* expression culture.

| Endolysins | Expression yield |
|---|---|
| OBPgpLYS (SEQ ID NO: 7) | 3.3 mg |
| PKOBPgpLYS (SEQ ID NO: 61) | 4.7 mg |

To determine the anti-Gram-negative spectrum of the PKOBPgpLYS endolysin according to SEQ ID NO: 61, a combination of 1.313 μM PK OBPgpLYS endolysin and 0.5 mM EDTA was tested on the clinical multiresistant *P. aeruginosa* strain Br667, *Pseudomonas putida* G1 (host of phage OBP) and a range of other Gram-negative pathogens (*Escherichia coli* WK6, *Salmonella typhimurium* LT2 and *Burkholderia pseudomallei*) (see Table 12). Exponential growing bacterial cells ($OD_{600\ nm}$ of 0.6) were 100-fold diluted to a final density of about $10^6$/ml of each strain was incubated for 30 minutes at room temperature without shaking with unmodified endolysin OBPgpLYS (SEQ ID NO: 7) and modified endolysin PKOBPgpLYS (SEQ ID NO: 61) each in combination without and with 0.5 mM EDTA. For incubation, the endolysins were used each in buffer (20 mM $NaH_2PO_4$-NaOH pH7.4; 0.5 M NaCl; 0.5 M imidazole) and the incubation took place at a final concentration of endolysin of 1.313 μM. As a control each strain was also incubated for 30 minutes with 0.5 mM EDTA (in same buffer as outlined above) but no endolysin. After incubation cell suspensions were diluted three times (respectively $10^5$-$10^4$-$10^3$ cells/ml) and 100 μl of each dilution was plated out on LB-medium. The residual colonies were counted after an overnight incubation on 37° C. Based on the counted cell numbers the antibacterial activity as the relative inactivation in logarithmic units ($=\log_{10}N_0/N_i$ with $N_0$=number of untreated cells and $N_i$=number of treated cells, both counted after incubation) was calculated (Table 11). All samples were replicated in threefold. Averages+/− standard deviations are represented. The maximal reduction observed is dependent on the detection level of 10 cells/ml and the initial cell density.

TABLE 11

Antibacterial activity of unmodified endolysin (OBPgpLYS) and its modified endolysin variant (PKOBPgpLYS) with and without EDTA-Na$_2$ on different exponential growing Gram-negative species.

| | 0.5 mM EDTA | 1.313 µM OBPgpLYS | 1.313 µM PKOBPgpLYS | 1.313 µM OBPgpLYS + 0.5 mM EDTA | 1.313 µM PKOBPgpLYS + 0.5 mM EDTA |
|---|---|---|---|---|---|
| P. aeruginosa PAO1p | 0.130 +/− 0.023 | 2.531 +/− 0.173 | 3.079 +/− 0.015 | 4.357 +/− 1.857 | >5.687 |
| P. aeruginosa Br667 | 0.031 +/− 0.023 | 1.082 +/− 0.083 | 1.163 +/− 0.063 | 3.144 +/− 0.223 | 5.272 +/− 0.573 |
| P. putida G1 | 0.412 +/− 0.055 | 0.141 +/− 0.027 | 0.904 +/− 0.079 | 4.891 +/− 0.000 | >4.891 |
| Burkholderia pseudomallei | 0.220 +/− 0.081 | 0.997 +/− 0.131 | 1.806 +/− 0.287 | 4.08 +/− 0.301 | >4.861 |
| Escherichia coli WK6 | 0.592 +/− 0.113 | 0.681 +/− 0.032 | 1.434 +/− 0.018 | 1.179 +/− 0.200 | 1.695 +/− 0.147 |
| Salmonella typhimurium | 0.054 +/− 0.048 | 0.076 +/− 0.011 | 0.127 +/− 0.013 | 0.774 +/− 0.052 | 0.908 +/− 0.037 |

TABLE 12

List of used Gram-negative strains

| Gram-negative strain | Source | Reference |
|---|---|---|
| Pseudomonas aeruginosa PAO1p | Burn wound isolate, Queen Astrid Hospital, Brussels | Pirnay et al., 2003* |
| Pseudomonas aeruginosa Br667 | Burn wound isolate, Queen Astrid Hospital, Brussels | Pirnay et al., 2003* |
| Pseudomonas putida G1 | Soil isolate, Moskow | Prof V. Krylov |
| Burkholderia pseudomallei | Clinical isolate, UZ Gasthuisberg, Leuven | Prof J. Verhaegen |
| Escherichia coli WK6 | Standard laboratory expression strain | Stratagene |
| Salmonella typhimurium LT2 | SGSC N° 2317 | Prof C. Michiels |

*Pirnay J P, De Vos D, Cochez C, Bilocq F, Pirson J, Struelens M, Duinslaeger L, Cornelis P, Zizi M, Vanderkelen A. (2003). Molecular epidemiology of Pseudomonas aeruginosa colonization in a burn unit: persistence of a multidrug-resistant clone and a silver sulfadiazine-resistant clone. J Clin Microbiol., 41(3): 1192-1202.

While the global efficacy of the OBPgpLYS treatment is species dependent, the results in table 11 show an added effect of the PKOBPgpLYS compared to unmodified OBPgpLYS for all bacterial species tested, both in the absence as the presence of 0.5 mM EDTA. For Pseudomonas and Burkholderia species, a clear synergistic effect with EDTA is observed for the PKOBPgpLYS activity.

EXAMPLE 8

Effect of Different EDTA Concentration on the Antibacterial Activity of OBPgpLYS and PKOBPgpLYS To determine the influence of EDTA on the antibacterial activity of unmodified and modified endolysins the antibacterial activity of the unmodified OBPgpLYS endolysin (SEQ ID NO: 7) and the PKOBPgpLYS endolysin (SEQ ID NO: 61) was tested on Pseudomonas aeruginosa PAO1p cells (Pirnay J P et al. J Clin Microbiol., 41(3):1192-1202 (2003)) using different concentrations of EDTA and endolysins. Exponential growing bacterial cells ($OD_{600\ nm}$ of 0.6) were 100-fold diluted to a final density of about $10^6$/ml and incubated for 30 minutes at room temperature without shaking with unmodified endolysin OBPgpLYS (SEQ ID NO: 7) and modified endolysin PKOBPgpLYS (SEQ ID NO: 61). For incubation, the endolysins were used each in buffer (20 mM $NaH_2PO_4$-NaOH pH7.4; 0.5 M NaCl; 0.5 M imidazole) at final concentrations of endolysin of 0.013 µM, 0.131 µM and 1.315 µM. Thereby, the following different EDTA concentrations were used: 0 mM, 0.05 mM, 0.5 mM and 10 mM. As a control one sample was also incubated for 30 minutes with no endolysin, instead of there was buffer (20 mM $NaH_2PO_4$-NaOH pH7.4; 0.5 M NaCl; 0.5 M imidazole) added. After incubation cell suspensions were diluted three times (respectively $10^5$-$10^4$-$10^3$ cells/ml) and 100 µl of each dilution was plated out on LB-medium. The residual colonies were counted after an overnight incubation on 37° C. Based on the counted cell numbers the antibacterial activity as the relative inactivation in logarithmic units (=$\log_{10} N_0/N_i$ with $N_0$=number of untreated cells and $N_i$=number of treated cells, both counted after incubation) was calculated (Table 13). All samples were replicated in threefold. Averages+/−standard deviations are represented. The maximal reduction observed (5.69 log units) is dependent on the detection level of 10 cells/ml and the initial cell density. "Δ" gives the difference of activity between the respective OBPgpLYS and PKOBPgpLYS samples.

TABLE 13

Antibacterial activity of unmodified endolysin (OBPgpLYS) and its modified endolysm variant (PKOBPgpLYS) in combination with different EDTA concentrations on exponential growing Pseudomonas aeruginosa PAO1p cells

| | Concentration of EDTA-Na$_2$ (in mM) | | | |
|---|---|---|---|---|
| | 0 | 0.05 | 0.5 | 10 |
| No endolysin | / | 0.028 +/− 0.008 | 0.130 +/− 0.023 | 1.827 +/− 0.052 |
| 0.013 µM OBPgpLYS | 0.956 +/− 0.110 | / | 4.626 +/− 0.287 | / |
| 0.013 µM PKOBPgpLYS | 0.992 +/− 0.181 | / | 5.204 +/− 0.000 | / |
| Δ | 0.036 | | 0.578 | |
| 0.131 µM OBPgpLYS | 2.158 +/− 0.027 | / | 4.599 +/− 0.275 | / |
| 0.131 µM PKOBPgpLYS | 2.529 +/− 0.184 | / | 5.671 +/− 0.000 | / |
| Δ | 0.371 | | 1.072 | |

TABLE 13-continued

Antibacterial activity of unmodified endolysin (OBPgpLYS) and its modified endolysm variant (PKOBPgpLYS) in combination with different EDTA concentrations on exponential growing Pseudomonas aeruginosa PAO1p cells

| | Concentration of EDTA-Na$_2$ (in mM) | | | |
|---|---|---|---|---|
| | 0 | 0.05 | 0.5 | 10 |
| 1.315 µM OBPgpLYS | 2.531 +/− 0.173 | 2.762 +/− 0.091 | 4.357 +/− 1.857 | 4.888 +/− 0.275 |
| 1.315 µM PKOBPgpLYS | 3.079 +/− 0.015 | 4.145 +/− 0.015 | >5.687 | >5.687 |
| Δ | 0.548 | 1.383 | >1.330 | >0.799 |

As shown in Table 13 unmodified endolysin OBPgpLYS reduces cell numbers significantly with more than 2.5 log units for 1.315 µM and with +/− 1 log unit for 0.013 µM, compared to the negative control. Modified endolysin PKOBPgpLYS results in an added 0.5 log units reduction for exponentially growing PAO1p cells. The observed antibacterial effect can be increased to more as 5.69 log units reduction (beneath the detection level) by combining PKOBPgpLYS with the outer membrane permeabilizer EDTA-Na$_2$ at a concentration of 0.5 and 10 mM EDTA. The difference in activity between the unmodified OBPgpLYS and the PK-modified OBPgpLYS increases by raising the amount of added endolysin (from 0.013-1.315 µM endolysin).

EXAMPLE 9

Antibacterial Activity of Modified phiKZgp144 Variants on Different Gram-Negative Bacteria To test and to compare the potential of polycationic peptides variants of phiKZgp144 and other endolysins, encoding genes were synthesised having polycationic peptides at the N-terminal end of the protein.

The different products were cloned in the pET32b expression vector (Novagen, Darmstadt, Germany). pET32b was used to reduce potential toxicity of the polycationic peptide against the E. coli host. A vector-encoded fusion protein (thioredoxin) masks the polycationic peptide and can be eliminated during the purification process.

The genes encoding smi01 (YP_001712536) and KRK9_smi01 (SEQ ID NO: 75) were fully synthesised (Entelechon, Regensburg, Germany) and cloned into pET32b.

Accordingly, the following modified endolysin variants were expressed in E. coli BL21 (DE3) cells at 37° C. until an optical density of OD600 nm=0.6 was reached: smi01 (YP_001712536), KRK9_smi01 (SEQ ID NO: 75), phiKZgp144 (SEQ ID NO: 1), pKKZ144pET32b (SEQ ID NO: 43) and POLYKZ144 (SEQ ID NO: 35). Protein expression was induced with 1mM IPTG (final concentration) and expression was preformed for four hours. Then E. coli cells were harvested by centrifugation for 20 min at 6000 g and cell disruption and protein purification was performed using the S-Tag™ rEK Purification Kit (Novagen, Darmstadt, Germany). Using the pET32b vector, the expressed proteins were not toxic to the host resulting in high yields of produced protein. Purified stock solutions showed high purity.

For testing and as reference for comparison phiKZgp144 and POLYgp144 were synthesized and purified as described in EXAMPLE 1.

Exponential (~10$^6$/ml) growing cells of P. aeruginosa PAO1p (Burn wound isolate, Queen Astrid Hospital, Brussels; Pirnay J P et al. (2003), J Clin Microbiol., 41(3):1192-1202), Acinetobacter baumanii (DSMZ 30007) or Burkholderia solanaceum (Isolate provided by Prof. C. Michiels) were 100× diluted (final density was ~10$^6$/ml) incubated at room temperature with each 10 µg undialyzed protein as listed above at a final concentration of 100 µg/ml in buffer (20 mM NaH$_2$P0$_4$-NaOH pH7.4; 0.5 M NaCl; 0.5 M imidazole). After 1 hour cell suspensions were diluted 1:100 and plated on LB. Additionally, a negative control was plated using buffer (20 mM NaH$_2$P0$_4$-NaOH pH7.4; 0.5 M NaCl; 0.5 M imidazole). The residual colonies were counted after an overnight incubation at 37° C. Based on the counted cell numbers the antibacterial activity as the relative inactivation (%) (=100−(N$_f$/No)*100 with N$_0$=number of untreated cells and N$_i$=number of treated cells) was calculated (Table 3). All samples were replicated at least in four fold.

TABLE 14

Antibacterial effect of different modified endolysin variants (NCBI numbers in brackets) on different bacterial species

| Protein | Bacterial species | Reduction [%] |
|---|---|---|
| smi01 (YP_001712536) | Acinetobacter baumannii DSMZ 30007 | 0 |
| KRK9_smi01 | Acinetobacter baumannii DSMZ 30007 | 50 |
| phiKZgp144 | Pseudomonas aeruginosa | 0 |
| pKKZ144pET32b | Pseudomonas aeruginosa | 99-99.9 |
| phiKZgp144 | Acinetobacter baumannii DSMZ 30007 | 0 |
| pKKZ144pET32b | Acinetobacter baumannii DSMZ 30007 | 99.9 |
| phiKZgp144 | Burkholderia solanacearum | 0 |
| POLYKZ144 | Burkholderia solanacearum | 99-99.9 |

Unmodified endolysins phiKZgp144 and smi01 (YP_001712536) do not reduce cell numbers significantly compared to the negative control. This observation again illustrates the efficacy of the outer membrane as a barrier for the endolysin to degrade the cell wall of the Gram-negative bacteria. In contrast as shown in Table 14 the incubation with the modified endolysins KRK9_smi01, pKKZ144pET32b and POLY-gp144 causes a significant reduction of the bacterial cell number on Acinetobacter baumanii (50% for KRK_smi01; 99.9% for pKKZ144pET32b), Pseudomonas aeruginosa (90-99.9% for pKKZ144pET32b) and Burkholderia solanaceum (90-99.9% for POLYKZ144).

These experiments demonstrate the applicability of the cationic/polycationic fusion approach for other endolysins. Moreover, the experiments demonstrated that the modified endolysins are active on a variety of bacteria.

The invention claimed is:

1. An endolysin variant comprising an bacteriophage peptidoglycan hydrolase to which a cationic peptide stretch with LPS disrupting activity is fused, wherein said cationic peptide stretch consists of 5 to 50 amino acid residues and wherein at least 70% of the amino acid residues comprised in said peptide stretch are arginine and/or lysine and 0% to 30% are serine and/or glycine, and wherein said endolysin variant exhibits (i) the activity of degrading a cell wall of Gram-negative bacteria and (ii) LPS disrupting activity.

2. The endolysin variant according to claim 1, wherein said cationic peptide stretch consists of 5 to 30 amino acid residues.

3. The endolysin variant according to claim 1, wherein said cationic peptide stretch is fused to the N- and/or the C-terminus of the endolysin, in particular to the N-terminus of the endolysin.

4. The endolysin variant according to claim 1, wherein said endolysin is selected from the group consisting of phiKZgp144 according to SEQ ID NO:1, ELgp188 according to SEQ ID NO:2, *Salmonella* endolysin according to SEQ ID NO:3, Enterobacteria phage T4 endolysin according to SEQ ID NO:4, *Acinetobacter baumanii* endolysin according to SEQ ID NO:5, *E.coli* Phage K1F endolysin according to SEQ ID NO:6, PSP3 *salmonella* endolysin according to SEQ ID NO: 8 and *E. coli* Phage P2 endolysin according to SEQ ID NO: 9.

5. The endolysin variant according to claim 1, wherein said cationic peptide stretch comprises at least one KRK motif, in particular wherein said peptide stretch consists of a sequence selected from the group consisting of SEQ ID: 10 to 30.

6. The endolysin variant according to claim 1, wherein said endolysin variant comprises an amino acid sequence selected from the group consisting of SEQ ID NO: 35 to 49, 53, 57, 62 to 64 and 66 to 78.

7. An isolated nucleic acid molecule comprising a nucleotide sequence coding an endolysin variant according to claim 1.

8. A vector comprising the nucleic acid molecule according to claim 7.

9. A host cell comprising a vector according to claim 8, wherein said host cell is in particular a bacterial cell or a yeast cell.

10. A method for the production of an endolysin variant comprising culturing a host cell according to claim 9 under conditions supporting the expression of said endolysin variant.

11. A method of treating a Gram-negative bacterial infection in a subject comprising administering to said subject an endolysin variant according to claim 1.

12. A method for the removal, reduction and/or prevention of Gram-negative bacterial contamination of foodstuff, of food processing equipment, of food processing plants, of surfaces coming into contact with foodstuff, of medical devices, of surfaces in hospitals and surgeries comprising contacting said foodstuff, food processing equipment, food processing plants, surfaces coming into contact with foodstuff, medical devices, or surfaces in hospitals with an endolysis variant according to claim 1.

13. A method for detecting bacterium in a sample from a subject or in a food or feed, or environmental sample comprising contacting said a sample with an endolysin variant according to claim 1.

14. A pharmaceutical composition comprising an endolysin variant according to claim 1.

15. The endolysin variant according to claim 1, wherein the cell wall of the Gram-negative bacteria selected from the group consisting of
Enterobacteriaceae,
in particular *Escherichia, Salmonella, Shigella, Citrobacter, Edwardsiella, Enterobacter, Hafnia, Klebsiella, Morganella, Proteus, Providencia, Serratia*, and *Yersinia*,
Pseudomonadaceae,
in particular *Pseudomonas, Burkholderia, Stenotrophomonas, Shewanella, Sphingomonas* and *Comamonas*,
*Neisseria, Moraxella, Vibrio, Aeromonas, Brucella, Francisella, Bordetella, Legionella, Bartonella, Coxiella, Haemophilus, Pasteurella, Mannheimia, Actinobacillus, Gardnerella*,
Spirochaetaceae,
in particular *Treponema* and *Borrelia*,
Leptospiraceae, *Campylobacter, Helicobacter, Spirillum, Streptobacillus*, Bacteroidaceae,
in particular *Bacteroides, Fusobacterium, Prevotella* and *Porphyromonas*, and *Acinetobacter*,
in particular *A. baumanii*.

* * * * *

UNITED STATES PATENT AND TRADEMARK OFFICE
CERTIFICATE OF CORRECTION

PATENT NO.        : 9,809,808 B2                                          Page 1 of 1
APPLICATION NO.   : 13/061053
DATED             : November 7, 2017
INVENTOR(S)       : Briers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 892 days.

Signed and Sealed this
Twenty-fifth Day of September, 2018

Andrei Iancu
*Director of the United States Patent and Trademark Office*